United States Patent
Logan et al.

(10) Patent No.: US 11,104,917 B2
(45) Date of Patent: Aug. 31, 2021

(54) PROMOTERS FOR EXPRESSION OF HETEROLOGOUS GENES

(71) Applicants: Children's Medical Research Institute, Westmead (AU); The Sydney Children's Hospital Network (Randwich and Westmead) (incorporating The Royal Alexandra Hospital For Children, Westmead (AU)

(72) Inventors: Grant Logan, Westmead (AU); Ian Alexander, Pennant Hills (AU); Allison Dane, London (GB)

(73) Assignees: CHILDREN'S MEDICAL RESEARCH INSTITUTE, Westmead (AU); THE SYDNEY CHILDREN'S HOSPITALS NETWORK (RANDWICK AND WESTMEAD) (INCORPORATING THE ROYAL ALEXANDRA HOSPITAL FOR CHILDREN), Westmead (AU)

( * ) Notice: Subject to any disclaimer, the term of this patent is extended or adjusted under 35 U.S.C. 154(b) by 524 days.

(21) Appl. No.: 15/572,101

(22) PCT Filed: May 4, 2016

(86) PCT No.: PCT/AU2016/050320
§ 371 (c)(1),
(2) Date: Nov. 6, 2017

(87) PCT Pub. No.: WO2016/179644
PCT Pub. Date: Nov. 17, 2016

(65) Prior Publication Data
US 2018/0142260 A1    May 24, 2018

(30) Foreign Application Priority Data

May 8, 2015  (AU) ............................ 2015901677

(51) Int. Cl.
| | |
|---|---|
| C12N 15/864 | (2006.01) |
| C12N 15/85 | (2006.01) |
| C12N 15/11 | (2006.01) |
| C12N 15/63 | (2006.01) |
| A61K 48/00 | (2006.01) |
| C12N 15/113 | (2010.01) |
| C12N 15/86 | (2006.01) |
| C12N 15/867 | (2006.01) |
| C12N 15/869 | (2006.01) |

(52) U.S. Cl.
CPC ......... *C12N 15/8645* (2013.01); *C12N 15/86* (2013.01); *C12N 15/867* (2013.01); *C12N 15/869* (2013.01); *C12N 2740/15043* (2013.01); *C12N 2750/14122* (2013.01); *C12N 2750/14143* (2013.01); *C12N 2830/60* (2013.01)

(58) Field of Classification Search
None
See application file for complete search history.

(56) References Cited

U.S. PATENT DOCUMENTS

| | | | |
|---|---|---|---|
| 6,033,885 A | 3/2000 | Latta et al. | |
| 6,995,010 B1 | 2/2006 | Ueno et al. | |
| 2012/0054880 A1 | 3/2012 | Tsai et al. | |
| 2013/0323302 A1* | 12/2013 | Constable | A61K 48/0075 424/450 |

FOREIGN PATENT DOCUMENTS

WO   2014140051 A1   9/2014

OTHER PUBLICATIONS

Damdindorj, L , et al., "A Comparative Analysis of Constitutive Promoters Located in Adeno-Associated Viral Vectors", PLOS One 9(8), e106472, 10 pages (2014).
Flotte, T , et al., "Expression of the cystic fibrosis transmembrane conductance regulator from a novel adeno-associated virus promoter", Journal of Biological Chemistry 268(5), 3781-3790 (1993).
Logan, G , et al., "Identification of liver-specific enhancer—promoter activity in the 3' untranslated region of the wild-type AAV2 genome", Nature Genetics 49(8), 1267-1273 (2017).
Maxwell, F , et al., "Improved production of recombinant AAV by transient transfection of NB324K cells using electroporation", Journal of Virological Methods 63, 129-136 (1997).
Yan, Z , et al., "Optimization of Recombinant Adeno-Associated Virus-Mediated Expression for Large Transgenes, Using a Synthetic Promoter and Tandem Array Enhancers", Human Gene Therapy 26, 334-346 (2015).
Laughlin, et al., "Cloning of infectious adeno-associated virus genomes in bacterial phsmids", Gene 23, 65-73 (1983).
Samulski, et al., "A Recombinant Plasmid from Which an Infectious Adeno-Associated Virus Genome Can Be Excised In Vitro and Its Use to Study Viral Replication", Journal of Virology 61 (10), 3096-3101 (1987).
Kobelska-Dubiel, N , et al., "Liver disease in cystic fibrosis", Prz Gastroenterol 9(3), 136-141 (2014).

* cited by examiner

*Primary Examiner* — Maria Marvich
(74) *Attorney, Agent, or Firm* — Viksnins Harris Padys Malen LLP

(57) ABSTRACT

The present disclosure relates generally to promoters derived from the AAV anti-sense strand, their use in the expression of one or more heterologous coding sequences, and isolated polynucleotides, vectors and recombinant viruses comprising the promoters. The present disclosure also relates to enhancers derived from the AAV anti-sense strand, their use in increasing the expression of one or more heterologous coding sequences, and isolated polynucleotides, vectors and recombinant viruses comprising the enhancers.

22 Claims, 13 Drawing Sheets

Specification includes a Sequence Listing.

FIGURE 5

```
         ITR
         ←─────────────────┐
AAV4R&C  GGCCAACTCCATCATCTGGTTTGCC---AGAAGTTACTGATTAACCGGCAGTTGTAAACCG
AAV2R&C  GGCCAACTCCATCACTAGGGGTTCCTTGTAGTTAATGATTAACCCG---------------
AAV3R&C  GGCCAACTCCATCACTAGAGGTATGGGAGAGTTAAATATTAACCAGCAGTTGTAAACCG
AAV8R&C  ------------------------------------------------------------
AAV7R&C  GGCCAACTCCATCACTAGGGGTACCCCGGTGACGTCAGTGTTCTTATCGT-----------
AAV1R&C  GGCCAACTCCATCACTAGGGGTAACCCGATGACGTAAGTCTTTTAT-CGC-----------
AAV6R&C  GGCCAACTCCATCACTAGGGGTATTCGCGA-------------------------------
         .,**.*: *       ..    *

AAV4R&C  CGAAGCGCAAGCGCCGCAGGCCGCTGCTTATGTACGCAGTAGCCATG---GAAACGAGATA
AAV2R&C  --------------C--CATGC---TA---CTT---ATCTACGTAGCCATGGAAACTAGAT
AAV3R&C  CGAAGCGCAAGCGCCGCAGGCCGCTGCTTATCTACGCAGTAGCCATGGAAACAAGATAAA
AAV8R&C  ------------------------------------------------------------
AAV7R&C  -GAAGCGCACC-----CAAGCAGTTAATGTGTAACCA-G----TTGCTATGGAAACCGAT
AAV1R&C  -GAAGCGCAAC-----CAAGCAGTTAATGTGTAAGCTAT----AACCAT-GGTAACCGAT
AAV6R&C  ---AGCGCAAC-----TAAGCAGTTAATGTGTAACCGGT----TGCTATGGTGACCAGAT
           . *  *.                                   .       .:

AAV4R&C  AGATAAGAAGGACACGGAGACCAAAGTTCAACTGAAACGAATAAACCGGTTTATTGATTA
AAV2R&C  AAGAAAGAAATACGCAGAGACCAAAGTTCAACTGAAACGAATTAAACGGTTTATTGATTA
AAV3R&C  GATAAAGAAGTGCACAAGAGCCAAAGTTCAACTGAAACGAATTAAACGGTTTATTGATTA
AAV8R&C  -----------CGCAGAGACCAAAGTTCAACTGAAACGAATCAACCGGTTTATTGATTA
AAV7R&C  AAGATAAGAAGGACAGGAGACCAAAGTTCAACTGAAACGAATCAACCGGTTTATTGATTA
AAV1R&C  AAGATAAGAAGGACAGGAGACCAAAGTTCAACTGAAACGAATCAACCGGTTTATTGATTA
AAV6R&C  AAGATAATAACGACATGAGACCAAAGTTCAACTGACACGAATTAACCGGTTTATTGATTA
         ..::...  .   ....******************.****** **.**************

AAV4R&C  ACAGGTTATTACAGGTGGTGGGTGAGGTAGCGGGTACCGATAGCCCTAGGCTCAGTGTAT (SEQ ID NO:36)
AAV2R&C  ACAAGCAATTACAGATTACGAGTCAGGTATCTGGTGCCAATGGGGCGAGGCTCTGAATAC (SEQ ID NO:34)
AAV3R&C  ACCAGGATTCACAAGTTTCGTGTGAGATACCGGGTTCCAATAGGGCGAGGTTCACTATAA (SEQ ID NO:35)
AAV8R&C  ACAGGCAATTACAGATTACGGGTGAGGTAACGGGTGCCAATGGGGCGGGGTTCAGAGTAC (SEQ ID NO:39)
AAV7R&C  ACATGCAATTACAGATTACGGGTGAGGTAACGAGTGCCAATAGGGCGAGGCTCAGAGTAA (SEQ ID NO:38)
AAV1R&C  ACACGTAATTACAGGGGACGGGTAAGGTAACGGGTGCCAATGGGGCGAGGCTCAGTATAA (SEQ ID NO:33)
AAV6R&C  ACACACAATTACAGGGGACGGGTGAGGTAACGGGTGCCAATGGGGCGAGGCTCAGTATAA (SEQ ID NO:37)
         **.. .::* ***..    * ** **.** * .** **.**.*   * ** **: :.**
         └─────────────────────────────────────────────────────────────→
                                      capsid
```

FIGURE 7

<u>HNF1C</u>
HNF1
HNF4-alpha
▨ VP1 Stop codon
*GCGGCCGC*-Not I restriction site
*TCTAGA*-Xba I restriction site

AAV2-105 and 133:

*GCGGCCGC*TGTAGTTAATGATTAACCCGCCATGCTACTTATCTACGTAGCCATGGAAACTAGATAAGAAAGAAATACGCAGAGA
CCAAAGTTCAACTGAAACGAATTAAACGG*TCTAGA* (SEQ ID NO:40)
*GCGGCCGC*TGTAGTTAATGATTAACCCGCCATGCTACTTATCTACGTAGCCATGGAAACTAGATAAGAAAGAAATACGCAGAGA
CCAAAGTTCAACTGAAACGAATTAAACGGTTTATTGATTAACAAGCAA▨▨CAGATT*TCTAGA* (SEQ ID NO:41)

AAV5-121 and 149

*GCGGCCGC*GATGTTGTAAGCTGTTATTCATTGAATGACCACAAGAGGCAGTATTTTACTGACACGAATACACGGTTTATTGAGG
GTATGCGACATGAATGGG▨▨AAGGGGTCGGGTAAGGTATCGGGT*TCTAGA* (SEQ ID NO:42)
*GCGGCCGC*GATGTTGTAAGCTGTTATTCATTGAATGACCACAAGAGGCAGTATTTTACTGACACGAATACACGGTTTATTGAGG
GTATGCGACATGAATGGG▨▨AAGGGGTCGGGTAAGGTATCGGGTTCCGATAGGTCTGGTGGTTCTGTATTCC*TCTAGA*
(SEQ ID NO:43)

FIGURE 8
A
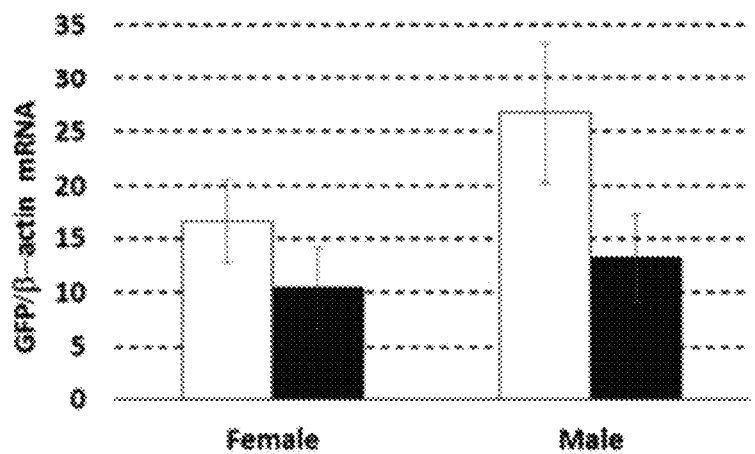
B
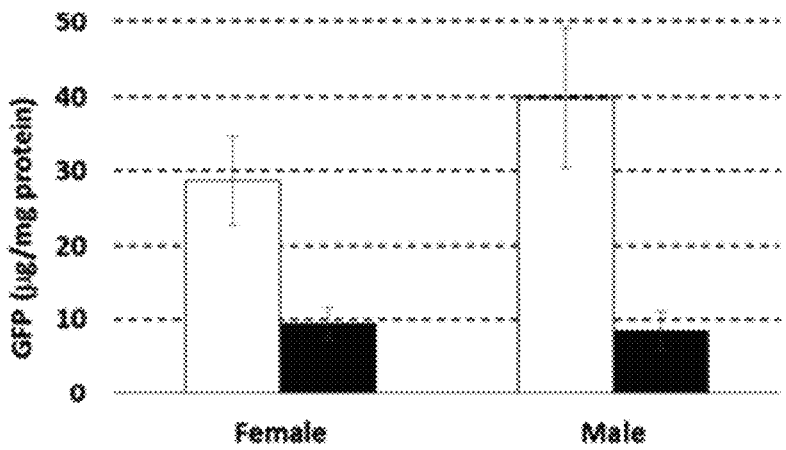

FIGURE 9
A
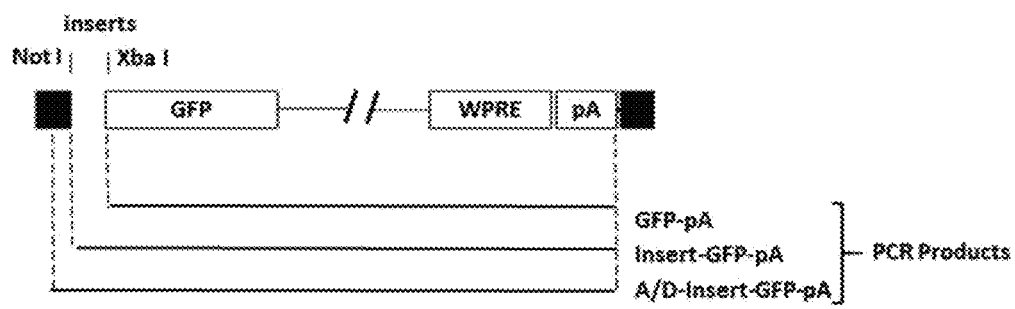
B
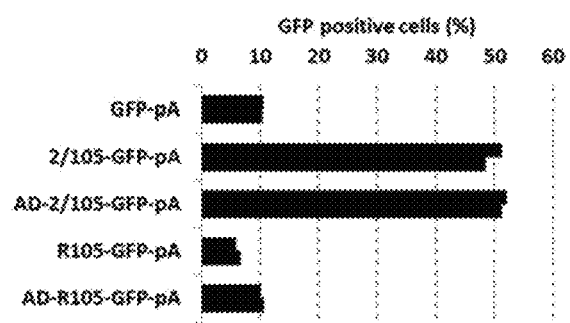
D
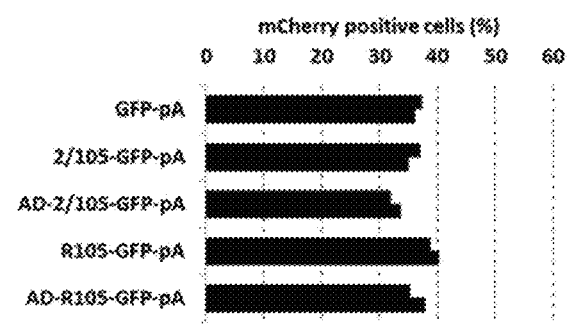
C
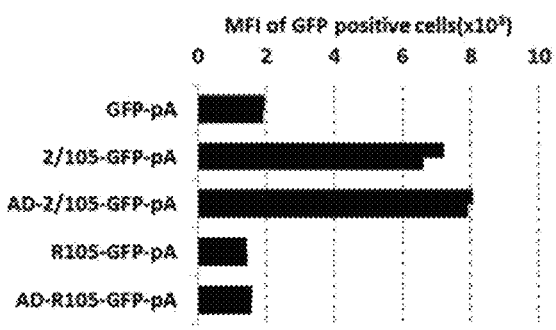
E
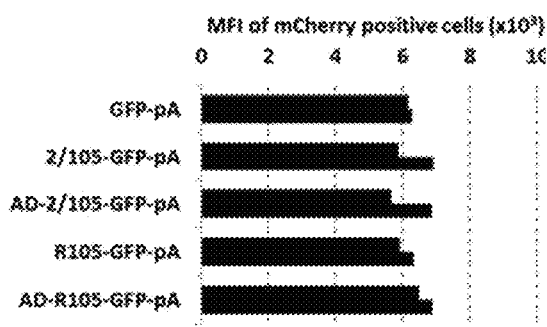

A.

B.

SEQUENCE LISTING

<160> NUMBER OF SEQ ID NOS: 43

<210> SEQ ID NO 1
<211> LENGTH: 4675
<212> TYPE: DNA
<213> ORGANISM: Adeno-associated virus serotype 2

<400> SEQUENCE: 1

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240
gtggtcacgc tgggtattta agcccgagtg agcacgcagg gtctccattt tgaagcggga     300
ggtttgaacg cgcagccgcc atgccggggt tttacgagat tgtgattaag gtccccagcg     360
accttgacgg gcatctgccc ggcatttctg acagctttgt gaactgggtg gccgagaagg     420
aatgggagtt gccgccagat tctgacatgg atctgaatct gattgagcag gcacccctga     480
ccgtggccga gaagctgcag cgcgactttc tgacggaatg gcgccgtgtg agtaaggccc     540
cggaggccct tttctttgtg caatttgaga agggagagag ctacttccac atgcacgtgc     600
tcgtggaaac caccggggtg aaatccatgg tttgggacg tttcctgagt cagattcgcg     660
aaaaactgat tcagagaatt taccgcggga tcgagccgac tttgccaaac tggttcgcgg     720
tcacaaagac cagaaatggc gccggaggcg ggaacaaggt ggtggatgag tgctacatcc     780
ccaattactt gctccccaaa acccagcctg agctccagtg ggcgtggact aatatggaac     840
agtatttaag cgcctgtttg aatctcacgg agcgtaaacg gttggtggcg cagcatctga     900
cgcacgtgtc gcagacgcag gagcagaaca aagagaatca gaatcccaat tctgatgcgc     960
cggtgatcag atcaaaaact tcagccaggt acatggagct ggtcgggtgg ctcgtggaca    1020
aggggattac ctcggagaag cagtggatcc aggaggacca ggcctcatac atctccttca    1080
atgcggcctc caactcgcgg tcccaaatca aggctgcctt ggacaatgcg ggaaagatta    1140
tgagcctgac taaaaccgcc cccgactacc tggtgggcca gcagcccgtg gaggacattt    1200
ccagcaatcg gatttataaa attttggaac taaacgggta cgatcccaa tatgcggctt    1260
```

-continued

```
ccgtctttct gggatgggcc acgaaaaagt tcggcaagag gaacaccatc tggctgtttg       1320
ggcctgcaac taccgggaag accaacatcg cggaggccat agcccacact gtgcccttct       1380
acgggtgcgt aaactggacc aatgagaact ttcccttcaa cgactgtgtc gacaagatgg       1440
tgatctggtg ggaggagggg aagatgaccg ccaaggtcgt ggagtcggcc aaagccattc       1500
tcggaggaag caaggtgcgc gtggaccaga aatgcaagtc ctcggcccag atagacccga       1560
ctcccgtgat cgtcacctcc aacaccaaca tgtgcgccgt gattgacggg aactcaacga       1620
ccttcgaaca ccagcagccg ttgcaagacc ggatgttcaa atttgaactc acccgccgtc       1680
tggatcatga ctttgggaag gtcaccaagc aggaagtcaa agactttttc cggtgggcaa       1740
aggatcacgt ggttgaggtg gagcatgaat tctacgtcaa aaagggtgga gccaagaaaa       1800
gacccgcccc cagtgacgca gatataagtg agcccaaacg ggtgcgcgag tcagttgcgc       1860
agccatcgac gtcagacgcg gaagcttcga tcaactacgc agacaggtac caaaacaaat       1920
gttctcgtca cgtgggcatg aatctgatgc tgtttccctg cagacaatgc gagagaatga       1980
atcagaattc aaatatctgc ttcactcacg gacagaaaga ctgtttagag tgctttcccg       2040
tgtcagaatc tcaacccgtt tctgtcgtca aaaaggcgta tcagaaactg tgctacattc       2100
atcatatcat gggaaaggtg ccagacgctt gcactgcctg cgatctggtc aatgtggatt       2160
tggatgactg catctttgaa caataaatga tttaaatcag gtatggctgc cgatggttat       2220
cttccagatt ggctcgagga cactctctct gaaggaataa gacagtggtg gaagctcaaa       2280
cctggcccac caccaccaaa gcccgcgagg cggcataagg acgacagcag gggtcttgtg       2340
cttcctgggt acaagtacct cggacccttc aacggactcg acaagggaga gccggtcaac       2400
gaggcagacg ccgcggccct cgagcacgta caaagcctac gaccggcagc tcgacagcgg       2460
agacaacccg tacctcaagt acaaccacgc cgacgcggag tttcaggagc gccttaaaga       2520
agatacgtct tttgggggca acctcggacg agcagtcttc caggcgaaaa agagggttct       2580
tgaacctctg ggcctggttg aggaacctgt taagacggct ccgggaaaaa agaggccggt       2640
agagcactct cctgtggagc cagactcctc ctcgggaacc ggaaaggcgg gccagcagcc       2700
tgcaagaaaa agattgaatt ttggtcagac tggagacgca gactcagtac ctgacccca        2760 gcctctcgga cagccaccag cagccccctc tggtctggga actaatacga tggctacagg       2820
cagtggcgca ccaatggcag acaataacga gggcgccgac ggagtgggta attcctccgg       2880
aaattggcat tgcgattcca catggatggg cgacagagtc atcaccacca gcacccgaac       2940
ctgggccctg cccacctaca caaccacct ctacaaacaa atttccagcc aatcaggagc        3000
ctcgaacgac aatcactact ttggctacag caccccttgg gggtattttg acttcaacag       3060
attccactgc cacttttcac cacgtgactg gcaaagactc atcaacaaca actgggggatt      3120 ccgacccaag agactcaact tcaagctctt taacattcaa gtcaaagagg tcacgcagaa       3180
tgacggtacg acgacgattg ccaataacct taccagcacg gttcaggtgt ttactgactc       3240
ggagtaccag ctcccgtacg tcctcggctc ggcgcatcaa ggatgcctcc cgccgttccc       3300
agcagacgtc ttcatggtgc acagtatgg ataccctcacc ctgaacaacg ggagtcaggc      3360
agtaggacgc tcttcatttt actgcctgga gtactttcct tctcagatgc tgcgtaccgg       3420
aaacaacttt accttcagct acactttga ggacgttcct ttccacagca gctacgctca        3480
cagccagagt ctgaccgtc tcatgaatcc tctcatcgac cagtacctgt attacttgag        3540
cagaacaaac actccaagtg gaaccaccac gcagtcaagg cttcagtttt ctcaggccgg       3600
```

-continued

| | |
|---|---|
| agcgagtgac attcgggacc agtctaggaa ctggcttcct ggaccctgtt accgccagca | 3660 |
| gcgagtatca aagacatctg cggataacaa caacagtgaa tactcgtgga ctggagctac | 3720 |
| caagtaccac ctcaatggca gagactctct ggtgaatccg gccatggcaa gccacaagga | 3780 |
| cgatgaagaa aagtttttc ctcagagcgg ggttctcatc tttgggaagc aaggctcaga | 3840 |
| gaaaacaaat gtgaacattg aaaaggtcat gattacagac gaagaggaaa tcggaacaac | 3900 |
| caatcccgtg ctacggagc agtatggttc tgtatctacc aacctccaga gaggcaacag | 3960 |
| acaagcagct accgcagatg tcaacacaca aggcgttctt ccaggcatgg tctggcagga | 4020 |
| cagagatgtg taccttcagg ggcccatctg ggcaaagatt ccacacacgg acggacattt | 4080 |
| tcaccctct cccctcatgg gtggattcgg acttaaacac cctcctccac agattctcat | 4140 |
| caagaacacc ccgtacctg cgaatccttc gaccaccttc agtgcggcaa agtttgcttc | 4200 |
| cttcatcaca cagtactcca cgggacacgg tcagcgtgga gatcgagtgg gagctgcaga | 4260 |
| aggaaaacag caaacgctgg aatcccgaaa ttcagtacac ttccaactac aacaagtctg | 4320 |
| ttaatcgtgg acttaccgtg gatactaatg gcgtgtattc agagcctcgc cccattggca | 4380 |
| ccagatacct gactcgtaat ctgtaattgc ttgttaatca ataaaccgtt taattcgttt | 4440 |
| cagttgaact ttggtctctg cgtatttctt tcttatctag tttccatggc tacgtagata | 4500 |
| agtagcatgg cgggttaatc attaactaca aggaacccct agtgatggag ttggccactc | 4560 |
| cctctctgcg cgctcgctcg ctcactgagg ccgggcgacc aaaggtcgcc cgacgcccgg | 4620 |
| gctttgcccg gcggcctca gtgagcgagc gagcgcgcag agagggagtg gccaa | 4675 |

<210> SEQ ID NO 2
<211> LENGTH: 4718
<212> TYPE: DNA
<213> ORGANISM: Adeno-associated virus serotype 1

<400> SEQUENCE: 2

| | |
|---|---|
| ttgcccactc cctctctgcg cgctcgctcg ctcggtgggg cctgcggacc aaaggtccgc | 60 |
| agacggcaga gctctgctct gccggcccca ccgagcgagc gagcgcgcag agagggagtg | 120 |
| ggcaactcca tcactagggg taatcgcgaa gcgcctccca cgctgccgcg tcagcgctga | 180 |
| cgtaaattac gtcataggg agtggtcctg tattagctgt cacgtgagtg cttttgcgac | 240 |
| attttgcgac accacgtggc catttagggt atatatggcc gagtgagcga gcaggatctc | 300 |
| cattttgacc gcgaaatttg aacgagcagc agccatgccg ggcttctacg agatcgtgat | 360 |
| caaggtgccg agcgacctgg acgagcacct gccgggcatt tctgactcgt ttgtgagctg | 420 |
| ggtggccgag aaggaatggg agctgccccc ggattctgac atggatctga atctgattga | 480 |
| gcaggcaccc ctgaccgtgg ccgagaagct gcagcgcgac ttcctggtcc aatggcgccg | 540 |
| cgtgagtaag gccccggagg ccctcttctt tgttcagttc gagaagggcg agtcctactt | 600 |
| ccacctccat attctggtgg agaccacggg ggtcaaatcc atggtgctgg ccgcttcct | 660 |
| gagtcagatt agggacaagc tggtgcagac catctaccgc gggatcgagc cgaccctgcc | 720 |
| caactggttc gcggtgacca agacgcgtaa tggcgccgga gggggaaca aggtggtgga | 780 |
| cgagtgctac atccccaact acctcctgcc caagactcag cccgagctgc agtgggcgtg | 840 |
| gactaacatg gaggagtata taagcgcctg tttgaacctg gccgagcgca acggctcgt | 900 |
| ggcgcagcac ctgacccacg tcagccagac ccaggagcag aacaaggaga atctgaaccc | 960 |
| caattctgac gcgcctgtca tccggtcaaa aacctccgcg cgctacatgg agctggtcgg | 1020 |
| gtggctggtg gaccggggca tcacctccga gaagcagtgg atccaggagg accaggcctc | 1080 |

```
gtacatctcc ttcaacgccg cttccaactc gcggtcccag atcaaggccg ctctggacaa    1140
tgccggcaag atcatggcgc tgaccaaatc cgcgcccgac tacctggtag cccccgctcc    1200
gcccgcggac attaaaacca accgcatcta ccgcatcctg gagctgaacg gctacgaacc    1260
tgcctacgcc ggctccgtct ttctcggctg gcccagaaa aggttcggga agcgcaacac     1320
catctggctg tttgggccgg ccaccacggg caagaccaac atcgcggaag ccatcgccca    1380
cgccgtgccc ttctacggct gcgtcaactg gaccaatgag aactttccct tcaatgattg    1440
cgtcgacaag atggtgatct ggtgggagga gggcaagatg acggccaagg tcgtggagtc    1500
cgccaaggcc attctcggcg gcagcaaggt gcgcgtggac caaaagtgca agtcgtccgc    1560
ccagatcgac cccaccccg tgatcgtcac ctccaacacc aacatgtgcg ccgtgattga     1620
cgggaacagc accaccttcg agcaccagca gccgttgcag gaccggatgt tcaaatttga    1680
actcacccgc cgtctggagc atgactttgg caaggtgaca aagcaggaag tcaaagagtt    1740
cttccgctgg gcgcaggatc acgtgaccga ggtggcgcat gagttctacg tcagaaaggg    1800
tggagccaac aaaagacccg cccccgatga cgcggataaa agcgagccca gcgggcctg    1860 cccctcagtc gcggatccat cgacgtcaga cgcggaagga gctccggtgg actttgccga    1920
caggtaccaa aacaaatgtt ctcgtcacgc gggcatgctt cagatgctgt ttccctgcaa    1980
gacatgcgag agaatgaatc agaatttcaa catttgcttc acgcacggga cgagagactg    2040
ttcagagtgc ttccccggcg tgtcagaatc tcaaccggtc gtcagaaaga ggacgtatcg    2100
gaaactctgt gccattcatc atctgctggg gcgggctccc gagattgctt gctcggcctg    2160
cgatctggtc aacgtggacc tggatgactg tgtttctgag caataaatga cttaaaccag    2220
gtatggctgc cgatggttat cttccagatt ggctcgagga caacctctct gagggcattc    2280
gcgagtggtg ggacttgaaa cctggagccc cgaagcccaa agccaaccag caaaagcagg    2340
acgacggccg gggtctggtg cttcctggct acaagtacct cggacccttc aacggactcg    2400 acaagggga gcccgtcaac gcggcggacg cagcggccct cgagcacgac aaggcctacg    2460
accagcagct caaagcgggt gacaatccgt acctgcggta taccacgcc gacgccgagt     2520 ttcaggagcg tctgcaagaa gatacgtctt ttggggcaa cctcgggcga gcagtcttcc    2580
aggccaagaa gcgggttctc gaacctctcg gtctggttga ggaaggcgct aagacggctc    2640
ctggaaagaa acgtccggta gagcagtcgc cacaagagcc agactcctcc tcgggcatcg    2700
gcaagacagg ccagcagccc gctaaaaaga gactcaattt tggtcagact ggcgactcag    2760
agtcagtccc cgatccacaa cctctcggag aacctccagc accccccgct gctgtgggac    2820
ctactacaat ggcttcaggc ggtggcgcac caatggcaga caataacgaa ggcgccgacg    2880
gagtgggtaa tgcctcagga aattggcatt gcgattccac atggctgggc gacagagtca    2940
tcaccaccag caccgcacc tgggccttgc ccacctacaa taaccacctc tacaagcaaa    3000
tctccagtgc ttcaacgggg gccagcaacg acaaccacta cttcggctac agcacccct    3060 gggggtattt tgatttcaac agattccact gccacttttc accacgtgac tggcagcgac    3120
tcatcaacaa caattgggga ttccggccca agagactcaa cttcaaactc ttcaacatcc    3180
aagtcaagga ggtcacgacg aatgatgcg tcacaaccat cgctaataac cttaccagca    3240
cggttcaagt cttctcggac tcggagtacc agcttccgta cgtcctcggc tctgcgcacc    3300
agggctgcct ccctccgttc ccggcggacg tgttcatgat tccgcaatac ggctacctga    3360
cgctcaacaa tggcagccaa gccgtgggac gttcatcctt ttactgcctg gaatatttcc    3420
```

-continued

```
cttctcagat gctgagaacg ggcaacaact ttaccttcag ctacacctttt gaggaagtgc    3480
ctttccacag cagctacgcg cacagccaga gcctggaccg gctgatgaat cctctcatcg    3540
accaatacct gtattacctg aacagaactc aaaatcagtc cggaagtgcc caaaacaagg    3600
acttgctgtt tagccgtggg tctccagctg gcatgtctgt tcagcccaaa aactggctac    3660
ctggaccctg ttatcggcag cagcgcgttt ctaaaacaaa aacagacaac aacaacagca    3720
attttacctg gactggtgct tcaaaatata acctcaatgg cgtgaatccc atcatcaacc    3780
ctggcactgc tatggcctca cacaaagacg acgaagacaa gttctttccc atgagcggtg    3840
tcatgatttt tggaaaagag agcgccggag cttcaaacac tgcattggac aatgtcatga    3900
ttacagacga agaggaaatt aaagccacta accctgtggc caccgaaaga tttgggaccg    3960
tggcagtcaa tttccagagc agcagcacag accctgcgac cggagatgtg catgctatgg    4020
gagcattacc tggcatggtg tggcaagata gagacgtgta cctgcagggt cccatttggg    4080
ccaaaattcc tcacacagat ggacactttc acccgtctcc tcttatgggc ggctttggac    4140
tcaagaaccc gcctcctcag atcctcatca aaaacacgcc tgttcctgcg aatcctccgg    4200
cggagttttc agctacaaag tttgcttcat tcatcaccca atactccaca ggacaagtga    4260
gtgtggaaat tgaatgggag ctgcagaaag aaaacagcaa gcgctggaat cccgaagtgc    4320
agtacacatc caattatgca aaatctgcca cgttgatttt actgtggac aacaatggac    4380
tttatactga gcctcgcccc attggcaccc gttaccttac ccgtccctg taattacgtg    4440
ttaatcaata aaccggttga ttcgtttcag ttgaactttg gtctcctgtc cttcttatct    4500
tatcggttac catggttata gcttacacat taactgcttg gttgcgcttc gcgataaaag    4560
acttacgtca tcgggttacc cctagtgatg gagttgccca ctccctctct gcgcgctcgc    4620
tcgctcggtg gggcctgcgg accaaaggtc cgcagacggc agagctctgc tctgccggcc    4680
ccaccgagcg agcgagcgcg cagagaggga gtgggcaa                           4718
```

<210> SEQ ID NO 3
<211> LENGTH: 4726
<212> TYPE: DNA
<213> ORGANISM: Adeno-associated virus serotype 3

<400> SEQUENCE: 3

```
ttggccactc cctctatgcg cactcgctcg ctcggtgggg cctggcgacc aaaggtcgcc      60
agacggacgt gctttgcacg tccggcccca ccgagcgagc gagtgcgcat agagggagtg     120
gccaactcca tcactagagg tatggcagtg acgtaacgcg aagcgcgcga agcgagacca     180
cgcctaccag ctgcgtcagc agtcaggtga ccctttttgcg acagtttgcg acaccacgtg     240
gccgctgagg gtatatattc tcgagtgagc gaaccaggag ctccattttg accgcgaaat     300
ttgaacgagc agcagccatg ccggggttct acgagattgt cctgaaggtc ccgagtgacc     360
tggacgagcg cctgccgggc atttctaact cgtttgttaa ctgggtggcc gagaaggaat     420
gggacgtgcc gccggattct gacatggatc cgaatctgat tgagcaggca cccctgaccg     480
tggccgaaaa gcttcagcgc gagttcctgg tggagtggcg ccgcgtgagt aaggcccccgg     540
aggccctctt ttttgtccag ttcgaaaagg gggagaccta cttccacctg cacgtgctga     600
ttgagaccat cggggtcaaa tccatggtgg tcggccgcta cgtgagccag attaaagaga     660
agctggtgac ccgcatctac cgcggggtcg agccgcagct tccgaactgg ttcgcggtga     720
ccaaaacgcg aaatgcgcc ggggggcggga acaaggtggt ggacgactgc tacatccccca     780
actacctgct ccccaagacc cagcccgagc tccagtgggc gtggactaac atggaccagt     840
```

```
atttaagcgc ctgtttgaat ctcgcggagc gtaaacggct ggtggcgcag catctgacgc      900
acgtgtcgca gacgcaggag cagaacaaag agaatcagaa ccccaattct gacgcgccgg      960
tcatcaggtc aaaaacctca gccaggtaca tggagctggt cgggtggctg gtggaccgcg     1020
ggatcacgtc agaaaagcaa tggattcagg aggaccaggc tcgtacatc tccttcaacg      1080
ccgcctccaa ctcgcggtcc cagatcaagg ccgcgctgga caatgcctcc aagatcatga     1140
gcctgacaaa gacggctccg gactacctgg tgggcagcaa cccgccggag acattacca      1200
aaaatcggat ctaccaaatc ctggagctga cgggtacga tccgcagtac gcggcctccg      1260
tcttcctggg ctgggcgcaa aagaagttcg ggaagaggaa caccatctgg ctctttgggc     1320
cggccacgac gggtaaaacc aacatcgcgg aagccatcgc ccacgccgtg cccttctacg     1380
gctgcgtaaa ctggaccaat gagaactttc ccttcaacga ttgcgtcgac aagatggtga     1440
tctggtggga ggagggcaag atgacggcca aggtcgtgga gagcgccaag gccattctgg     1500
gcggaagcaa ggtgcgcgtg gaccaaaagt gcaagtcatc ggcccagatc gaaccccactc    1560
ccgtgatcgt cacctccaac accaacatgt gcgccgtgat tgacgggaac agcaccacct     1620
tcgagcatca gcgccgctg caggaccgga tgtttgaatt tgaacttacc cgccgtttgg      1680
accatgactt tgggaaggtc accaaacagg aagtaaagga ctttttccgg tgggcttccg     1740
atcacgtgac tgacgtggct catgagttct acgtcagaaa gggtgagct aagaaacgcc      1800
ccgcctccaa tgacgcggat gtaagcgagc caaaacggga gtgcacgtca cttgcgcagc     1860
cgacaacgtc agacgcggaa gcaccggcgg actacgcgga caggtaccaa aacaaatgtt     1920
ctcgtcacgt gggcatgaat ctgatgcttt ttccctgtaa acatgcgag agaatgaatc      1980
aaatttccaa tgtctgttt acgcatggtc aaagagactg tggggaatgc ttccctggaa     2040
tgtcagaatc tcaacccgtt tctgtcgtca aaaagaagac ttatcagaaa ctgtgtccaa     2100
ttcatcatat cctgggaagg gcacccgaga ttgcctgttc ggcctgcgat ttggccaatg     2160
tggacttgga tgactgtgtt tctgagcaat aaatgactta aaccaggtat ggctgctgac     2220
ggttatcttc cagattggct cgaggacaac ctttctgaag gcattcgtga gtggtgggct    2280
ctgaaacctg gagtccctca acccaaagcg aaccaacaac accaggacaa ccgtcggggt    2340
cttgtgcttc cgggttacaa atacctcgga cccggtaacg gactcgacaa aggagagccg    2400
gtcaacgagg cggacgcggc agccctcgaa cacgacaaag cttacgacca gcagctcaag    2460
gccggtgaca acccgtacct caagtacaac cacgccgacg ccgagtttca ggagcgtctt    2520
caagaagata cgtctttgg gggcaacctt ggcagagcag tcttccaggc caaaaagagg     2580
atccttgagc ctcttggtct ggttgaggaa gcagctaaaa cggctcctgg aaagaagggg    2640
gctgtagatc agtctcctca ggaaccggac tcatcatctg tgttggcaa atcgggcaaa     2700
cagcctgcca gaaaaagact aaatttcggt cagactggag actcagagtc agtcccagac    2760
cctcaacctc tcggagaacc accagcagcc cccacaagtt tgggatctaa tacaatggct    2820
tcaggcggtg gcgcaccaat ggcagacaat aacgagggtg ccgatggagt gggtaattcc    2880
tcaggaaatt ggcattgcga ttcccaatgg ctgggcgaca gagtcatcac caccagcacc    2940
agaacctggg ccctgcccac ttacaacaac catctctaca gcaaatctc cagccaatca    3000
ggagcttcaa acgacaacca ctactttggc tacagcaccc cttgggggta ttttgacttt    3060
aacagattcc actgccactt ctcaccacgt gactggcagc gactcattaa caacaactgg    3120
ggattccggc ccaagaaact cagcttcaag ctcttcaaca tccaagttag aggggtcacg    3180
```

```
cagaacgatg gcacgacgac tattgccaat aaccttacca gcacggttca agtgtttacg    3240
gactcggagt atcagctccc gtacgtgctc gggtcggcgc accaaggctg tctcccgccg    3300
tttccagcgg acgtcttcat ggtccctcag tatggatacc tcaccctgaa caacggaagt    3360
caagcggtgg gacgctcatc cttttactgc ctggagtact tcccttcgca gatgctaagg    3420
actggaaata acttccaatt cagctatacc ttcgaggatg taccttttca cagcagctac    3480
gctcacagcc agagtttgga tcgcttgatg aatcctctta ttgatcagta tctgtactac    3540
ctgaacagaa cgcaaggaac aacctctgga acaaccaacc aatcacggct gcttttagc     3600 caggctgggc tcagtctat gtctttgcag gccagaaatt ggctacctgg gccctgctac     3660
cggcaacaga ctttcaaa gactgctaac gacaacaaca acagtaactt ccttggaca       3720 gcggccagca aatatcatct caatggccgc gactcgctgg tgaatccagg accagctatg    3780
gccagtcaca aggacgatga agaaaaattt ttccctatgc acggcaatct aatatttggc    3840
aaagaaggga caacggcaag taacgcagaa ttagataatg taatgattac ggatgaagaa    3900
gagattcgta ccaccaatcc tgtggcaaca gagcagtatg gaactgtggc aaataacttg    3960
cagagctcaa atacagctcc cacgactgga actgtcaatc atcaggggc cttacctggc    4020 atggtgtggc aagatcgtga cgtgtaccttcaaggaccta tctgggcaaa gattcctcac    4080
acggatggac actttcatcc ttctcctctg atgggaggct ttggactgaa acatccgcct    4140
cctcaaatca tgatcaaaaa tactccggta ccggcaaatc ctcgacgac tttcagcccg    4200 gccaagtttg cttcatttat cactcagtac tccactggac aggtcagcgt ggaaattgag    4260
tgggagctac agaagaaaa cagcaaacgt tggaatccag agattcagta cacttccaac    4320
tacaacaagt ctgttaatgt ggactttact gtagacacta atggtgttta tagtgaacct    4380
cgccctattg aacccggta tctcacacga aacttgtgaa tcctggttaa tcaataaacc    4440
gtttaattcg tttcagttga actttggctc ttgtgcactt ctttatcttt atcttgttc     4500 catggctact gcgtagataa gcagcggcct gcggcgcttg cgcttcgcgg tttacaactg    4560
ctggttaata tttaactctc gccataccctc tagtgatgga gttggccact ccctctatgc   4620
gcactcgctc gctcggtggg gcctggcgac caaaggtcgc cagacggacg tgcttttgcac   4680 gtccggcccc accgagcgag cgagtgcgca tagagggagt ggccaa                   4726
```

<210> SEQ ID NO 4
<211> LENGTH: 4767
<212> TYPE: DNA
<213> ORGANISM: Adeno-associated virus serotype 4

<400> SEQUENCE: 4

```
ttggccactc cctctatgcg cgctcgctca ctcactcggc cctggagacc aaaggtctcc      60
agactgccgg cctctggccg gcagggccga gtgagtgagc gagcgcgcat agagggagtg    120
gccaactcca tcatctaggt ttgcccactg acgtcaatgt gacgtcctag ggttagggag    180
gtccctgtat tagcagtcac gtgagtgtcg tatttcgcgg agcgtagcgg agcgcatacc    240
aagctgccac gtcacagcca cgtggtccgt ttgcgacagt ttgcgacacc atgtggtcag    300
gagggtatat aaccgcgagt gagccagcga ggagctccat tttgccccgcg aattttgaac    360 gagcagcagc catgccgggg ttctacgaga tcgtgctgaa ggtgcccagc gacctggacg   420
agcacctgcc cggcatttct gactcttttg tgagctgggt ggccgagaag gaatgggagc    480
tgccgccgga ttctgacatg gacttgaatc tgattgagca ggcacccctg accgtggccg    540
aaaagctgca acgcgagttc ctggtcgagt ggcgccgcgt gagtaaggcc ccggaggccc    600
```

```
tcttctttgt ccagttcgag aagggggaca gctacttcca cctgcacatc ctggtggaga      660
ccgtgggcgt caaatccatg gtggtgggcc gctacgtgag ccagattaaa gagaagctgg      720
tgacccgcat ctaccgcggg gtcgagccgc agcttccgaa ctggttcgcg gtgaccaaga      780
cgcgtaatgg cgccggaggc gggaacaagg tggtggacga ctgctacatc cccaactacc      840
tgctccccaa gacccagccc gagctccagt gggcgtggac taacatggac cagtatataa      900
gcgcctgttt gaatctcgcg gagcgtaaac ggctggtggc gcagcatctg acgcacgtgt      960
cgcagacgca ggagcagaac aaggaaaacc agaaccccaa ttctgacgcg ccggtcatca     1020
ggtcaaaaac ctccgccagg tacatggagc tggtcgggtg gctggtggac cgcgggatca     1080
cgtcagaaaa gcaatggatc caggaggacc aggcgtccta catctccttc aacgccgcct     1140
ccaactcgcg gtcacaaatc aaggccgcgc tggacaatgc ctccaaaatc atgagcctga     1200
caaagacggc tccggactac ctggtgggcc agaacccgcc ggaggacatt ccagcaacc      1260 gcatctaccg aatcctcgag atgaacgggt acgatccgca gtacgcggcc tccgtcttcc     1320
tgggctgggc gcaaaagaag ttcgggaaga ggaacaccat ctggctcttt gggccggcca     1380
cgacgggtaa aaccaacatc gcggaagcca tcgcccacgc cgtgcccttc tacgctgcg      1440 tgaactggac caatgagaac tttccgttca acgattgcgt cgacaagatg gtgatctggt     1500
gggaggaggg caagatgacg gccaaggtcg tagagagcgc caaggccatc ctgggcggaa     1560
gcaaggtgcg cgtggaccaa aagtgcaagt catcggccca gatcgaccca actcccgtga     1620
tcgtcacctc caacaccaac atgtgcgcgg tcatcgacgg aaactcgacc accttcgagc     1680
accaacaacc actccaggac cggatgttca agttcgagct caccaagcgc ctggagcacg     1740
actttggcaa ggtcaccaag caggaagtca aagactttt ccggtgggcg tcagatcacg     1800
tgaccgaggt gactcacgag ttttacgtca gaaagggtgg agctagaaag aggcccgccc     1860
ccaatgacgc agatataagt gagcccaagc gggcctgtcc gtcagttgcg cagccatcga     1920
cgtcagacgc ggaagctccg gtggactacg cggacaggta ccaaaacaaa tgttctcgtc     1980
acgtgggtat gaatctgatg cttttccct gccggcaatg cgagagaatg aatcagaatg     2040
tggacatttg cttcacgcac ggggtcatgg actgtgccga gtgcttcccc gtgtcagaat     2100
ctcaacccgt gtctgtcgtc agaaagcgga cgtatcagaa actgtgtccg attcatcaca     2160
tcatggggag ggcgcccgag gtggcctgct cggcctgcga actggccaat gtggacttgg     2220
atgactgtga catggaacaa taaatgactc aaaccagata tgactgacgg ttaccttcca     2280
gattggctag aggacaacct ctctgaaggc gttcgagagt ggtgggcgct gcaacctgga     2340
gcccctaaac ccaaggcaaa tcaacaacat caggacaacg ctcggggtct tgtgcttccg     2400
ggttacaaat acctcggacc cggcaacgga ctcgacaagg ggaacccgt caacgcagcg     2460 gacgcggcag ccctcgagca cgacaaggcc tacgaccagc agctcaaggc cggtgacaac     2520
ccctacctca gtacaaccca cgccgacgcg gagttccagc agcggcttca gggcgacaca     2580
tcgtttgggg gcaacctcgg cagagcagtc ttccaggcca aaagagggt tcttgaacct     2640 cttggtctgg ttgagcaagc gggtgagacg gctcctggaa agaagagacc gttgattgaa     2700 tcccccagc agcccgactc ctccacgggt atcggcaaaa aaggcaagca gccggctaaa     2760
aagaagctcg ttttcgaaga cgaaactgga gcaggcgacg gaccccctga gggatcaact     2820
tccggagcca tgtctgatga cagtgagatg cgtcagcag ctggcggagc tgcagtcgag     2880
ggcggacaag gtgccgatgg agtgggtaat gcctcgggtg attggcattg cgattccacc     2940
```

```
tggtctgagg gccacgtcac gaccaccagc accagaacct gggtcttgcc cacctacaac    3000
aaccacctct acaagcgact cggagagagc ctgcagtcca acacctacaa cggattctcc    3060
accccctggg gatactttga cttcaaccgc ttccactgcc acttctcacc acgtgactgg    3120
cagcgactca tcaacaacaa ctgggggcatg cgacccaaag ccatgcgggt caaaatcttc    3180
```

```
aacatccagg tcaaggaggt cacgacgtcg aacggcgaga caacggtggc taataacctt    3240
accagcacgg ttcagatctt tgcggactcg tcgtacgaac tgccgtacgt gatggatgcg    3300
ggtcaagagg gcagcctgcc tccttttccc aacgacgtct ttatggtgcc ccagtacggc    3360
tactgtggac tggtgaccgg caacacttcg cagcaacaga ctgacagaaa tgccttctac    3420
tgcctggagt actttccttc gcagatgctg cggactggca acaactttga aattacgtac    3480
agttttgaga aggtgccttt ccactcgatg tacgcgcaca ccagagcct ggaccggctg     3540 atgaaccctc tcatcgacca gtacctgtgg ggactgcaat cgaccaccac cggaaccacc    3600
ctgaatgccg ggactgccac caccaacttt accaagctgc ggcctaccaa cttttccaac    3660
tttaaaaaga actggctgcc cggggccttca atcaagcagc agggcttctc aaagactgcc    3720
aatcaaaact acaagatccc tgccaccggg tcagacagtc tcatcaaata cgagacgcac    3780
agcactctgg acggaagatg gagtgccctg acccccggac ctccaatggc cacggctgga    3840
cctgcggaca gcaagttcag caacagccag ctcatctttg cggggcctaa acagaacggc    3900
aacacggcca ccgtacccgg gactctgatc ttcacctctg aggaggagct ggcagccacc    3960
aacgccaccg atacggacat gtggggcaac ctacctggcg gtgaccagag caacagcaac    4020
ctgccgaccg tggacagact gacagccttg ggagccgtgc tggaatggt ctggcaaaac    4080 agagacattt actaccaggg tcccatttgg gccaagattc tcataccga tggacacttt    4140 cacccctcac cgctgattgg tgggtttggg ctgaaacacc cgcctcctca aatttttatc    4200
aagaacaccc cggtacctgc gaatcctgca acgaccttca gctctactcc ggtaaactcc    4260
ttcattactc agtacagcac tggccaggtg tcggtcagaa ttgactggga gatccagaag    4320
gagcggtcca acgctggaaa ccccgaggtc cagtttacct ccaactacgg acagcaaaac    4380
tctctgttgt gggctcccga tgcggctggg aaatacactg agcctagggc tatcggtacc    4440
cgctacctca cccaccacct gtaataacct gttaatcaat aaaccggttt attcgtttca    4500
gttgaacttt ggtctccgtg tccttcttat cttatctcgt ttccatggct actgcgtaca    4560
taagcagcgg cctgcggcgc ttgcgcttcg cggtttacaa ctgccggtta atcagtaact    4620
tctggcaaac cagatgatgg agttggccac attagctatg cgcgtcgct cactcactcg    4680 gccctggaga ccaaaggtct ccagactgcc ggcctctggc cggcagggcc gagtgagtga    4740
gcgagcgcgc atagagggag tggccaa                                        4767
```

<210> SEQ ID NO 5
<211> LENGTH: 4642
<212> TYPE: DNA
<213> ORGANISM: Adeno-associated virus serotype 5

<400> SEQUENCE: 5

```
ctctccccccc tgtcgcgttc gctcgctcgc tggctcgttt gggggggtgg cagctcaaag     60
agctgccaga cgacggccct ctggccgtcg ccccccaaa cgagccagcg agcgagcgaa     120
cgcgacaggg gggagagtgc cacactctca agcaggggg ttttgtaagc agtgatgtca     180
taatgatgta atgcttattg tcacgcgata gttaatgatt aacagtcatg tgatgtgttt    240
tatccaatag gaagaaagcg cgcgtatgag ttctcgcgag acttccgggg tataaaagac    300
```

```
cgagtgaacg agcccgccgc cattctttgc tctggactgc tagaggaccc tcgctgccat    360
ggctaccttc tatgaagtca ttgttcgcgt cccatttgac gtggaggaac atctgcctgg    420
aatttctgac agctttgtgg actgggtaac tggtcaaatt tgggagctgc ctccagagtc    480
agatttaaat ttgactctgg ttgaacagcc tcagttgacg gtggctgata gaattcgccg    540
cgtgttcctg tacgagtgga acaaattttc caagcaggag tccaaattct tgtgcagtt    600 tgaaaaggga tctgaatatt ttcatctgca cacgcttgtg gagacctccg gcatctcttc    660
catggtcctc ggccgctacg tgagtcagat tcgcgcccag ctggtgaaag tggtcttcca    720
gggaattgaa ccccagatca acgactgggt cgccatcacc aaggtaaaga agggcggagc    780
caataaggtg gtggattctg gtatattcc cgcctacctg ctgccgaagg tccaaccgga    840
gcttcagtgg gcgtggacaa acctggacga gtataaattg gccgccctga atctggagga    900
gcgcaaacgg ctcgtcgcgc agtttctggc agaatcctcg cagcgctcgc aggaggcggc    960
ttcgcagcgt gagttctcgg ctgacccggt catcaaaagc aagacttccc agaaatacat   1020
ggcgctcgtc aactggctcg tggagcacgg catcacttcc gagaagcagt ggatccagga   1080
aaatcaggag agctacctct ccttcaactc caccggcaac tctcggagcc agatcaaggc   1140
cgcgctcgac aacgcgacca aaattatgag tctgacaaaa agcgcggtgg actacctcgt   1200
ggggagctcc gttcccgagg acatttcaaa aaacagaatc tggcaaattt ttgagatgaa   1260
tggctacgac ccggcctacg cgggatccat cctctacggc tggtgtcagc gctccttcaa   1320
caagaggaac accgtctggc tctacggacc cgccacgacc ggcaagacca acatcgcgga   1380
ggccatcgcc cacactgtgc ccttttacgg ctgcgtgaac tggaccaatg aaaactttcc   1440
ctttaatgac tgtgtggaca aaatgctcat ttggtgggag gagggaaaga tgaccaacaa   1500
ggtggttgaa tccgccaagg ccatcctggg gggctcaaag gtgcgggtcg atcagaaatg   1560
taaatcctct gttcaaattg attctacccc tgtcattgta acttccaata caaacatgtg   1620
tgtggtggtg gatgggaatt ccacgacctt tgaacaccag cagccgctgg aggaccgcat   1680
gttcaaattt gaactgacta gcggctccc gccagatttt ggcaagatta ctaagcagga   1740
agtcaaggac tttttttgctt gggcaaaggt caatcaggtg ccggtgactc acgagtttaa   1800
agttcccagg gaattggcgg gaactaaagg ggcggagaaa tctctaaaac gcccactggg   1860
tgacgtcacc aatactagct ataaaagtct ggagaagcgg gccaggctct catttgttcc   1920
cgagacgcct cgcagttcag acgtgactgt tgatcccgct cctctgcgac cgctcaattg   1980
gaattcaagg tatgattgca aatgtgacta tcatgctcaa tttgacaaca tttctaacaa   2040
atgtgatgaa tgtgaatatt tgaatcgggg caaaaatgga tgtatctgtc acaatgtaac   2100
tcactgtcaa atttgtcatg ggattccccc ctgggaaaag gaaaacttgt cagatttgg   2160 ggattttgac gatgccaata agaacagta ataaagcga gtagtcatgt cttttgttga   2220
tcaccctcca gattggttgg aagaagttgg tgaaggtctt cgcgagtttt tgggccttga   2280
agcgggccca ccgaaaccaa acccaatca gcagcatcaa gatcaagccc gtggtcttgt   2340
gctgcctggt tataactatc tcggacccgg aaacggtctc gatcgaggag agcctgtcaa   2400
cagggcagac gaggtcgcgc gagagcacga catctcgtac aacgagcagc ttgaggcggg   2460
agacaacccc tacctcaagt acaaccacgc ggacgccgag tttcaggaga agctcgccga   2520
cgacacatcc ttcggggaa acctcggaaa ggcagtcttt caggccaaga aaagggttct   2580
cgaacctttt ggcctggttg aagagggtgc taagacggcc cctaccggaa agcggataga   2640
```

-continued

| | |
|---|---|
| cgaccacttt ccaaaaagaa agaaggctcg gaccgaagag gactccaagc cttccacctc | 2700 |
| gtcagacgcc gaagctggac ccagcggatc cagcagctg caaatcccag cccaaccagc | 2760 |
| ctcaagtttg ggagctgata caatgtctgc gggaggtggc ggcccattgg gcgacaataa | 2820 |
| ccaaggtgcc gatggagtgg gcaatgcctc gggagattgg cattgcgatt ccacgtggat | 2880 |
| gggggacaga gtcgtcacca agtccacccg aacctggtg ctgcccagct acaacaacca | 2940 |
| ccagtaccga gagatcaaaa gcggctccgt cgacggaagc aacgccaacg cctactttgg | 3000 |
| atacagcacc ccctgggggt actttgactt taaccgcttc cacagccact ggagccccg | 3060 |
| agactggcaa agactcatca acaactactg gggcttcaga ccccggtccc tcagagtcaa | 3120 |
| aatcttcaac attcaagtca aagaggtcac ggtgcaggac tccaccacca ccatcgccaa | 3180 |
| caacctcacc tccaccgtcc aagtgtttac ggacgacgac taccagctgc cctacgtcgt | 3240 |
| cggcaacggg accgagggat gcctgccggc cttccctccg caggtctttta cgctgccgca | 3300 |
| gtacggttac gcgacgctga accgcgacaa cacagaaaat cccaccgaga ggagcagctt | 3360 |
| cttctgccta gagtactttc ccagcaagat gctgagaacg ggcaacaact ttgagtttac | 3420 |
| ctacaacttt gaggaggtgc ccttccactc cagcttcgct cccagtcaga acctgttcaa | 3480 |
| gctggccaac ccgctggtgg accagtactt gtaccgcttc gtgagcacaa ataacactgg | 3540 |
| cggagtccag ttcaacaaga acctggccgg gagatacgcc aacacctaca aaaactggtt | 3600 |
| cccggggccc atgggccgaa cccagggctg gaacctgggc tccggggtca accgcgccag | 3660 |
| tgtcagcgcc ttcgccacga ccaataggat ggagctcgag ggcgcgagtt accaggtgcc | 3720 |
| cccgcagccg aacggcatga ccaacaacct ccagggcagc aacacctatg ccctggagaa | 3780 |
| cactatgatc ttcaacagcc agccggcgaa cccgggcacc accgccacgt acctcgaggg | 3840 |
| caacatgctc atcaccagcg agagcgagac gcagccggtg aaccgcgtgg cgtacaacgt | 3900 |
| cggcgggcag atggccacca acaaccagag ctccaccact gccccgcgcga ccggcacgta | 3960 |
| caacctccag gaaatcgtgc ccggcagcgt gtggatggag agggacgtgt acctccaagg | 4020 |
| acccatctgg gccaagatcc cagagacggg ggcgcacttt caccccctctc cggccatggg | 4080 |
| cggattcgga ctcaaacacc caccgccccat gatgctcatc aagaacacgc ctgtgcccgg | 4140 |
| aaatatcacc agcttctcgg acgtgcccgt cagcagcttc atcacccagt acagcaccgg | 4200 |
| gcaggtcacc gtggagatgg agtgggagct caagaaggaa aactccaaga ggtgaaccc | 4260 |
| agagatccag tacacaaaca actacaacga cccccagttt gtggactttg ccccggacag | 4320 |
| caccggggaa tacagaacca ccagacctat cggaacccga taccttaccc gaccccttta | 4380 |
| acccattcat gtcgcatacc ctcaataaac cgtgtattcg tgtcagtaaa atactgcctc | 4440 |
| ttgtggtcat tcaatgaata acagcttaca acatctacaa aacctccttg cttgagagtg | 4500 |
| tggcactctc cccctgtcg cgttcgctcg ctcgctggct cgtttggggg ggtggcagct | 4560 |
| caaagagctg ccagacgacg gccctctggc cgtcgccccc ccaaacgagc cagcgagcga | 4620 |
| gcgaacgcga caggggggag ag | 4642 |

<210> SEQ ID NO 6
<211> LENGTH: 4683
<212> TYPE: DNA
<213> ORGANISM: Adeno-associated virus serotype 6

<400> SEQUENCE: 6

| | |
|---|---|
| ttggccactc cctctctgcg cgctcgctcg ctcactgagg ccgggcgacc aaaggtcgcc | 60 |
| cgacgcccgg gctttgcccg ggcggcctca gtgagcgagc gagcgcgcag agagggagtg | 120 |

```
gccaactcca tcactagggg ttcctggagg ggtggagtcg tgacgtgaat tacgtcatag      180
ggttagggag gtcctgtatt agaggtcacg tgagtgtttt gcgacatttt gcgacaccat      240
gtggtcacgc tgggtattta agcccgagtg agcacgcagg gtctccattt tgaagcggga      300
ggtttgaacg cgcagcgcca tgccggggtt ttacgagatt gtgattaagg tccccagcga      360
ccttgacgag catctgcccg gcatttctga cagctttgtg aactgggtgg ccgagaagga      420
atgggagttg ccgccagatt ctgacatgga tctgaatctg attgagcagg caccctgac       480 cgtggccgag aagctgcagc gcgacttcct ggtccagtgg cgccgcgtga gtaaggcccc      540
ggaggccctc ttctttgttc agttcgagaa gggcgagtcc tacttccacc tccatattct      600
ggtggagacc acggggtca  atccatggt gctgggccgc ttcctgagtc agattaggga       660
caagctggtg cagaccatct accgcgggat cgagccgacc ctgcccaact ggttcgcggt      720
gaccaagacg cgtaatggcg ccggaggggg gaacaaggtg gtggacgagt gctacatccc      780
caactacctc ctgcccaaga ctcagcccga gctgcagtgg gcgtggacta acatggagga      840
gtatataagc gcgtgtttaa acctggccga gcgcaaacgg ctcgtggcgc acgacctgac      900
ccacgtcagc cagacccagg agcagaacaa ggagaatctg aaccccaatt ctgacgcgcc      960
tgtcatccgg tcaaaaacct ccgcacgcta catggagctg gtcgggtggc tggtggaccg     1020
gggcatcacc tccgagaagc agtggatcca ggaggaccag gcctcgtaca tctccttcaa     1080
cgccgcctcc aactcgcggt cccagatcaa ggccgctctg acaatgccg  gcaagatcat     1140 ggcgctgacc aaatccgcgc cgactacct  ggtaggcccc gctccgcccg ccgacattaa     1200
aaccaaccgc atttaccgca tcctggagct gaacggctac gaccctgcct acgccggctc     1260
cgtctttctc ggctgggccc agaaaaggtt cggaaaacgc aacaccatct ggctgtttgg     1320
gccggccacc acgggcaaga ccaacatcgc ggaagccatc gcccacgccg tgcccttcta     1380
cggctgcgtc aactgaccaa atgagaactt tcccttcaac gattgcgtcg acaagatggt     1440
gatctggtgg gaggagggca agatgacggc caaggtcgtg gagtccgcca aggccattct     1500
cggcggcagc aaggtgcgcg tggaccaaaa gtgcaagtcg tccgcccaga tcgatcccac     1560
ccccgtgatc gtcacctcca acaccaacat gtgcgccgtg attgacggga acagcaccac     1620
cttcgagcac cagcagccgt tgcaggaccg gatgttcaaa tttgaactca cccgccgtct     1680
ggagcatgac tttggcaagg tgacaaagca ggaagtcaaa gagttcttcc gctgggcgca     1740
ggatcacgtg accgaggtgg cgcatgagtt ctacgtcaga aagggtggag ccaacaagag     1800
acccgccccc gatgacgcgg ataaaagcga gcccaagcgg gcctgcccct cagtcgcgga     1860
tccatcgacg tcagacgcgg aaggagctcc ggtggacttt gccgacaggt accaaaacaa     1920
atgttctcgt cacgcgggca tgcttcagat gctgtttccc tgcaaaacat gcgagagaat     1980
gaatcagaat ttcaacattt gcttcacgca cgggaccaga gactgttcag aatgtttccc     2040
cggcgtgtca gaatctcaac cggtcgtcag aaagaggacg tatcggaaac tctgtgccat     2100
tcatcatctg ctggggcggg ctcccgagat tgcttgctcg gcctgcgatc tggtcaacgt     2160
ggatctggat gactgtgttt ctgagcaata aatgacttaa accaggtatg gctgccgatg     2220
gttatcttcc agattggctc gaggacaacc tctctgaggg cattcgcgag tggtgggact     2280
tgaaacctgg agccccgaaa cccaaagcca accagcaaaa gcaggacgac ggccggggtc     2340
tggtgcttcc tggctacaag tacctcgac  ccttcaacgg actcgacaag ggggagcccg     2400
tcaacgcggc ggatgcagcg gccctcgagc acgacaaggc ctacgaccag cagctcaaag     2460
```

```
cgggtgacaa tccgtacctg cggtataacc acgccgacgc cgagtttcag gagcgtctgc    2520
aagaagatac gtcttttggg ggcaacctcg ggcgagcagt cttccaggcc aagaagaggg    2580
ttctcgaacc ttttggtctg gttgaggaag gtgctaagac ggctcctgga agaaacgtc    2640
cggtagagca gtcgccacaa gagccagact cctcctcggg cattggcaag acaggccagc    2700
agcccgctaa aaagagactc aattttggtc agactggcga ctcagagtca gtccccgacc    2760
cacaacctct cggagaacct ccagcaaccc ccgctgctgt gggacctact acaatggctt    2820
caggcggtgg cgcaccaatg gcagacaata acgaaggcgc cgacggagtg ggtaatgcct    2880
caggaaattg gcattgcgat tccacatggc tgggcgacag agtcatcacc accagcaccc    2940
gaacatgggc cttgcccacc tataacaacc acctctacaa gcaaatctcc agtgcttcaa    3000
cgggggccag caacgacaac cactacttcg gctacagcac ccctgggggg tattttgatt    3060
tcaacagatt ccactgccat ttctcaccac gtgactggca gcgactcatc aacaacaatt    3120
ggggattccg gcccaagaga ctcaacttca agctcttcaa catccaagtc aaggaggtca    3180
cgacgaatga tggcgtcacg accatcgcta ataaccttac cagcacggtt caagtcttct    3240
cggactcgga gtaccagttg ccgtacgtcc tcggctctgc gcaccagggc tgcctccctc    3300
cgttcccggc ggacgtgttc atgattccgc agtacggcta cctaacgctc aacaatggca    3360
gccaggcagt gggacggtca tcctttact gcctggaata tttcccatcg cagatgctga    3420
gaacgggcaa taactttacc ttcagctaca ccttcgagga cgtgcctttc cacagcagct    3480
acgcgcacag ccagagcctg accggctga tgaatcctct catcgaccag tacctgtatt    3540
acctgaacag aactcagaat cagtccggaa gtgcccaaaa caaggacttg ctgtttagcc    3600
gggggtctcc agctggcatg tctgttcagc ccaaaaactg gctacctgga ccctgttacc    3660
ggcagcagcg cgtttctaaa acaaaaacag acaacaacaa cagcaacttt acctggactg    3720
gtgcttcaaa atataacctt aatgggcgtg aatctataat caaccctggc actgctatgg    3780
cctcacacaa agacgacaaa gacaagttct ttcccatgag cggtgtcatg atttttggaa    3840
aggagagcgc cggagcttca aacactgcat tggacaatgt catgatcaca gacgaagagg    3900
aaatcaaagc cactaacccc gtggccaccg aaagatttgg gactgtggca gtcaatctcc    3960
agagcagcag cacagaccct gcgaccggag atgtgcatgt tatgggagcc ttacctggaa    4020
tggtgtggca agacagagac gtatacctgc agggtcctat ttgggccaaa attcctcaca    4080
cggatggaca ctttcacccg tctcctctca tgggcggctt tggacttaag cacccgcctc    4140
ctcagatcct catcaaaaac acgcctgttc ctgcgaatcc tccggcagag ttttcggcta    4200
caaagtttgc ttcattcatc acccagtatt ccacaggaca agtgagcgtg gagattgaat    4260
gggagctgca gaaagaaaac agcaaacgct ggaatcccga agtgcagtat acatctaact    4320
atgcaaaatc tgccaacgtt gatttcactg tggacaacaa tggactttat actgagcctc    4380
gccccattgg caccgttac ctcacccgtc cctgtaatt gtgtgttaat caataaaccg    4440
gttaattcgt gtcagttgaa ctttggtctc atgtcgttat tatcttatct ggtcaccata    4500
gcaaccggtt acacattaac tgcttagttg cgcttcgcga ataccctag tgatggagtt    4560
gcccactccc tctatgcgcg ctcgctcgct cggtggggcc ggcagagcag agctctgccg    4620
tctgcggacc tttggtccgc aggccccacc gagcgagcga gcgcgcatag agggagtggg    4680
caa                                                                4683

<210> SEQ ID NO 7
<211> LENGTH: 4721
```

<212> TYPE: DNA
<213> ORGANISM: Adeno-associated virus serotype 7

<400> SEQUENCE: 7

```
ttggccactc cctctatgcg cgctcgctcg ctcggtgggg cctgcggacc aaaggtccgc      60
agacggcaga gctctgctct gccggcccca ccgagcgagc gagcgcgcat agagggagtg     120
gccaactcca tcactagggg taccgcgaag cgcctccac  gctgccgcgt cagcgctgac     180
gtaaatcacg tcataggga  gtggtcctgt attagctgtc acgtgagtgc ttttgcgaca     240
ttttgcgaca ccacgtggcc atttgaggta tatatggccg agtgagcgag caggatctcc     300
attttgaccg cgaaatttga acgagcagca gccatgccgg gtttctacga gatcgtgatc     360
aaggtgccga gcgacctgga cgagcacctg ccgggcattt ctgactcgtt tgtgaactgg     420
gtggccgaga aggaatggga gctgcccccg gattctgaca tggatctgaa tctgatcgag     480
caggcacccc tgaccgtggc cgagaagctg cagcgcgact tcctggtcca atggcgccgc     540
gtgagtaagg ccccggaggc cctgttcttt gttcagttcg agaagggcga gagctacttc     600
caccttcacg ttctggtgga gaccacgggg gtcaagtcca tggtgctagg ccgcttcctg     660
agtcagattc gggagaagct ggtccagacc atctaccgcg gggtcgagcc cacgctgccc     720
aactggttcg cggtgaccaa gacgcgtaat ggcgccggcg gggggaacaa ggtggtggac     780
gagtgctaca tccccaacta cctcctgccc aagacccagc cgagctgca  gtgggcgtgg     840
actaacatgg aggagtatat aagcgcgtgt ttgaacctgg ccgaacgcaa acggctcgtg     900
gcgcagcacc tgacccacgt cagccagacg caggagcaga acaaggagaa tctgaacccc     960
aattctgacg cgcccgtgat caggtcaaaa acctccgcgc gctacatgga gctggtcggg    1020
tggctggtgg accggggcat cacctccgag aagcagtgga tccaggagga ccaggcctcg    1080
tacatctcct tcaacgccgc ctccaactcg cggtcccaga tcaaggccgc gctggacaat    1140
gccggcaaga tcatggcgct gaccaaatcc gcgcccgact acctggtggg gccctcgctg    1200
cccgcggaca ttaaaaccaa ccgcatctac cgcatcctgg agctgaacgg gtacgatcct    1260
gcctacgccg gctccgtctt tctcggctgg gcccagaaaa agttcgggaa gcgcaacacc    1320
atctggctgt ttgggcccgc caccaccggc aagaccaaca ttgcggaagc catcgcccac    1380
gccgtgccct tctacggctg cgtcaactgg accaatgaga actttccctt caacgattgc    1440
gtcgacaaga tggtgatctg gtgggaggag gcaagatga  cggccaaggt cgtggagtcc    1500
gccaaggcca ttctcggcgg cagcaaggtg cgcgtggacc aaaagtgcaa gtcgtccgcc    1560
cagatcgacc ccaccccgt  gatcgtcacc tccaacacca catgtgcgc  cgtgattgac    1620
gggaacagca ccaccttcga gcaccagcag ccgttgcagg accggatgtt caaatttgaa    1680
ctcacccgcc gtctggagca cgactttggc aaggtgacga gcaggaagt  caaagagttc    1740
ttccgctggg ccagtgatca cgtgaccgag gtggcgcatg agttctacgt cagaaagggc    1800
ggagccagca aaagacccgc ccccgatgac gcggatataa gcgagcccaa gcgggcctgc    1860
ccctcagtcg cggatccatc gacgtcagac gcggaaggag ctccggtgga ctttgccgac    1920
aggtaccaaa acaaatgttc tcgtcacgcg gcatgattc  agatgctgtt tccctgcaaa    1980
acgtgcgaga gaatgaatca gaatttcaac atttgcttca cacacggggt cagagactgt    2040
ttagagtgtt tccccggcgt gtcagaatct caaccggtcg tcagaaaaaa gacgtatcgg    2100
aaactctgcg cgattcatca tctgctgggg cgggcgcccg agattgcttg ctcggcctgc    2160
gacctggtca acgtggacct ggacgactgc gtttctgagc aataaatgac ttaaaccagg    2220
```

```
tatggctgcc gatggttatc ttccagattg gctcgaggac aacctctctg agggcattcg    2280
cgagtggtgg gacctgaaac ctggagcccc gaaacccaaa gccaaccagc aaaagcagga    2340
caacggccgg ggtctggtgc ttcctggcta caagtacctc ggacccttca acggactcga    2400
caagggggag cccgtcaacg cggcggacgc agcggccctc gagcacgaca aggcctacga    2460
ccagcagctc aaagcgggtg acaatccgta cctgcggtat aaccacgccg acgccgagtt    2520
tcaggagcgt ctgcaagaag atacgtcatt tgggggcaac ctcgggcgag cagtcttcca    2580
ggccaagaag cgggttctcg aacctctcgg tctggttgag aaggcgcta agacggctcc     2640 tgcaaagaag agaccggtag agccgtcacc tcagcgttcc cccgactcct ccacgggcat    2700
cggcaagaaa ggccagcagc ccgccagaaa gagactcaat ttcggtcaga ctggcgactc    2760
agagtcagtc cccgaccctc aacctctcgg agaacctcca gcagcgccct ctagtgtggg    2820
atctggtaca gtggctgcag gcggtggcgc accaatggca gacaataacg aaggtgccga    2880
cggagtgggt aatgcctcag gaaattggca ttgcgattcc acatggctgg gcgacagagt    2940
cattaccacc agcacccgaa cctgggccct gcccacctac aacaaccacc tctacaagca    3000
aatctccagt gaaactgcag gtagtaccaa cgacaacacc tacttcggct acagcacccc    3060
ctgggggtat tttgacttta acagattcca ctgccacttc tcaccacgtg actggcagcg    3120
actcatcaac aacaactggg gattccggcc caagaagctg cggttcaagc tcttcaacat    3180
ccaggtcaag gaggtcacga cgaatgacgg cgttacgacc atcgctaata accttaccag    3240
cacgattcag gtattctcgg actcggaata ccagctgccg tacgtcctcg gctctgcgca    3300 ccaggggctgc ctgcctccgt tcccggcgga cgtcttcatg attcctcagt acggctacct    3360
gactctcaac aatggcagtc agtctgtggg acgttcctcc ttctactgcc tggagtactt    3420
cccctctcag atgctgagaa cgggcaacaa ctttgagttc agctacagct tcgaggacgt    3480 gccttccac agcagctacg cacacagcca gagcctggac cggctgatga atccctcat     3540 cgaccagtac ttgtactacc tggccagaac acagagtaac ccaggaggca cagctggcaa    3600
tcgggaactg cagtttttacc agggcgggcc ttcaactatg gccgaacaag ccaagaattg    3660
gttacctgga ccttgcttcc ggcaacaaag agtctccaaa acgctggatc aaaacaacaa    3720
cagcaacttt gcttggactg gtgccaccaa atatcacctg aacggcagaa actcgttggt    3780
taatcccggc gtcgccatgg caactcacaa ggacgacgag gaccgcttt tcccatccag    3840 cggagtcctg attttttggaa aaactggagc aactaacaaa actacattgg aaaatgtgtt    3900
aatgacaaat gaagaagaaa ttcgtcctac taatcctgta gccacggaag aatacgggat    3960
agtcagcagc aacttacaag cggctaatac tgcagcccag acacaagttg tcaacaacca    4020
gggagcctta cctggcatgg tctgcagaa ccgggacgtg tacctgcagg gtcccatctg    4080
ggccaagatt cctcacacgg atggcaactt tcacccgtct cctttgatgg gcggctttgg    4140
acttaaacat ccgcctcctc agatcctgat caagaacact cccgttcccg ctaatcctcc    4200
ggaggtgttt actcctgcca gtttgcttc gttcatcaca cagtacagca ccggacaagt    4260
cagcgtggaa atcgagtggg agctgcagaa ggaaaacagc aagcgctgga acccggagat    4320
tcagtacacc tccaactttg aaaagcagac tggtgtggac tttgccgttg acagccaggg    4380
tgtttactct gagcctcgcc ctattggcac tcgttacctc accccgtaatc tgtaattgca    4440 tgttaatcaa taaaccggtt gattcgtttc agttgaactt tggtctcctg tgcttcttat    4500
cttatcggtt tccatagcaa ctggttacac attaactgct tgggtgcgct tcacgataag    4560
aacactgacg tcaccgcggt acccctagtg atggagttgg ccactccctc tatgcgcgct    4620
```

| | |
|---|---|
| cgctcgctcg gtggggcctg cggaccaaag gtccgcagac ggcagagctc tgctctgccg | 4680 |
| gccccaccga gcgagcgagc gcgcatagag ggagtggcca a | 4721 |

<210> SEQ ID NO 8
<211> LENGTH: 4393
<212> TYPE: DNA
<213> ORGANISM: Adeno-associated virus serotype 8

<400> SEQUENCE: 8

| | |
|---|---|
| cagagaggga gtggccaact ccatcactag gggtagcgcg aagcgcctcc cacgctgccg | 60 |
| cgtcagcgct gacgtaaatt acgtcatagg ggagtggtcc tgtattagct gtcacgtgag | 120 |
| tgcttttgcg gcattttgcg acaccacgtg gccatttgag gtatatatgg ccgagtgagc | 180 |
| gagcaggatc tccattttga ccgcgaaatt tgaacgagca gcagccatgc cgggcttcta | 240 |
| cgagatcgtg atcaaggtgc cgagcgacct ggacgagcac ctgccgggca tttctgactc | 300 |
| gtttgtgaac tgggtggccg agaaggaatg ggagctgccc ccggattctg acatggatcg | 360 |
| gaatctgatc gagcaggcac ccctgaccgt ggccgagaag ctgcagcgcg acttcctggt | 420 |
| ccaatggcgc gcgtgagta aggccccgga ggccctcttc tttgttcagt tcgagaaggg | 480 |
| cgagagctac tttcacctgc acgttctggt cgagaccacg ggggtcaagt ccatggtgct | 540 |
| aggccgcttc ctgagtcaga ttcgggaaaa gcttggtcca gaccatctac ccgcggggtc | 600 |
| gagccccacc ttgcccaact ggttcgcggt gaccaaagac gcggtaatgg cgccggcggg | 660 |
| ggggaacaag gtggtggacg agtgctacat ccccaactac ctcctgccca agactcagcc | 720 |
| cgagctgcag tgggcgtgga ctaacatgga ggagtatata agcgcgtgct gaacctggc | 780 |
| cgagcgcaaa cggctcgtgg cgcagcacct gacccacgtc agccagacgc aggagcagaa | 840 |
| caaggagaat ctgaacccca ttctgacgc gcccgtgatc aggtcaaaaa cctccgcgcg | 900 |
| ctatatggag ctggtcgggt ggctggtgga ccggggcatc acctccgaga agcagtggat | 960 |
| ccaggaggac caggcctcgt acatctcctt caacgccgcc tccaactcgc ggtcccagat | 1020 |
| caaggccgcg ctggacaatg ccggcaagat catggcgctg accaaatccg cgcccgacta | 1080 |
| cctggtgggg cccgctgcc ccgcggacat tacccagaac cgcatctacc gcatcctcgc | 1140 |
| tctcaacggc tacgaccctg cctacgccgg ctccgtcttt ctcggctggg ctcagaaaaa | 1200 |
| gttcgggaaa cgcaacacca tctggctgtt tggacccgcc accaccggca agaccaacat | 1260 |
| tgcggaagcc atcgcccacg ccgtgccctt ctacggctgc gtcaactgga ccaatgagaa | 1320 |
| ctttcccttc aatgattgcg tcgacaagat ggtgatctgg tgggaggagg caagatgac | 1380 |
| ggccaaggtc gtggagtccg ccaaggccat tctcggcggc agcaaggtgc gcgtggacca | 1440 |
| aaagtgcaag tcgtccgccc agatcgaccc caccccgtg atcgtcacct ccaacaccaa | 1500 |
| catgtgcgcc gtgattgacg ggaacagcac caccttcgag caccagcagc ctctccagga | 1560 |
| ccggatgttt aagttcgaac tcacccgcgc tctggagcac gactttgca aggtgacaaa | 1620 |
| gcaggaagtc aaagagttct tccgctgggc cagtgatcac gtgaccgagg tggcgcatga | 1680 |
| gttttacgtc agaaagggcg agccagcaa aagacccgcc ccgatgacg cggataaaag | 1740 |
| cgagcccaag cgggcctgcc cctcagtcgc ggatccatcg acgtcagacg cggaaggagc | 1800 |
| tccggtggac tttgccgaca ggtaccaaaa caatgttct cgtcacgcgg gcatgcttca | 1860 |
| gatgctgttt ccctgcaaaa cgtgcgagag aatgaatcag aatttcaaca tttgcttcac | 1920 |
| acacgggtc agagactgct cagagtgttt ccccggcgtg tcagaatctc aaccggtcgt | 1980 |

-continued

| | | | | |
|---|---|---|---|---|
| cagaaagagg | acgtatcgga | aactctgtgc | gattcatcat | ctgctggggc gggctcccga | 2040 |
| gattgcttgc | tcggcctgcg | atctggtcaa | cgtggacctg | gatgactgtg tttctgagca | 2100 |
| ataaatgact | taaaccaggt | atggctgccg | atggttatct | tccagattgg ctcgaggaca | 2160 |
| acctctctga | gggcattcgc | gagtggtggg | cgctgaaacc | tggagcccg aagcccaaag | 2220 |
| ccaaccagca | aaagcaggac | gacggccggg | gtctggtgct | tcctggctac aagtacctcg | 2280 |
| gacccttcaa | cggactcgac | aagggggagc | cgtcaacgc | gcggacgca gcggccctcg | 2340 |
| agcacgacaa | ggcctacgac | cagcagctgc | aggcgggtga | caatccgtac ctgcggtata | 2400 |
| accacgccga | cgccgagttt | caggagcgtc | tgcaagaaga | tacgtctttt ggggcaacc | 2460 |
| tcgggcgagc | agtcttccag | gccaagaagc | gggttctcga | acctctcggt ctggttgagg | 2520 |
| aaggcgctaa | gacggctcct | ggaaagaaga | gaccggtaga | gccatcaccc cagcgttctc | 2580 |
| cagactcctc | tacgggcatc | ggcaagaaag | gccaacagcc | cgccagaaaa agactcaatt | 2640 |
| ttggtcagac | tggcgactca | gagtcagttc | cagaccctca | acctctcgga gaacctccag | 2700 |
| cagcgccctc | tggtgtggga | cctaatacaa | tggctgcagg | cggtgcgca ccaatggcag | 2760 |
| acaataacga | aggcgccgac | ggagtgggta | gttcctcggg | aaattggcat tgcgattcca | 2820 |
| catggctggg | cgacagagtc | atcaccacca | gcacccgaac | ctgggccctg cccacctaca | 2880 |
| acaaccacct | ctacaagcaa | atctccaacg | ggacatcggg | aggagccacc aacgacaaca | 2940 |
| cctacttcgg | ctacagcacc | ccctgggggt | attttgactt | taacagattc cactgccact | 3000 |
| tttcaccacg | tgactggcag | cgactcatca | caacaactg | gggattccgg cccaagagac | 3060 |
| tcagcttcaa | gctcttcaac | atccaggtca | aggaggtcac | gcagaatgaa ggcaccaaga | 3120 |
| ccatcgccaa | taacctcacc | agcaccatcc | aggtgtttac | ggactcggag taccagctgc | 3180 |
| cgtacgttct | cggctctgcc | caccaggct | gcctgcctcc | gttcccggcg gacgtgttca | 3240 |
| tgattcccca | gtacggctac | ctaacactca | acaacggtag | tcaggccgtg gacgctcct | 3300 |
| ccttctactg | cctggaatac | tttccttcgc | agatgtgag | aaccggcaac aacttccagt | 3360 |
| ttacttacac | cttcgaggac | gtgccttttc | acagcagcta | cgcccacagc cagagcttgg | 3420 |
| accggctgat | gaatcctctg | attgaccagt | acctgtacta | cttgtctcgg actcaaacaa | 3480 |
| caggaggcac | ggcaaatacg | cagactctgg | gcttcagcca | aggtgggcct aatacaatgg | 3540 |
| ccaatcaggc | aaagaactgg | ctgccaggac | cctgttaccg | ccaacaacgc gtctcaacga | 3600 |
| caaccgggca | aaacaacaat | agcaactttg | cctggactgc | tgggaccaaa taccatctga | 3660 |
| atggaagaaa | ttcattggct | aatcctggca | tcgctatggc | aacacacaaa gacgacgagg | 3720 |
| agcgtttttt | tcccagtaac | gggatcctga | tttttggcaa | acaaaatgct gccagagaca | 3780 |
| atgcggatta | cagcgatgtc | atgctcacca | gcgaggaaga | aatcaaaacc actaaccctg | 3840 |
| tggctacaga | ggaatacggt | atcgtggcag | ataacttgca | gcagcaaaac acggctcctc | 3900 |
| aaattggaac | tgtcaacagc | caggggcct | acccggtat | ggtctggcag aaccgggacg | 3960 |
| tgtacctgca | gggtcccatc | tgggccaaga | ttcctcacac | ggacggcaac ttccacccgt | 4020 |
| ctccgctgat | gggcggcttt | ggcctgaaac | atcctccgcc | tcagatcctg atcaagaaca | 4080 |
| cgcctgtacc | tgcggatcct | ccgaccacct | tcaaccagtc | aaagctgaac tctttcatca | 4140 |
| cgcaatacag | caccggacag | gtcagcgtgg | aaattgaatg | ggagctgcag aaggaaaaca | 4200 |
| gcaagcgctg | gaaccccgag | atccagtaca | cctccaacta | ctacaaatct acaagtgtgg | 4260 |
| actttgctgt | taatacagaa | ggcgtgtact | ctgaaccccg | ccccattggc acccgttacc | 4320 |
| tcacccgtaa | tctgtaattg | cctgttaatc | aataaaccgg | ttgattcgtt tcagttgaac | 4380 |

```
tttggtctct gcg                                                         4393

<210> SEQ ID NO 9
<211> LENGTH: 46
<212> TYPE: DNA
<213> ORGANISM: Adeno-associated virus serotype 2

<400> SEQUENCE: 9
tgtagttaat gattaacccg ccatgctact tatctacgta gccatg              46

<210> SEQ ID NO 10
<211> LENGTH: 75
<212> TYPE: DNA
<213> ORGANISM: Adeno-associated virus serotype 2

<400> SEQUENCE: 10
tgtagttaat gattaacccg ccatgctact tatctacgta gccatggaaa ctagataaga   60
aagaaatacg cagag                                                    75

<210> SEQ ID NO 11
<211> LENGTH: 105
<212> TYPE: DNA
<213> ORGANISM: Adeno-associated virus serotype 2

<400> SEQUENCE: 11
tgtagttaat gattaacccg ccatgctact tatctacgta gccatggaaa ctagataaga   60
aagaaatacg cagagaccaa agttcaactg aaacgaatta aacgg                  105

<210> SEQ ID NO 12
<211> LENGTH: 133
<212> TYPE: DNA
<213> ORGANISM: Adeno-associated virus serotype 2

<400> SEQUENCE: 12
tgtagttaat gattaacccg ccatgctact tatctacgta gccatggaaa ctagataaga   60
aagaaatacg cagagaccaa agttcaactg aaacgaatta aacggtttat tgattaacaa  120
gcaattacag att                                                     133

<210> SEQ ID NO 13
<211> LENGTH: 119
<212> TYPE: DNA
<213> ORGANISM: artificial sequence
<220> FEATURE:
<223> OTHER INFORMATION: AAV2-105 insert

<400> SEQUENCE: 13
gcggccgctg tagttaatga ttaacccgcc atgctactta tctacgtagc catggaaact   60
agataagaaa gaaatacgca gagaccaaag ttcaactgaa acgaattaaa cggtctaga   119

<210> SEQ ID NO 14
<211> LENGTH: 147
<212> TYPE: DNA
<213> ORGANISM: artificial sequence
<220> FEATURE:
<223> OTHER INFORMATION: AAV2-133 insert

<400> SEQUENCE: 14
gcggccgctg tagttaatga ttaacccgcc atgctactta tctacgtagc catggaaact   60
agataagaaa gaaatacgca gagaccaaag ttcaactgaa acgaattaaa cggtttattg  120
```

-continued

```
attaacaagc aattacagat ttctaga                                             147

<210> SEQ ID NO 15
<211> LENGTH: 121
<212> TYPE: DNA
<213> ORGANISM: Adeno-associated virus serotype 7

<400> SEQUENCE: 15
cggtgacgtc agtgttctta tcgtgaagcg cacccaagca gttaatgtgt aaccagttgc          60
tatggaaacc gataagataa gaagcacagg agaccaaagt tcaactgaaa cgaatcaacc         120
g                                                                         121

<210> SEQ ID NO 16
<211> LENGTH: 149
<212> TYPE: DNA
<213> ORGANISM: Adeno-associated virus serotype 7

<400> SEQUENCE: 16
cggtgacgtc agtgttctta tcgtgaagcg cacccaagca gttaatgtgt aaccagttgc          60
tatggaaacc gataagataa gaagcacagg agaccaaagt tcaactgaaa cgaatcaacc         120
ggtttattga ttaacatgca attacagat                                           149

<210> SEQ ID NO 17
<211> LENGTH: 135
<212> TYPE: DNA
<213> ORGANISM: artificial sequence
<220> FEATURE:
<223> OTHER INFORMATION: AAV7-121 insert

<400> SEQUENCE: 17
gcggccgccg gtgacgtcag tgttcttatc gtgaagcgca cccaagcagt taatgtgtaa          60
ccagttgcta tggaaaccga taagataaga agcacaggag accaaagttc aactgaaacg         120
aatcaaccgt ctaga                                                          135

<210> SEQ ID NO 18
<211> LENGTH: 163
<212> TYPE: DNA
<213> ORGANISM: artificial sequence
<220> FEATURE:
<223> OTHER INFORMATION: AAV7-149 insert

<400> SEQUENCE: 18
gcggccgccg gtgacgtcag tgttcttatc gtgaagcgca cccaagcagt taatgtgtaa          60
ccagttgcta tggaaaccga taagataaga agcacaggag accaaagttc aactgaaacg         120
aatcaaccgg tttattgatt aacatgcaat tacagattct aga                           163

<210> SEQ ID NO 19
<211> LENGTH: 121
<212> TYPE: DNA
<213> ORGANISM: Adeno-associated virus serotype 5

<400> SEQUENCE: 19
gatgttgtaa gctgttattc attgaatgac cacaagaggc agtattttac tgacacgaat          60
acacggttta ttgagggtat gcgacatgaa tgggttaaag ggtcgggta aggtatcggg          120 t                                                                         121

<210> SEQ ID NO 20
<211> LENGTH: 149
```

```
<212> TYPE: DNA
<213> ORGANISM: Adeno-associated virus serotype 5

<400> SEQUENCE: 20
gatgttgtaa gctgttattc attgaatgac cacaagaggc agtatttac tgacacgaat      60 acacggttta ttgagggtat gcgacatgaa tgggttaaag gggtcgggta aggtatcggg     120
ttccgatagg tctggtggtt ctgtattcc                                        149

<210> SEQ ID NO 21
<211> LENGTH: 135
<212> TYPE: DNA
<213> ORGANISM: artificial sequence
<220> FEATURE:
<223> OTHER INFORMATION: AAV5-121 insert

<400> SEQUENCE: 21
gcggccgcga tgttgtaagc tgttattcat tgaatgacca caagaggcag tattttactg      60
acacgaatac acggtttatt gagggtatgc gacatgaatg ggttaaaggg gtcgggtaag     120
gtatcgggtt ctaga                                                       135

<210> SEQ ID NO 22
<211> LENGTH: 163
<212> TYPE: DNA
<213> ORGANISM: artificial sequence
<220> FEATURE:
<223> OTHER INFORMATION: AAV5-149 insert

<400> SEQUENCE: 22
gcggccgcga tgttgtaagc tgttattcat tgaatgacca caagaggcag tattttactg      60
acacgaatac acggtttatt gagggtatgc gacatgaatg ggttaaaggg gtcgggtaag     120
gtatcgggtt ccgataggtc tggtggttct gtattcctct aga                        163

<210> SEQ ID NO 23
<211> LENGTH: 162
<212> TYPE: DNA
<213> ORGANISM: artificial sequence
<220> FEATURE:
<223> OTHER INFORMATION: R105

<400> SEQUENCE: 23
tgggttgata tggaacctaa ctgatttaat cccaaacgcc gataacccca gtgggaatcg      60
cttgaaaaca gtctaactgg tacgtaggac cgtaggtttc agatatccac tccggtgaat     120
tctttaccct tgggtacgg gactctgtac cgaaggtctc ga                          162

<210> SEQ ID NO 24
<211> LENGTH: 145
<212> TYPE: DNA
<213> ORGANISM: Adeno-associated virus serotype 2

<400> SEQUENCE: 24
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcct                                            145

<210> SEQ ID NO 25
<211> LENGTH: 144
<212> TYPE: DNA
<213> ORGANISM: Adeno-associated virus serotype 2
```

<400> SEQUENCE: 25
ggaacccctc gtgatggagt tggccactcc ctctctgcgc gctcgctcgc tcactgaggc    60
cgggcgacca aggtcgccc gacgcccggg ctttgcccgg gcggcctcag tgagcgagcg   120
agcgcgcaga gagggagtgg ccaa                                         144

<210> SEQ ID NO 26
<211> LENGTH: 26
<212> TYPE: DNA
<213> ORGANISM: artificial sequence
<220> FEATURE:
<223> OTHER INFORMATION: PCR primer OTC005f

<400> SEQUENCE: 26
gtatcgatgt gctccagaag ccaaag                                        26

<210> SEQ ID NO 27
<211> LENGTH: 29
<212> TYPE: DNA
<213> ORGANISM: artificial sequence
<220> FEATURE:
<223> OTHER INFORMATION: PCR primer OTC004r

<400> SEQUENCE: 27
gatgaataaa aaaatagat atcgatggc                                      29

<210> SEQ ID NO 28
<211> LENGTH: 20
<212> TYPE: DNA
<213> ORGANISM: artificial sequence
<220> FEATURE:
<223> OTHER INFORMATION: PCR primer eGFPf

<400> SEQUENCE: 28
tcaagatccg ccacaacatc                                               20

<210> SEQ ID NO 29
<211> LENGTH: 20
<212> TYPE: DNA
<213> ORGANISM: artificial sequence
<220> FEATURE:
<223> OTHER INFORMATION: PCR primer eGFPr

<400> SEQUENCE: 29
ttctcgttgg ggtctttgct                                               20

<210> SEQ ID NO 30
<211> LENGTH: 21
<212> TYPE: DNA
<213> ORGANISM: artificial sequence
<220> FEATURE:
<223> OTHER INFORMATION: PCR primer GAPf11

<400> SEQUENCE: 30
gctctctgct cctcctgttc g                                             21

<210> SEQ ID NO 31
<211> LENGTH: 19
<212> TYPE: DNA
<213> ORGANISM: artificial sequence
<220> FEATURE:
<223> OTHER INFORMATION: PCR primer GAPf12

<400> SEQUENCE: 31
gcgaacacat ccggcctgc                                                19

<210> SEQ ID NO 32
<211> LENGTH: 145
<212> TYPE: DNA
<213> ORGANISM: Adeno-associated virus serotype

<400> SEQUENCE: 32

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcct                                           145
```

<210> SEQ ID NO 33
<211> LENGTH: 218
<212> TYPE: DNA
<213> ORGANISM: Adeno-associated virus serotype 1

<400> SEQUENCE: 33

```
gggcaactcc atcactaggg gtaacccgat gacgtaagtc ttttatcgcg aagcgcaacc      60
aagcagttaa tgtgtaagct ataaccatgg taaccgataa gataagaagg acaggagacc     120
aaagttcaac tgaaacgaat caaccggttt attgattaac acgtaattac aggggacggg     180
taaggtaacg ggtgccaatg gggcgaggct cagtataa                             218
```

<210> SEQ ID NO 34
<211> LENGTH: 202
<212> TYPE: DNA
<213> ORGANISM: Adeno-associated virus serotype 2

<400> SEQUENCE: 34

```
ggccaactcc atcactaggg gttccttgta gttaatgatt aacccgccat gctacttatc      60
tacgtagcca tggaaactag ataagaaaga atacgcaga gaccaaagtt caactgaaac      120
gaattaaacg gtttattgat taacaagcaa ttacagatta cgagtcaggt atctggtgcc     180
aatggggcga ggctctgaat ac                                              202
```

<210> SEQ ID NO 35
<211> LENGTH: 240
<212> TYPE: DNA
<213> ORGANISM: Adeno-associated virus serotype 3

<400> SEQUENCE: 35

```
ggccaactcc atcactagag gtatggcgag agttaaatat taaccagcag ttgtaaaccg      60
cgaagcgcaa cgccgcagg ccgctgctta tctacgcagt agccatggaa acaagataaa     120 gataagaag tgcacaagag ccaaagttca actgaaacga attaaacggt ttattgatta     180
accaggattc acaagtttcg tgtgagatac cgggttccaa tagggcgagg ttcactataa     240
```

<210> SEQ ID NO 36
<211> LENGTH: 236
<212> TYPE: DNA
<213> ORGANISM: Adeno-associated virus serotype 4

<400> SEQUENCE: 36

```
ggccaactcc atcatctggt ttgccagaag ttactgatta accggcagtt gtaaaccgcg      60
aagcgcaagc gccgcaggcc gctgcttatg tacgcagtag ccatggaaac gagataagat     120
aagaaggaca cggagaccaa agttcaactg aaacgaataa accggtttat tgattaacag     180
gttattacag gtggtgggtg aggtagcggg taccgatagc cctaggctca gtgtat         236
```

<210> SEQ ID NO 37
<211> LENGTH: 198
<212> TYPE: DNA
<213> ORGANISM: Adeno-associated virus serotype 6

<400> SEQUENCE: 37

```
gggcaactcc atcactaggg gtattcgcga agcgcaacta agcagttaat gtgtaaccgg      60
ttgctatggt gaccagataa gataataacg acatgagacc aaagttcaac tgacacgaat     120
taaccggttt attgattaac acacaattac aggggacggg tgaggtaacg ggtgccaatg     180
gggcgaggct cagtataa                                                    198
```

<210> SEQ ID NO 38
<211> LENGTH: 219
<212> TYPE: DNA
<213> ORGANISM: adeno-associated virus serotype 7

<400> SEQUENCE: 38

```
ggccaactcc atcactaggg gtaccgcggt gacgtcagtg ttcttatcgt gaagcgcacc      60
caagcagtta atgtgtaacc agttgctatg gaaaccgata agataagaag cacaggagac     120
caaagttcaa ctgaaacgaa tcaaccggtt tattgattaa catgcaatta cagattacgg     180
gtgaggtaac gagtgccaat agggcgaggc tcagagtaa                            219
```

<210> SEQ ID NO 39
<211> LENGTH: 108
<212> TYPE: DNA
<213> ORGANISM: Adeno-associated virus serotype 8

<400> SEQUENCE: 39

```
cgcagagacc aaagttcaac tgaaacgaat caaccggttt attgattaac aggcaattac      60
agattacggg tgaggtaacg ggtgccaatg gggcggggtt cagagtac                  108
```

<210> SEQ ID NO 40
<211> LENGTH: 119
<212> TYPE: DNA
<213> ORGANISM: Artificial Sequence
<220> FEATURE:
<223> OTHER INFORMATION: AAV2-105 (Fig 7)

<400> SEQUENCE: 40

```
gcggccgctg tagttaatga ttaacccgcc atgctactta tctacgtagc catggaaact      60
agataagaaa gaaatacgca gagaccaaag ttcaactgaa acgaattaaa cggtctaga     119
```

<210> SEQ ID NO 41
<211> LENGTH: 147
<212> TYPE: DNA
<213> ORGANISM: Artificial Sequence
<220> FEATURE:
<223> OTHER INFORMATION: AAV2-133 (Fig 7)

<400> SEQUENCE: 41

```
gcggccgctg tagttaatga ttaacccgcc atgctactta tctacgtagc catggaaact      60
agataagaaa gaaatacgca gagaccaaag ttcaactgaa acgaattaaa cggtttattg     120
attaacaagc aattacagat ttctaga                                          147
```

<210> SEQ ID NO 42
<211> LENGTH: 135
<212> TYPE: DNA
<213> ORGANISM: Artificial Sequence

```
<220> FEATURE:
<223> OTHER INFORMATION: AAV5-121 (Fig 7)

<400> SEQUENCE: 42
gcggccgcga tgttgtaagc tgttattcat tgaatgacca caagaggcag tattttactg    60
acacgaatac acggtttatt gagggtatgc gacatgaatg ggttaaaggg gtcgggtaag   120
gtatcgggtt ctaga                                                    135

<210> SEQ ID NO 43
<211> LENGTH: 163
<212> TYPE: DNA
<213> ORGANISM: Artificial Sequence
<220> FEATURE:
<223> OTHER INFORMATION: AAV5-149 (Fig 7)

<400> SEQUENCE: 43
gcggccgcga tgttgtaagc tgttattcat tgaatgacca caagaggcag tattttactg    60
acacgaatac acggtttatt gagggtatgc gacatgaatg ggttaaaggg gtcgggtaag   120
gtatcgggtt ccgataggtc tggtggttct gtattcctct aga                    163
```

PROMOTERS FOR EXPRESSION OF HETEROLOGOUS GENES

RELATED APPLICATION

This application is associated with and claims priority from Australian provisional patent application no. 2015901677 filed on 8 May 2015, the entire contents of which is incorporated herein by reference.

SEQUENCE LISTING

The instant application contains a Sequence Listing that has been submitted in ASCII format via EFS-Web and is hereby incorporated by reference in its entirety. Said ASCII copy, created on Oct. 12, 2020, is named 06950_002US1_Sequence_Listing.txt and is 59 KB in size.

FIELD OF INVENTION

The present disclosure relates generally to promoters for the expression of one or more heterologous coding sequences, and isolated polynucleotides, vectors and recombinant viruses comprising the promoters. The present disclosure also relates to enhancers for increasing the expression of one or more heterologous coding sequences, and isolated polynucleotides, vectors and recombinant viruses comprising the enhancers.

BACKGROUND OF THE DISCLOSURE

The expression of heterologous coding sequences is widely used across many fields and industries, in particular the medical and biotechnology industries. In many instances, heterologous coding sequences are expressed in vitro for subsequent purification of the heterologous protein, which can then be used for research, therapeutic or other uses. In other instances, the heterologous coding sequence is introduced into a subject for expression in that subject typically in order to treat a disease or condition, generally referred to as gene therapy.

Gene therapy has most commonly been investigated and achieved using viral vectors, in particular adeno-associated viral vectors, although lentiviral, retroviral, adenoviral, herpesviral, and hepatitis viral vectors have also been utilized. Adeno-associated virus (AAV) is a replication-deficient parvovirus, the single-stranded DNA genome of which is about 4.7 kb in length including 145 nucleotide inverted terminal repeat (ITRs). The ITRs play a role in integration of the AAV DNA into the host cell genome. When AAV infects a host cell, the viral genome integrates into the host's chromosome resulting in latent infection of the cell. Thus, AAV can be exploited to introduce heterologous coding sequences into cells. In a natural system, a helper virus (for example, adenovirus or herpesvirus) provides genes that allow for production of AAV virus in the infected cell. In the case of adenovirus, genes E1A, E1B, E2A, E4 and VA provide helper functions. Upon infection with a helper virus, the AAV provirus is rescued and amplified, and both AAV and adenovirus are produced.

Recombinant AAVs containing a genome that lacks some or most of the native AAV genome and instead contains one or more heterologous coding sequences flanked by the ITRs have been successfully used in gene therapy settings. One of the major problems associated with the use of recombinant AAV, and indeed other recombinant virus systems, is the limitations on the size of the heterologous coding sequence that can be packaged into the virus. AAV can package a genome slightly larger than the size of a wild-type genome (approximately 4.6 kb). Optimal packaging is achieved with genomes having a size of 4.1-4.9 kb, and packaging efficiencies reduce significantly when larger genomes are packaged. Given that many of the known promoters and other regulatory elements useful for expression of a heterologous coding sequence in the gene therapy context have combined lengths of over 1 kb, and often over 1.5 kb or 2 kb, there is a significant limit on the size of the heterologous coding sequence that can be packaged into the recombinant virus. Thus, there is a continued need for new, smaller promoters that are useful for gene therapy and indeed other biotechnological applications.

SUMMARY OF THE DISCLOSURE

The present disclosure is predicated in part on the identification of an anti-sense region in Adeno-associated virus (AAV) that has promoter activity. Nucleic acid sequences based on this anti-sense region can be used as promoters to drive the expression of an operably linked heterologous coding sequence. These newly-identified promoters of the present disclosure are relatively small, making them particularly useful for the expression of larger heterologous coding sequences using vectors with size restraints, such as AAV vectors. As described herein, this promoter region also has enhancer activity and can be used as an enhancer to increase expression of a heterologous coding sequence from another promoter that is operably linked to the a heterologous coding sequence.

In one aspect, the present disclosure is directed to a vector comprising a promoter comprising a sequence of nucleotides corresponding to the reverse, complement sequence of nucleotides 4485-4530 of the adeno-associated virus serotype 2 (AAV2) genome set forth in SEQ ID NO:1 or corresponding nucleotides from another AAV, or a sequence having at least 90% sequence identity to the reverse, complement sequence of nucleotides 4485-4530 of the AAV2 genome set forth in SEQ ID NO:1, wherein the promoter is operably linked to a heterologous coding sequence.

In a further aspect, the disclosure is directed to a vector comprising a promoter (i.e. a first promoter) comprising a sequence of nucleotides corresponding to the reverse, complement sequence of nucleotides 4485-4530 of the AAV2 genome set forth in SEQ ID NO:1 or corresponding nucleotides from another AAV, or a sequence having at least 90% sequence identity to the reverse, complement sequence of nucleotides 4485-4530 of the AAV2 genome set forth in SEQ ID NO:1, wherein the vector contains at most only one other promoter (i.e. a second promoter) which drives the expression of a selectable or reportable marker. In one embodiment, the vector comprises one or more restriction enzyme sites positioned downstream of the (first) promoter to facilitate the insertion of a heterologous coding sequence that is operably linked to the promoter. In particular examples, the (first) promoter is operably linked to a heterologous coding sequence encoding a polypeptide.

The vectors may further comprise a spacer immediately downstream of the promoter, wherein the total length of the promoter and spacer is at least 60, 70, 80, 90, 100, 110, 120, or 130 nucleotides.

In some embodiments, the promoter comprises a sequence of nucleotides corresponding to the reverse, complement sequence of nucleotides 4398-4530, 4426-4530, or 4456-4530 of the AAV2 genome set forth in SEQ ID NO:1 or corresponding nucleotides from another AAV, or a sequence having at least 90% sequence identity to the reverse, complement sequence of nucleotides 4398-4530, 4426-4530, or 4456-4530 of the AAV2 genome set forth in SEQ ID NO:1. In particular examples, the promoter comprises a sequence of nucleotides set forth in any one of SEQ ID NOs:9-12, or a sequence having at least 90% sequence identity to the sequence of nucleotides set forth in any one of SEQ ID NOs:9-12.

The vectors can further comprise an AAV inverted terminal repeat (ITR) upstream of the promoter. In some embodiments, the ITR comprises a sequence having at least 90% sequence identity to the AAV2 ITR set forth in SEQ ID NO:24, 25 or 32.

In further aspects, vectors are provided comprising a promoter comprising up to about 133 nucleotides, which nucleotides correspond to the reverse, complement sequence of nucleotides from positions 4398-4530 of AAV2 genome set forth in SEQ ID NO:1 or corresponding nucleotides from another AAV, or a sequence having at least 90% sequence identity to the reverse, complement sequence of nucleotides from positions 4398-4530 of the AAV2 genome set forth in SEQ ID NO:1, wherein the promoter is operably linked to a heterologous coding sequence.

In particular examples, the promoter comprises up to about 105 nucleotides, which nucleotides correspond to the reverse, complement sequence of nucleotides from positions 4426-4530 of AAV2 genome set forth in SEQ ID NO:1 or corresponding nucleotides from another AAV, or a sequence having at least 90% sequence identity to the reverse, complement sequence of nucleotides from positions 4426-4530 of the AAV2 genome set forth in SEQ ID NO:1. In further examples, the promoter comprises up to about 75 nucleotides, which nucleotides correspond to the reverse, complement sequence of nucleotides from positions 4456-4530 of AAV2 genome set forth in SEQ ID NO:1 or corresponding nucleotides from another AAV, or a sequence having at least 90% sequence identity to the reverse, complement sequence of nucleotides from positions 4456-4530 of the AAV2 genome set forth in SEQ ID NO:1. In other examples, the promoter comprises up to about 46 nucleotides, which nucleotides correspond to the reverse, complement sequence of nucleotides from positions 4485-4530 of AAV2 genome set forth in SEQ ID NO:1 or corresponding nucleotides from another AAV, or a sequence having at least 90% sequence identity to the reverse, complement sequence of nucleotides from positions 4485-4530 of the AAV2 genome set forth in SEQ ID NO:1. Such vectors can further comprising a spacer between the promoter and the heterologous coding sequence, wherein the total length of the promoter and spacer is at least 60, 70, 80, 90, 100, 110, 120, or 130 nucleotides.

In instances where the vector comprises a heterologous coding sequence, the heterologous coding sequence may, for example, encode a peptide, polypeptide, or polynucleotide. In one embodiment, the polynucleotide is an antisense oligonucleotide.

In particular embodiments, the vectors of the present disclosure are plasmids. In further embodiments, the vectors are viral vectors, such as, for example, AAV, lentiviral, retroviral, adenoviral, herpesviral, or hepatitis viral vectors.

Also provided are vectors, comprising, from 5' to 3', a 5' ITR, a promoter, and a 3' ITR, wherein: the promoter is the only promoter between the 5' ITR and 3' ITR; and the promoter comprises a sequence of nucleotides corresponding to the reverse, complement sequence of nucleotides 4485-4530 of the AAV2 genome set forth in SEQ ID NO:1 or corresponding nucleotides from another AAV, or a sequence having at least 90% sequence identity to the reverse, complement sequence of nucleotides 4485-4530 of the AAV2 genome set forth in SEQ ID NO:1.

In some embodiments, such vectors further comprise a spacer immediately downstream of the promoter, wherein the total length of the promoter and spacer is at least 60, 70, 80, 90, 100, 110, 120, or 130 nucleotides. In further embodiments, the vector comprises one or more restriction enzyme sites positioned downstream of the promoter to facilitate insertion of a heterologous coding sequence that is operably linked to the promoter. In particular examples, the vector comprises a heterologous coding sequence operably linked to the promoter. The heterologous coding sequence can encode, for example, a peptide, polypeptide, or polynucleotide, such as an antisense oligonucleotide.

In further embodiments, the promoter of this vector comprises a sequence of nucleotides corresponding to the reverse, complement sequence of nucleotides 4398-4530, 4426-4530, or 4456-4530 of the AAV2 genome set forth in SEQ ID NO:1 or corresponding nucleotides from another AAV, or a sequence having at least 90% sequence identity to the reverse, complement sequence of nucleotides 4398-4530, 4426-4530, or 4456-4530 of the AAV2 genome set forth in SEQ ID NO:1. In a particular example, the promoter comprises up to about 133 nucleotides, which nucleotides correspond to the reverse, complement sequence of nucleotides from positions 4398-4530 of AAV2 genome set forth in SEQ ID NO:1 or corresponding nucleotides from another AAV, or a sequence having at least 90% sequence identity to the reverse, complement sequence of nucleotides from positions 4398-4530 of the AAV2 genome set forth in SEQ ID NO:1, wherein the promoter is operably linked to a heterologous coding sequence. For example, the promoter may comprise a sequence of nucleotides set forth in any one of SEQ ID NOs:9-12, or a sequence having at least 90% sequence identity to the sequence of nucleotides set forth in any one of SEQ ID NOs:9-12.

In such vectors, the 5' ITR and 3' ITR may be, for example, derived from AAV viruses of the same or different serotypes. In one embodiment, the 5' ITR and 3' ITR are derived from AAV1, AAV2, AAV3, AAV4, AAV5, AAV6, AAV7 or AAV8 serotypes. In particular examples, the 5' ITR or 3' ITR comprises a sequence having at least 90% sequence identity to the AAV2 ITR set forth in SEQ ID NO:24, 25 or 32.

The present disclosure also provides recombinant viruses produced by packaging a vector of described above and herein. In some examples, the recombinant viruses are recombinant AAV.

In one aspect, provided is a recombinant virus having a genome that comprises a promoter comprising a sequence of nucleotides corresponding to the reverse, complement sequence of nucleotides 4485-4530 of the AAV2 genome set forth in SEQ ID NO:1 or corresponding nucleotides from another AAV, or a sequence having at least 90% sequence identity to the reverse, complement sequence of nucleotides 4485-4530 of the AAV2 genome set forth in SEQ ID NO:1, wherein the promoter is operably linked to a heterologous coding sequence. In some embodiments, the recombinant virus is selected from among a recombinant AAV, lentivirus, retrovirus, adenovirus, herpes virus, and hepatitis virus.

In some instances, the recombinant virus further comprises a spacer between the promoter and the heterologous coding sequence, wherein the total length of the promoter and spacer is at least 60, 70, 80, 90, 100, 110, 120, or 130 nucleotides.

In particular examples, the promoter comprises a sequence of nucleotides corresponding to the reverse, complement sequence of nucleotides 4398-4530, 4426-4530, or 4456-4530 of the AAV2 genome set forth in SEQ ID NO:1 or corresponding nucleotides from another AAV, or a sequence having at least 90% sequence identity to the reverse, complement sequence of nucleotides 4398-4530, 4426-4530, or 4456-4530 of the AAV2 genome set forth in SEQ ID NO:1. For example, the promoter may comprise a sequence of nucleotides set forth in any one of SEQ ID NOs:9-12, or a sequence having at least 90% sequence identity to the sequence of nucleotides set forth in any one of SEQ ID NOs:9-12.

In one embodiment, the genome of the recombinant virus comprises, from 5' to 3', a 5' ITR, the promoter operably linked to the heterologous coding sequence, and a 3' ITR, wherein the recombinant virus is a recombinant AAV. In further embodiments, the genome comprises, from 5' to 3', a 5' ITR, the promoter operably linked to the heterologous coding sequence, a spacer, and a 3' ITR, wherein the recombinant virus is a recombinant AAV. The 5' ITR and 3' ITR may be, in some examples, derived from AAV viruses of the same or different serotypes. In one embodiment, the 5' ITR and 3' ITR are derived from AAV1, AAV2, AAV3, AAV4, AAV5, AAV6, AAV7 or AAV8 serotypes. In particular examples, the 5' ITR or 3' ITR comprises a sequence having at least 90% sequence identity to the AAV2 ITR set forth in SEQ ID NO:24, 25 or 32.

In a further aspect of the present disclosure, provided is an isolated polynucleotide having promoter activity, the polynucleotide comprising up to about 133 nucleotides, which nucleotides correspond to the reverse, complement sequence of nucleotides from positions 4398-4530 of AAV2 genome set forth in SEQ ID NO:1 or corresponding nucleotides from another AAV, or a sequence having at least 90% sequence identity to the reverse, complement sequence of nucleotides from positions 4398-4530 of the AAV2 genome set forth in SEQ ID NO:1, wherein the promoter is operably linked to a heterologous coding sequence.

In one embodiment, the promoter comprises up to about 105 nucleotides, which nucleotides correspond to the reverse, complement sequence of nucleotides from positions 4426-4530 of AAV2 genome set forth in SEQ ID NO:1 or corresponding nucleotides from another AAV, or a sequence having at least 90% sequence identity to the reverse, complement sequence of nucleotides from positions 4426-4530 of the AAV2 genome set forth in SEQ ID NO:1. In a further embodiment, the promoter comprises up to about 75 nucleotides, which nucleotides correspond to the reverse, complement sequence of nucleotides from positions 4456-4530 of AAV2 genome set forth in SEQ ID NO:1 or corresponding nucleotides from another AAV, or a sequence having at least 90% sequence identity to the reverse, complement sequence of nucleotides from positions 4456-4530 of the AAV2 genome set forth in SEQ ID NO:1. In still a further embodiment, the promoter comprises up to about 46 nucleotides, which nucleotides correspond to the reverse, complement sequence of nucleotides from positions 4485-4530 of AAV2 genome set forth in SEQ ID NO:1 or corresponding nucleotides from another AAV, or a sequence having at least 90% sequence identity to the reverse, complement sequence of nucleotides from positions 4485-4530 of the AAV2 genome set forth in SEQ ID NO:1. In such instances, the isolated polynucleotide may further comprising a spacer immediately downstream of the promoter, wherein the total length of the promoter and spacer is at least 60, 70, 80, 90, 100, 110, 120, or 130 nucleotides.

The present disclosure is also directed to an isolated polynucleotide, comprising an enhancer operably linked to a promoter, wherein the enhancer comprises: up to 105 nucleotides, which nucleotides correspond to the sequence of nucleotides from positions 4426-4530 of the AAV2 genome set forth in SEQ ID NO:1 or the reverse, complement sequence of nucleotides from positions 4426-4530 or corresponding nucleotides from another AAV, or a sequence having at least 90% sequence identity thereto; or a sequence of nucleotides corresponding to the sequence of nucleotides from positions 4426-4530 of the AAV2 genome set forth in SEQ ID NO:1 or the reverse, complement sequence of nucleotides 4426-4530 or corresponding nucleotides from another AAV, or a sequence having at least 90% sequence identity thereto.

In some embodiments, this isolated polynucleotide comprises the sequence of nucleotides set forth in SEQ ID NO:11 or the reverse complement thereof, or a sequence having at least 90% sequence identity thereto. In further embodiments, the isolated polynucleotide comprises up to 105 nucleotides of the sequence of nucleotides set forth in SEQ ID NO:11 or the reverse complement thereof, or a sequence having at least 90% sequence identity thereto. In some examples, the promoter is not an AAV promoter. The isolated polynucleotide may comprise 2 or more enhancers operably linked to the promoter. In particular examples, the promoter is operably linked to a heterologous coding sequence.

Also provided are host cells, comprising the vectors, polynucleotides and/or recombinant viruses described above and herein.

The present disclosure is also directed to a method for expressing a heterologous coding sequence, comprising introducing into a host cell a vector, a recombinant virus or an isolated polynucleotide described above and herein that comprises a heterologous coding sequence. Such methods may be performed in vitro, ex vivo or in vivo. In instances where the methods are performed in vitro or ex vivo, the host cells can be grown or cultured under conditions that facilitate expression of the heterologous coding sequence.

BRIEF DESCRIPTION OF THE DRAWINGS

Embodiments of the disclosure are described herein, by way of non-limiting example only, with reference to the following drawings.

FIG. 5 shows an alignment of the reverse, complement sequence of the region upstream of the 3' ITR in AAV1, AAV2, AAV3, AAV4, AAV6, AAV7 and AAV1 genomes. Bolded sequence depicts putative HNF1 binding sites. Underlined sequence depicts putative HNF1α-c binding sites. Bolded and underlined sequence depicts putative HNF4α binding sites.

FIG. 7 shows the nucleotide sequences of the inserts, annotated to show putative HNF1, HNF1c and HNF4α binding sites, the VP1 stop codon, and Not I and Xba I restriction enzyme sites.

FIG. 8 shows the results of a study assessing GFP expression from AAV-LSP1-GFP and AAV-2/1-105-GFP in mice. AAV-LSP1-GFP or AAV-2/1-105-GFP were injected intraperitoneally into adult female and male C57BL/6 mice ($5 \times 10^{10}$ vg in 100 μL PBS per mouse, n=3-5 per vector per sex) and livers were analyzed two weeks later for (A) eGFP mRNA relative to β-actin mRNA and (B) recombinant eGFP in liver lysates. Values in (A) and (B) are expressed per vector genome or per $10^6$ vector genomes respectively after normalization to GAPDH.

FIG. 9 shows promoter activity from the 2/1-105 element with and without the A/D ITR junction. (A) A schematic of the cloning strategy to generate the vectors containing the 2/1-105 element with and without A/D junction or the eGFP cassette without upstream sequence. (B) The proportion of eGFP positive HUH7 cells following transfection with the vectors (C) MFI of eGFP positive cells following transfection with the vectors. All cultures were co-transfected with a control plasmid encoding mCherry under the transcriptional regulation of a CMV promoter and analyzed for (D). The proportion of mCherry positive HUH7 cells following co-transfection with a control plasmid encoding mCherry under the transcriptional regulation of a CMV promoter (E) MFI of mCherry positive cells following co-transfection with a control plasmid encoding mCherry under the transcriptional regulation of a CMV promoter. Duplicate transfections performed per experiment with data representative of two independent experiments.

DETAILED DESCRIPTION

Figure 1:
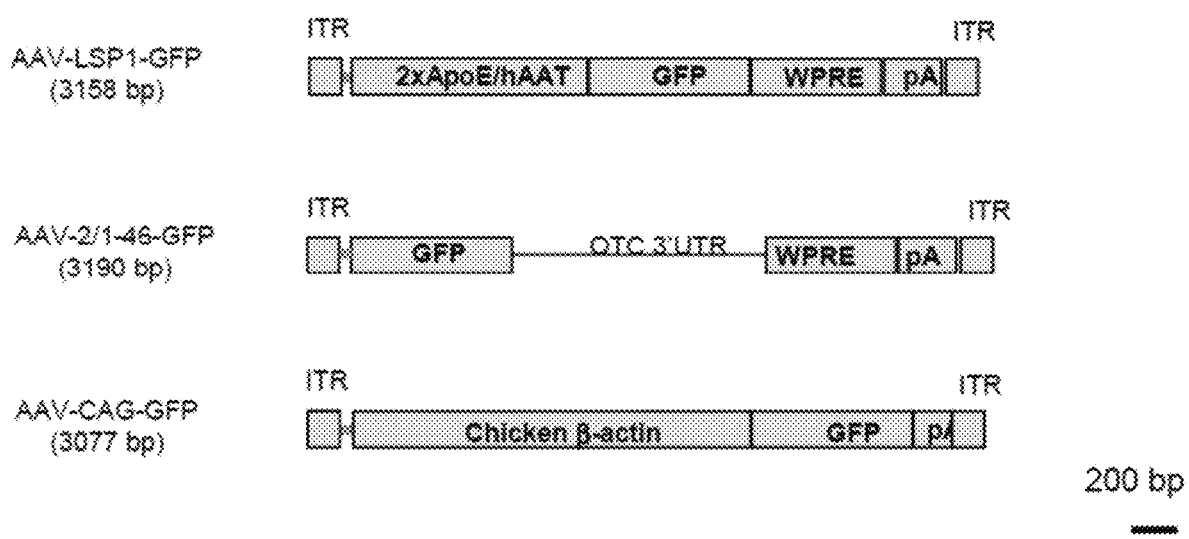
FIG. 1 is a schematic showing the regions flanked by the AAV ITRs in three recombinant AAVs. The region in rAAV-LSP1-GFP is 3158 bp and contains GFP under the transcriptional control of a heterologous promoter containing one copy of the liver-specific hAAT promoter and two copies of the ApoE enhancer element (2× ApoE/hAAT). The region in rAAV-2/1-46+65BS-GFP is 3190 bp and lacks any conventional promoter upstream of the GFP. The region in rAAV-CAG-GFP contains GFP under the control of the constitutive chicken β-actin promoter.

Unless defined otherwise, all technical and scientific terms used herein have the same meaning as is commonly understood by one of skill in the art to which the disclosure belongs. All patents, patent applications, published applications and publications, databases, websites and other published materials referred to throughout the entire disclosure, unless noted otherwise, are incorporated by reference in their entirety. In the event that there is a plurality of definitions for terms, those in this section prevail. Where reference is made to a URL or other such identifier or address, it understood that such identifiers can change and particular information on the internet can come and go, but equivalent information can be found by searching the internet. Reference to the identifier evidences the availability and public dissemination of such information.

As used herein, the singular forms "a", "an" and "the" also include plural aspects (i.e. at least one or more than one) unless the context clearly dictates otherwise. Thus, for example, reference to "a polypeptide" includes a single polypeptide, as well as two or more polypeptides.

In the context of this specification, the term "about," is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, a "promoter" is used herein in its ordinary sense to refer to a nucleotide region comprising a sequence capable of initiating transcription of a downstream (3'-direction) coding sequence.

As used herein, "corresponding nucleotides" refer to nucleotides that occur at aligned loci. The sequences of related or variant polynucleotides are aligned by any method known to those of skill in the art. Such methods typically maximize matches (e.g. identical nucleotides at positions), and include methods such as using manual alignments and by using the numerous alignment programs available (for example, BLASTN, ClustlW, ClustlW2, EMBOSS, LALIGN, Kalign, etc) and others known to those of skill in the art. By aligning the sequences of polynucleotides, one skilled in the art can identify corresponding nucleotides. For example, by aligning the reverse, complement sequence of the AAV2 set forth in SEQ ID NO:1 and one or more other AAV serotypes, one of skill in the art can identify nucleotides within the other serotypes that correspond to the reverse, complement of nucleotides 4426-4530 of the AAV2 set forth in SEQ ID NO:1.

A "heterologous coding sequence" as used herein refers to nucleic acid sequence present in a polynucleotide, vector, or host cell that encodes a peptide or polypeptide, or a polynucleotide that itself has a function or activity, such as an antisense or inhibitory oligonucleotide, including antisense DNA and RNA (e.g. miRNA, siRNA, and shRNA), where the heterologous coding sequence is not naturally found in the polynucleotide, vector, or host cell, i.e. is non-native. For the purposes of the present invention, the heterologous coding sequence is also not naturally operably linked to a promoter of the invention.

An "enhancer" is used herein in its ordinary sense to refer to a nucleotide region comprising a sequence capable of increasing the level of transcription from a promoter.

As used herein, the term "operably-linked" or "operable-linkage" refers to a functional linkage between two elements, regardless of orientation or distance between the two elements, such that the function of one element is controlled or affected by the other element. For example, operable linkage with reference to a promoter and heterologous coding sequence means that the transcription of the heterologous coding sequence is under the control of, or driven by, the promoter. In another example, operable linkage with reference to an enhancer and promoter means that the enhancer increases the level of transcription driven by a promoter.

As used herein, a "vector" refers to a nucleic acid molecule capable of delivering a heterologous coding sequence contained within the vector into a host cell. Vectors can be episomal, i.e., do not integrate into the genome of a host cell, or can integrate into the host cell genome. Exemplary vectors include, but are not limited to, plasmids, cosmids, transposons, and viral vectors, such as AAV, lentiviral, retroviral, adenoviral, herpesviral, hepatitis viral vectors.

As used herein, the term "viral vector" refers to a vector that includes at least one element of viral origin and that has the capacity to be packaged into a recombinant virion. The viral vector and/or virion can be utilized for the purpose of transferring heterologous coding sequences into cells either in vitro or in vivo. Numerous forms of viral vectors are known in the art, and include AAV, lentiviral, retroviral, adenoviral, herpesviral, and hepatitis viral vectors.

As used herein, "adeno-associated viral vector" or AAV vector refers to a vector derived from an adeno-associated virus serotype, including without limitation, AAV1, AAV2, AAV3, AAV4, AAV5, AAV6, AAV7 and AAV8. AAV vectors can have one or more of the AAV wild-type genes deleted in whole or part, preferably the rep and/or cap genes, but retain functional flanking inverted terminal repeat (ITR) sequences. Functional ITR sequences are necessary for the rescue, replication and packaging of the recombinant AAV virion. Thus, an AAV vector is defined herein to include at least those sequences required in cis for replication and packaging (e.g., functional ITRs) of the virus.

The terms "recombinant AAV", "rAAV", "recombinant AAV virion", and "rAAV virion," are used interchangeably and refer to an infectious, replication-defective virus that includes an AAV capsid shell encapsidating a heterologous coding sequence flanked on both sides by AAV ITRs. Recombinant AAV virions can be produced from host cells into which an AAV vector has been introduced. To facilitate packaging of the AAV vector, additional AAV-derived coding sequences, such as the AAV rep and cap genes, are also introduced into the host cell.

The term "ITR" refers to an inverted terminal repeat at either end of the AAV genome. This sequence can form hairpin structures and is involved in AAV DNA replication and rescue, or excision, from prokaryotic plasmids. ITRs for use in the present invention need not be the wild-type nucleotide sequences, and may be altered, e.g., by the insertion, deletion or substitution of nucleotides, so long as the sequences provide for functional rescue, replication and packaging of rAAV.

The term "host cell" refers to a cell, such as a mammalian cell, that has introduced into it exogenous DNA, such as a vector. The term includes the progeny of the original cell into which the exogenous DNA has been introduced. Thus, a "host cell" as used herein generally refers to a cell that has been transfected or transduced with exogenous DNA.

As used herein, "isolated" with reference to a nucleic acid molecule means that the nucleic acid molecule is substantially free of cellular material or other contaminating proteins from the cells from which the nucleic acid molecule is derived, or substantially free from chemical precursors or other chemicals when chemically synthesized.

It will be appreciated that the above described terms and associated definitions are used for the purpose of explanation only and are not intended to be limiting.

TABLE 1

Brief Description of the Sequences

| SEQ ID NO: | Description |
|---|---|
| 1 | AAV2 genome |
| 2 | AAV1 genome |
| 3 | AAV3 genome |
| 4 | AAV4 genome |
| 5 | AAV5 genome |
| 6 | AAV6 genome |
| 7 | AAV7 genome |
| 8 | AAV7 genome |
| 9 | AAV2 46 nt promoter (reverse, complement sequence of 46 nt adjacent AAV2 3' ITR) |
| 10 | AAV2 75 nt promoter (reverse, complement sequence of 75 nt adjacent AAV2 3' ITR) |
| 11 | AAV2 105 nt promoter (reverse, complement sequence of 105 nt adjacent AAV2 3' ITR) |
| 12 | AAV2 133 nt promoter (reverse, complement sequence of 133 nt adjacent AAV2 3' ITR) |
| 13 | Vector insert for AAV2 105 nt promoter |
| 14 | Vector insert for AAV2 133 nt promoter |
| 15 | AAV7 121 nt promoter (reverse, complement sequence of 121 nt adjacent AAV7 3' ITR) |
| 16 | AAV7 149 nt promoter (reverse, complement sequence of 149 nt adjacent AAV7 3' ITR) |
| 17 | Vector insert for AAV7 121 nt promoter |
| 18 | Vector insert for AAV7 149 nt promoter |
| 19 | AAV5 121 nt promoter (reverse, complement sequence of 121 nt adjacent AAV5 3' ITR) |
| 20 | AAV5 149 nt promoter (reverse, complement sequence of 149 nt adjacent AAV5 3' ITR) |
| 21 | Vector insert for AAV5 121 nt promoter |
| 22 | Vector insert for AAV5 149 nt promoter |
| 23 | R105 |
| 24 | AAV2 5' ITR |
| 25 | AAV2 3' ITR |
| 36 | PCR primer OTC005f |
| 27 | PCR primer OTC004r |
| 28 | PCR primer eGFPf |
| 29 | PCR primer eGFPr |
| 30 | PCR primer GAPfl1 |
| 31 | PCR primer GAPfl2 |
| 32 | AAV2 ITR in vectors (reverse complement of SEQ ID NO: 25) |

Promoters

The present disclosure is predicated in part on the identification of a small, anti-sense region in the adeno-associated virus (AAV) genome that has promoter activity. Based upon this identification, a variety of promoters are provided herein which can be used to drive the expression of an operably linked heterologous coding sequence. Typically, expression is in a host cell of liver origin. The relatively small size of the promoter makes it particularly useful for the expression of larger heterologous coding sequences when using vectors with size restraints, such as viral vectors, including AAV vectors.

The promoters of the present disclosure comprise a sequence of nucleotides corresponding to the reverse, complement sequence of the region adjacent the 3' ITR in an AAV genome, or a sequence having at least 80%, 81%, 82%, 83%, 84%, 85%, 86%, 87%, 88%, 89%, 90%, 91%, 92%, 93%, 94%, 95%, 96%, 97%, 98%, 99% or more sequence identity thereto, wherein the promoter can drive transcription of an operably linked heterologous gene. In some examples, the promoters comprise a sequence of nucleotides corresponding to the reverse, complement sequence of the 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, or 135 nucleotides adjacent (or upstream of) the 3' ITR in an AAV genome, or a sequence having at least 80%, 81%, 82%, 83%, 84%, 85%, 86%, 87%, 88%, 89%, 90%, 91%, 92%, 93%, 95%, 96%, 97%, 98% or more sequence identity thereto, wherein the promoter can drive transcription of an operably linked heterologous gene. In some examples, the promoter has a sequence derived from the reverse, complement sequence of the region adjacent the 3' ITR in AAV serotype 1 (AAV1), AAV serotype 2 (AAV2), AAV serotype 3 (AAV3), AAV serotype 4 (AAV4), AAV serotype 6 (AAV6), AAV serotype 7 (AAV7), or AAV serotype 8 (AAV8).

Amongst the promoters provided herein are those that comprise a sequence corresponding to the 46 nucleotides adjacent the 3' ITR in an AAV genome, such as nucleotides 4485-4530 of the AAV2 set forth in SEQ ID NO:1 or corresponding nucleotides from another AAV genome, such as another AAV2 genome or an AAV1, AAV3, AAV4, AAV6 or AAV7 genome. For example, in some instances, the promoter comprises a sequence of nucleotides corresponding to the reverse, complement sequence of nucleotides 4514-4576 of the AAV7 set forth in SEQ ID NO:7. In further examples, the promoter comprises a sequence having at least 80%, 81%, 82%, 83%, 84%, 85%, 86%, 87%, 88%, 89%, 90%, 91%, 92%, 93%, 94%, 95%, 96%, 97%, 98% or more sequence identity to the reverse, complement sequence of nucleotides 4485-4530 of the AAV2 set forth in SEQ ID NO:1, i.e. the promoter comprises a sequence having at least 80%, 81%, 82%, 83%, 84%, 85%, 86%, 87%, 88%, 89%, 90%, 91%, 92%, 93%, 94%, 95%, 96%, 97%, 98% or more sequence identity to the sequence set forth in SEQ ID NO:9.

Amongst the promoters provided herein are those that comprise a sequence corresponding to the 75 nucleotides adjacent the 3' ITR in an AAV genome, such as nucleotides 4456-4530 of the AAV2 set forth in SEQ ID NO:1 or corresponding nucleotides from another AAV genome, such as another AAV2 genome or an AAV1, AAV3, AAV4, AAV6 or AAV7 genome. For example, in some instances, the promoter comprises a sequence of nucleotides corresponding to the reverse, complement sequence of nucleotides 4485-4576 of the AAV7 set forth in SEQ ID NO:7. In further examples, the promoter comprises a sequence having at least 80%, 81%, 82%, 83%, 84%, 85%, 86%, 87%, 88%, 89%, 90%, 91%, 92%, 93%, 94%, 95%, 96%, 97%, 98% or more sequence identity to the reverse, complement sequence of nucleotides 4456-4530 of the AAV2 set forth in SEQ ID NO:1, i.e. the promoter comprises a sequence having at least 80%, 81%, 82%, 83%, 84%, 85%, 86%, 87%, 88%, 89%, 90%, 91%, 92%, 93%, 94%, 95%, 96%, 97%, 98% or more sequence identity to the sequence set forth in SEQ ID NO:10.

Also provided herein are promoters that comprise a sequence corresponding to the 105 nucleotides adjacent the 3' ITR in an AAV genome, such as nucleotides 4426-4530 of the AAV2 set forth in SEQ ID NO:1 or corresponding nucleotides from another AAV genome, such as another AAV2 genome or an AAV1, AAV3, AAV4, AAV6 or AAV7 genome. For example, in some instances, the promoter comprises a sequence of nucleotides corresponding to the reverse, complement sequence of nucleotides 4455-4576 of the AAV7 set forth in SEQ ID NO:7, e.g. comprises a sequence of nucleotides set forth in SEQ ID NO:15. In further examples, the promoter comprises a sequence having at least 80%, 81%, 82%, 83%, 84%, 85%, 86%, 87%, 88%, 89%, 90%, 91%, 92%, 93%, 94%, 95%, 96%, 97%, 98% or more sequence identity to the reverse, complement sequence of nucleotides 4426-4530 of the AAV2 set forth in SEQ ID NO:1, i.e. the promoter comprises a sequence having at least 80%, 81%, 82%, 83%, 84%, 85%, 86%, 87%, 88%, 89%, 90%, 91%, 92%, 93%, 94%, 95%, 96%, 97%, 98% or more sequence identity to the sequence set forth in SEQ ID NO:11.

Also provided herein are promoters that comprise a sequence corresponding to the 133 nucleotides adjacent the 3' ITR in an AAV genome, such as nucleotides 4398-4530 of the AAV2 set forth in SEQ ID NO:1 or corresponding nucleotides from another AAV genome, such as another AAV2 genome or an AAV1, AAV3, AAV4, AAV6 or AAV7 genome. For example, in some instances, the promoter comprises a sequence of nucleotides corresponding to the reverse, complement sequence of nucleotides 4428-4576 of the AAV7 set forth in SEQ ID NO:7, e.g. comprises a sequence of nucleotides set forth in SEQ ID NO:16. In further examples, the promoter comprises a sequence having at least 80%, 81%, 82%, 83%, 84%, 85%, 86%, 87%, 88%, 89%, 90%, 91%, 92%, 93%, 94%, 95%, 96%, 97%, 98% or more sequence identity to the reverse, complement sequence of nucleotides 4398-4530 of the AAV2 set forth in SEQ ID NO:1, i.e. the promoter comprises a sequence having at least 80%, 81%, 82%, 83%, 84%, 85%, 86%, 87%, 88%, 89%, 90%, 91%, 92%, 93%, 94%, 95%, 96%, 97%, 98% or more sequence identity to the sequence set forth in SEQ ID NO:12.

In some example, the promoter comprises a sequence set forth in any one of SEQ ID NOs:9-12 or a sequence having at least 90% or 95% sequence identity thereto.

The promoters of the present disclosure typically include at least one transcription factor binding site, such as a hepatocyte nuclear factor (HNF) binding site. In some instances, the promoter contains 2, 3, 4 or more HNF binding sites. The HNF binding sites can be selected from HNF1, HNF1α-c and HNF4α binding sites or a combination thereof.

The promoters of the present invention may also include, or be linked to, nucleotides having a sequence corresponding to all or a portion of an AAV inverted terminal repeat (ITR), or a sequence having at least 80%, 81%, 82%, 83%, 84%, 85%, 86%, 87%, 88%, 89%, 90%, 91%, 92%, 93%, 94%, 95%, 96%, 97%, 98% sequence identity thereto. Exemplary ITRs include nucleotides 1-145 or 4531-4675 of the AAV2 genome set forth in SEQ ID NO:1; or corresponding nucleotides in another AAV genome, such as nucleotides 1-145 or 4531-4675 of the AAV1 genome set forth in SEQ ID NO:2; nucleotides 1-146 or 4580-4726 of the AAV3 genome set forth in SEQ ID NO:3; nucleotides 1-145 or 4624-4767 of the AAV4 genome set forth in SEQ ID NO:4; nucleotides 1-145 or 4539-4683 of the AAV6 genome set forth in SEQ ID NO:6; or nucleotides 1-145 or 4577-4721 of the AAV7 genome set forth in SEQ ID NO:7. In one example, the promoter includes or is linked to an AAV2 ITR, such as one having a sequence of nucleotides set forth in SEQ ID NO:24, 25 or 32, or a sequence having at least 80%, 81%, 82%, 83%, 84%, 85%, 86%, 87%, 88%, 89%, 90%, 91%, 92%, 93%, 94%, 95%, 96%, 97%, 98% sequence identity thereto.

Most typically, the promoters of the present disclosure have a size of 300 nucleotides or less, or 290, 280, 270, 260, 250, 240, 230, 220, 210, 200, 190, 180, 170, 160, 150, 140, 130, 120, 115, 110, 105, 100, 95, 90, 85, 80, 75, 70, 65, 60, 55, 50 or 45 nucleotides or less. In particular embodiments, the promoter is 120 nucleotides or less. In other embodiments, the promoter is 105 nucleotides or less. In still further embodiments, the promoter is 75 nucleotides or less.

The promoters of the present invention can be provided as an isolated polynucleotide or part of an isolated polynucleotide. Accordingly, the present disclosure also provides isolated polynucleotides comprising a promoter described herein. As would be appreciated by those skilled in the art, the isolated polynucleotides may further contain one or more additional elements or sequences, such as any described herein or known in the art.

Spacers

The promoters of the present disclosure can be linked at their 3' end to nucleotide spacer sequences (i.e. the spacer sequence is downstream of the promoter) so that, when further linked to a heterologous coding sequence, the distance from the start of the promoter (i.e. the 5' end of the promoter) and the ATG start codon of the heterologous coding sequence is sufficient to allow the transcription factors and RNA polymerase to bind, form the transcription complex and initiate transcription prior to or at the ATG start codon.

In some embodiments, the total length of the promoter and spacer is 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135 nucleotides or more (i.e. the distance between the start of the promoter and the ATG start codon of the heterologous coding sequence can be 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135 nucleotides or more). Thus, the spacer may be, for example, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 nucleotides or more. As would be understood by those skilled in the art, the sequence of the spacer is not critical. The sequence of the spacer may be a random, artificial sequence, a sequence derived from AAV or a sequence derived from another source.

Heterologous Coding Sequences

The promoters of the present disclosure may be operably linked to one or more heterologous coding sequences. Accordingly, provided are isolated polynucleotides (i.e. nucleic acid molecules) comprising a promoter of the present disclosure operably linked to a heterologous coding sequence. In some embodiments, there is a spacer, as described above, positioned between the promoter and heterologous coding sequence. The heterologous coding sequences can encode a peptide or polypeptide, such as a therapeutic peptide or polypeptide, or can encode a polynucleotide or transcript that itself has a function or activity, such as an antisense or inhibitory oligonucleotide, including antisense DNA and RNA (e.g. miRNA, siRNA, and shRNA). As would be appreciated, the nature of the heterologous coding sequence is not essential to the present disclosure, provided the sequence is operably linked to the promoter to facilitate expression in a host a cell. In particular embodiments, the promoters and operably linked heterologous coding sequence(s) described herein will be used in gene therapy. In still further embodiments, the heterologous coding sequence will be primarily expressed in the liver or in liver-derived cells. In some instances, the product of the heterologous coding sequence may also be secreted into the bloodstream after expression.

In particular examples, the heterologous coding sequence encodes a peptide or polypeptide, or polynucleotide, whose expression is of therapeutic use, such as, for example, for the treatment of a disease or disorder. For example, expression of a therapeutic peptide or polypeptide may serve to restore or replace the function of the endogenous form of the peptide or polypeptide that is defective (i.e. gene replacement therapy). In other examples, expression of a therapeutic peptide or polypeptide, or polynucleotide, from the heterologous coding sequence serves to alter the levels and/or activity of one or more other peptides, polypeptides or polynucleotides in the host cell. Thus, according to particular embodiments, the expression of a heterologous coding sequence from a promoter described herein in a host cell can be used to provide a therapeutic amount of a peptide, polypeptide or polynucleotide to ameliorate the symptoms of a disease or disorder. In particular embodiments, expression is in a liver cell and treatment is for a disease or disorder associate with the liver, including diseases or disorders that affect liver cells, and diseases or disorders that are associated with a polypeptide or polynucleotide expressed in liver cells.

In some examples, the heterologous coding sequence that encodes a therapeutic peptide, polypeptide, or polynucleotide is involved in or affects the immune response, hematopoiesis, inflammation, cell growth and proliferation, cell lineage differentiation, and/or the stress response. Non-limiting examples of heterologous coding sequences encoding therapeutic polypeptides include factor VIII, factor IX, factor VII, factor X, von Willebrand factor, erythropoietin (EPO), interferon-α, interferon-β, interferon-γ, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C-X-C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumor necrosis factor (TNF), afamin (AFM), α1-antitrypsin, α-galactosidase A, α-L-iduronidase, ATP7b, ornithine transcarbamoylase, phenylalanine hydroxylase, lipoprotein lipase, apoliproteins, low-density lipoprotein receptor (LDL-R), albumin, glucose-6-phosphatase, transgenes encoding antibodies, nanobodies, anti-viral dominant-negative proteins, and fragments, subunits or mutants thereof.

Enhancers

As described herein, the region comprising the promoters of the present disclosure also has enhancer activity, i.e. can increase transcription driven by an operably linked promoter. Thus, provided herein are enhancers that can be used to increase transcription driven by an operably linked promoter. Accordingly, therefore, the enhancers can be used to increase the expression of a heterologous coding sequence that is operably linked to a promoter that is operably linked to the enhancer, compared to expression of the heterologous coding sequence from the promoter when the enhancer is not present. The enhancers need not be in any specified position in a nucleic acid molecule in relation to the promoter, transcriptional start site, or transcriptional termination site, provided it is operably linked. An enhancer of the present disclosure is considered to be operably linked to a specific promoter if the presence of the enhancer increases transcription driven by that promoter.

Enhancers of the present disclosure include those that comprise a sequence corresponding to the 105 nucleotides adjacent the 3' ITR in an AAV genome, such as nucleotides 4426-4530 of the AAV2 set forth in SEQ ID NO:1 (i.e. the sequence set forth in SEQ ID NO:11) or corresponding nucleotides from another AAV genome, such as another AAV2 genome or an AAV1, AAV3, AAV4, AAV6 or AAV7 genome. In further examples, the enhancer comprises a sequence having at least 80%, 81%, 82%, 83%, 84%, 85%, 86%, 87%, 88%, 89%, 90%, 91%, 92%, 93%, 94%, 95%, 96%, 97%, 98% or more sequence identity to the reverse, complement sequence of nucleotides 4426-4530 of the AAV2 set forth in SEQ ID NO:1, i.e. the promoter comprises a sequence having at least 80%, 81%, 82%, 83%, 84%, 85%, 86%, 87%, 88%, 89%, 90%, 91%, 92%, 93%, 94%, 95% or more sequence identity to the sequence set forth in SEQ ID NO:11.

As noted above, the enhancer can be in any orientation with respect to an operably linked promoter. Thus, the enhancer also can comprise the reverse, complement sequence of the 105 nucleotides adjacent the 3' ITR in an AAV genome, such as nucleotides 4426-4530 of the AAV2 set forth in SEQ ID NO:1, i.e. SEQ ID NO:11, or the reverse, complement of a sequence having at least 80%, 81%, 82%, 83%, 84%, 85%, 86%, 87%, 88%, 89%, 90%, 91%, 92%, 93%, 94%, 95% or more sequence identity to the sequence set forth in SEQ ID NO:11.

The enhancers can contain more or fewer nucleotides than those corresponding to the 105 nucleotides adjacent the 3' ITR in an AAV genome (e.g. nucleotides 4426-4530 of the AAV2 set forth in SEQ ID NO:1, i.e. the sequence set forth in SEQ ID NO:11) or the complement sequence thereof, provided the enhancer retains its enhancing activity, i.e. can increase transcription driven by an operably linked promoter. Thus, for example, in some embodiments, the enhancer can include up to 105 nucleotides of the sequence corresponding to nucleotides 4426-4530 of the AAV2 set forth in SEQ ID NO: 1. Most typically, the enhancers of the present disclosure have a size of 300 nucleotides or less, or 290, 280, 270, 260, 250, 240, 230, 220, 210, 200, 190, 180, 170, 160, 150, 140, 130, 120, 115, 110, 105, 100, 95, 90, 85, 80, 75, 70, 65, 60, 55, 50 or 45 nucleotides or less. In particular embodiments, the enhancer is 105 nucleotides or less.

Enhancers of the present disclosure can be operably linked to any promoter. Thus, provided herein are nucleic acid molecules (or polynucleotides) comprising an enhancer of the present invention that is operably linked to a promoter. The promoter may be an AAV promoter, such as the p5, p19 or p40 promoter or may be derived from other sources, i.e. in some instances, the promoter is not an AAV promoter. Furthermore, the promoter may be constitutive or inducible, and/or may be tissue-specific, such as liver-specific. Examples of constitutive promoters include, without limitation, the retroviral Rous sarcoma virus (RSV) LTR, the cytomegalovirus (CMV) promoter, the SV40 promoter, the dihydrofolate reductase promoter, the (β-actin promoter, the phosphoglycerol kinase (PGK) promoter, and the EF1α promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Non-limiting examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system; the ecdysone insect promoter, the tetracycline-repressible system, the tetracycline-inducible system, the RU486-inducible system and the rapamycin-inducible system. Still other types of inducible promoters which may be useful in this context are those which are regulated by a specific physiological state, e.g., temperature, acute phase, a particular differentiation state of the cell, or in replicating cells only. In some embodiments, tissue specific promoters are used. Non-limiting examples of such promoters include the liver-specific thyroxin binding globulin (TBG) promoter, human alpha 1-antitrypsin (hAAT) promoter, insulin promoter, glucagon promoter, somatostatin promoter, pancreatic polypeptide (PPY) promoter, synapsin-1 (Syn) promoter, creatine kinase (MCK) promoter, mammalian desmin (DES) promoter, a α-myosin heavy chain (a-MHC) promoter, a cardiac Troponin T (cTnT) promoter, beta-actin promoter, and hepatitis B virus core promoter. In particular embodiments, the promoter is not the strong liver specific promoter (LSP) containing the apolipoprotein E/human α1-antitrypsin enhancer/promoter elements (Cunningham et al. (2008) Mol Ther. 16(6): 1081-1088). The selection of an appropriate promoter is well within the ability of one of ordinary skill in the art. Furthermore, 1, 2, 3, 4, 5, 6, 7 or more enhancers may be operably linked to a promoter.

Vectors

The present disclosure also provides vectors comprising a promoter and/or enhancer described herein. The promoters of the present disclosure can be included in any suitable vector for the expression of one or more heterologous coding sequences from the promoter. The enhancers of the present disclosure can be included in any suitable vector for the expression of one or more heterologous coding sequences from a promoter that is operably linked to the enhancer. The vectors can be episomal vectors (i.e., that do not integrate into the genome of a host cell), or can be vectors that integrate into the host cell genome. Exemplary vectors include, but are not limited to, plasmids, cosmids, and viral vectors, such as AAV, lentiviral, retroviral, adenoviral, herpesviral, hepatitis viral vectors.

Typically, vectors of the present disclosure also contain one or more restriction enzyme sites positioned downstream of the promoter to facilitate the insertion of a heterologous coding sequence such that the heterologous coding sequence is operably linked to the promoter. In some examples, the vectors comprise a heterologous coding sequence operably linked to the promoter. In further examples, the vectors comprise two or more heterologous coding sequences operably linked to the promoter. In instances where the vector comprises an enhancer of the present disclosure, the enhancer may be operably linked to a promoter, and the promoter may be operably linked to one or more heterologous coding sequences.

In some embodiments, the promoters described herein are the only promoters contained in the vectors of the present invention that can drive the expression of any heterologous coding sequence other than a sequence encoding a selectable marker (e.g. an antibiotic resistance gene) and/or reportable marker (e.g. a fluorescent marker). Accordingly, in some instances, the vectors of the present disclosure may contain one or more other promoters, but those promoters drive the expression of a selectable marker and/or a reportable marker and not a heterologous coding sequence that encodes a polypeptide, peptide or polynucleotide of interest, such as a therapeutic polypeptide, peptide or polynucleotide.

Vectors suitable for use in mammalian cells are widely described and well-known in the art. Those skilled in the art would appreciate that vectors of the present invention that comprise a promoter described herein will also contain additional sequences and elements useful for the replication of the vector in prokaryotic and/or eukaryotic cells, selection of the vector and the expression of a heterologous sequences in a variety of host cells. For example, the vectors of the present disclosure can include a prokaryotic replicon (that is, a sequence having the ability to direct autonomous replication and maintenance of the vector extrachromosomally in a prokaryotic host cell, such as a bacterial host cell. Such replicons are well known in the art. In some embodiments, the vectors can include a shuttle element that makes the vectors suitable for replication and integration in both prokaryotes and eukaryotes. In addition, vectors may also include a gene whose expression confers a detectable marker such as a drug resistance gene, which allows for selection and maintenance of the host cells. Vectors may also have a reportable marker, such as gene encoding a fluorescent or other detectable protein.

The vectors can also include transcriptional enhancers, translational signals, and transcriptional and translational termination signals. Examples of transcriptional termination signals include, but are not limited to, polyadenylation signal sequences, such as bovine growth hormone (BGH) poly(A), SV40 late poly(A), rabbit beta-globin (RBG) poly (A), thymidine kinase (TK) poly(A) sequences, and any variants thereof. In some embodiments, the transcriptional termination region is located downstream of the posttranscriptional regulatory element. In some embodiments, the transcriptional termination region is a polyadenylation signal sequence.

The vectors can include various posttranscriptional regulatory elements to increase the expression level of a heterologous coding sequence. In some embodiments, the posttranscriptional regulatory element can be a viral posttranscriptional regulatory element. Non-limiting examples of viral posttranscriptional regulatory element include woodchuck hepatitis virus posttranscriptional regulatory element (WPRE), hepatitis B virus posttranscriptional regulatory element (HBVPRE), RNA transport element, and any variants thereof. The RTE can be a rev response element (RRE), for example, a lentiviral RRE. A non-limiting example is bovine immunodeficiency virus rev response element (RRE). In some embodiments, the RTE is a constitutive transport element (CTE). Examples of CTE include, but are not limited to Mason-Pfizer Monkey Virus CTE and Avian Leukemia Virus CTE.

A signal peptide sequence can also be included in the vector to provide for secretion of a polypeptide encoded by a heterologous coding sequence from a mammalian cell. Examples of signal peptides include, but are not limited to, the endogenous signal peptide for HGH and variants thereof; the endogenous signal peptide for interferons and variants thereof, including the signal peptide of type I, II and III interferons and variants thereof; and the endogenous signal peptides for known cytokines and variants thereof, such as the signal peptide of erythropoietin (EPO), insulin, TGF-β1, TNF, IL1-α, and IL1-β, and variants thereof. Typically, the nucleotide sequence of the signal peptide is located immediately upstream of the heterologous coding sequence (e.g., fused at the 5' of the coding region of the protein of interest) in the vector. In instances where the vector does not include a heterologous coding sequence, a signal sequence can be included in the vector downstream of the promoter so that upon insertion of a heterologous coding sequence, the signal peptide is in-frame with the heterologous coding sequence.

In further examples, the vectors can contain a regulatory sequence that allows, for example, the translation of multiple proteins from a single mRNA. Non-limiting examples of such regulatory sequences include internal ribosome entry site (IRES) and 2A self-processing sequence, such as a 2A peptide site from foot-and-mouth disease virus (F2A sequence).

In particular examples, the vectors of the present disclosure are AAV vectors. AAV vectors are well-known in the art and may be based on AAV of any serotype. AAV vectors of the present invention can comprise functional AAV ITRs flanking a promoter described herein. Accordingly, the AAV vectors have a 5' ITR upstream of the promoter and a 3' ITR downstream of the promoter. Typically, the promoter of the present invention is the only promoter flanked by the ITRs. In some examples, the promoter is operably linked to a heterologous coding sequence. In other examples, the promoter is upstream of one or more restriction enzyme sites to facilitate the insertion of a heterologous coding sequence, such that the heterologous coding sequence is operably linked to the promoter. Any other additional transcriptional enhancers, or transcriptional or translational termination signals may also be included, provided the ITRs flank the entire sequence providing the promoter, optional heterologous coding sequence, and optional transcriptional/translational enhancers and termination sequences. Most typically, a promoter of the present disclosure is the only promoter flanked by the ITRs.

AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV1, AAV2, AAV3, AAV4, AAV5, AAV6, AAV7 and AAV8, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of a heterologous coding sequence from a host cell genome or vector, and to allow integration of the DNA molecule into the recipient cell genome when AAV Rep gene products are present in the cell.

The nucleotide sequences of AAV ITR regions are well known in the art. Exemplary AAV ITRs useful for the AAV vectors of the present disclosure include those set forth as nucleotides 1-145 or 4531-4675 of the AAV2 genome set forth in SEQ ID NO:1; nucleotides 1-145 or 4531-4675 of the AAV1 genome set forth in SEQ ID NO:2; nucleotides 1-145 or 4577-4721 of the AAV7 genome set forth in SEQ ID NO:7; nucleotides 1-145 or 4574-4718 of the AAV1 genome set forth in SEQ ID NO:1; nucleotides 1-146 or 4580-4726 of the AAV3 genome set forth in SEQ ID NO:3; nucleotides 1-145 or 4624-4767 of the AAV4 genome set forth in SEQ ID NO:4; or nucleotides 1-145 or 4539-4683 of the AAV6 genome set forth in SEQ ID NO:6. In one example, the ITRs in the AAV vectors of the present invention have a sequence of nucleotides set forth in SEQ ID NO:24, 25 or 32, or a sequence having at least 80%, 81%, 82%, 83%, 84%, 85%, 86%, 87%, 88%, 89%, 90%, 91%, 92%, 93%, 94%, 95%, 96%, 97%, 98% sequence identity thereto.

The AAV vectors of the present invention can be constructed using known techniques, including, without limitation, the standard techniques of restriction endonuclease digestion, ligation, transformation, plasmid purification, in vitro or chemical synthesis of DNA, and DNA sequencing. In one example, an AAV genome that has had the major AAV open reading frames, Cap and Rep, excised can be inserted into a vector. Other portions of the AAV genome can also be deleted, so long as a sufficient portion of the ITRs remain to allow for replication and packaging functions. Alternatively, AAV ITRs can be excised from the viral genome, from an AAV vector containing the ITRs, or synthesized, and inserted into a vector using standard techniques. A promoter described herein can then be inserted between the ITRs, and any additional sequences also included.

Recombinant Viruses

Also provided are recombinant virions, including recombinant AAV, lentiviral, retroviral, adenoviral, herpesviral, hepatitis viral virions, produced using the viral vectors described herein. Accordingly, the recombinant virions can thus contain a promoter or enhancer of the invention. Most typically, the recombinant virions also comprise a heterologous coding sequence operably linked to the promoter. As will be understood by those skilled in the art, in most instances, not all of the nucleotides of the viral vector will be packaged into the recombinant virus. For example, in the case of AAV vector packaging, only the ITRs and the nucleotides flanked by the ITRs, including the promoter as well as any other sequences downstream of the promoter and upstream of the 3' ITR, such as a heterologous coding sequence, will be packaged into the recombinant AAV. The recombinant virions can be used to deliver the heterologous coding sequence to a host cell for expression in that cell.

Methods for packaging viral vectors to produce recombinant virions are well known in the art, and any such method can be used to produce recombinant virions containing a promoter of the present disclosure. In particular examples, the recombinant virion is a recombinant AAV virion produced by packaging an AAV vector described herein. In some embodiments, methods for producing a recombinant AAV include introducing into a packaging cell line an AAV vector described herein, helper functions for generating a productive AAV infection, and AAV cap and rep genes, and recovering a recombinant AAV from the supernatant of the packaging cell line. Various types of cells can be used as the packaging cell line. For example, packaging cell lines that can be used include, but are not limited to, HEK 293 cells, HeLa cells, and Vero cells, for example as disclosed in US20110201088.

The helper functions may be provided by one or more helper plasmids or helper viruses comprising adenoviral helper genes. Non-limiting examples of the adenoviral helper genes include E1A, E1B, E2A, E4 and VA, which can provide helper functions to AAV packaging. In some embodiments, the AAV cap genes are present in a plasmid. The plasmid can further comprise an AAV rep gene. It is contemplated that the cap genes and/or rep gene from any AAV serotype (including, but not limited to, AAV1, AAV2, AAV4, AAV5, AAV6, AAV7, AAV8, AAV9, and any variants thereof) can be used to produce the recombinant AAV disclosed herein.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US20110201088, helper vectors pHELP (Applied Viromics). A skilled artisan will appreciate that any helper virus or helper plasmid of AAV that can provide adequate helper function to AAV can be used herein.

In some instances, recombinant AAV is produced by using a cell line that stably expresses some of the necessary components for AAV virion production. For example, a plasmid (or multiple plasmids) comprising AAV rep and cap genes, and a selectable marker, such as a neomycin resistance gene, can be integrated into the genome of a cell (the packaging cells). The packaging cell line can then be co-infected with a helper virus (e.g., adenovirus providing the helper functions) and an AAV vector described herein. The advantages of this method are that the cells are selectable and are suitable for large-scale production of the recombinant AAV. As another non-limiting example, adenovirus or baculovirus rather than plasmids can be used to introduce rep and cap genes into packaging cells. As yet another non-limiting example, both the AAV vector and the rep-cap genes can be stably integrated into the DNA of producer cells, and the helper functions can be provided by a wild-type adenovirus to produce the recombinant AAV.

As will be appreciated by a skilled artisan, any method suitable for purifying AAV can be used in the embodiments described herein to purify the recombinant AAV, and such methods are well known in the art. For example, the recombinant AAV can be isolated and purified from packaging cells and/or the supernatant of the packaging cells. In some embodiments, the AAV is purified by separation method using a CsCl gradient. In other embodiments, AAV is purified as described in US20020136710 using a solid support that includes a matrix to which an artificial receptor or receptor-like molecule that mediates AAV attachment is immobilized.

Host Cells

Also provided herein are host cells comprising a vector or recombinant virion of the present disclosure. In some instances, the host cells are used to amplify, replicate, package and/or purify a vector or recombinant virion. In other examples, the host cells are used to express a heterologous coding sequence under the control of a promoter of the present disclosure or under the control of a promoter operably linked to an enhancer of the present invention. Thus, the present disclosure also contemplates methods for the expression of a heterologous coding sequence, in which a nucleic acid molecule containing a heterologous coding sequence under the control of a promoter of the present invention is introduced into a host cell. In other examples, contemplated are methods for the expression of a heterologous coding sequence, in which a nucleic acid molecule containing a heterologous coding sequence under the control of a promoter operably linked to an enhancer of the present disclosure is introduced into a host. The nucleic acid molecule may be a vector, such as a plasmid or viral vector (e.g. an AAV vector), or may be, for example, contained within a recombinant virion. Those skilled in the art would appreciate the conditions under which the nucleic acid molecule can be introduced into a host cell and the conditions that support or facilitate expression of the heterologous sequence within the cell. Furthermore, the methods may be in vitro, ex vivo or in vivo.

Exemplary host cells include prokaryotic and eukaryotic cells. In some instances, the host cell is a mammalian host cell. In instances where the cells are used to package a viral vector described herein, the cells may also be transfected with one or more plasmids or infected with one or more viruses that provide the necessary helper and accessory molecules for packaging. In further example, the host cells may stably express, such as from the genome, one or more helper and accessory molecules. It is well within the skill of a skilled artisan to select an appropriate host cell for the amplification, replication, packaging and/or purification of a vector or recombinant virion of the present invention. Exemplary mammalian host cells include, but are not limited to, HEK-293 cells, HeLa cells, Vero cells, HUH7 cells, and HepG2 cells. In particular examples, for expression of a heterologous coding sequence from a promoter described herein, the host cell is a liver-derived cell, such as, for example, HUH7 and HepG2 cells.

Pharmaceutical Compositions and Methods of Administration

Also provided are pharmaceutical compositions comprising the vectors or recombinant virions disclosed herein and a pharmaceutically acceptable carrier. The compositions can also comprise additional ingredients such as diluents, stabilizers, excipients, and adjuvants.

The carriers, diluents and adjuvants can include buffers such as phosphate, citrate, or other organic acids; antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

Titers of recombinant virions to be administered will vary depending on, for example, the particular recombinant virus, the disease or disorder to be treated, the mode of administration, the treatment goal, the individual to be treated, and the cell type(s) being targeted, and can be determined by methods well known to those skilled in the art. Although the exact dosage will be determined on an individual basis, in most cases, typically, recombinant viruses of the present invention can be administered to a subject at a dose of between $1\times10^{10}$ genome copies of the recombinant virus per kg of the subject and $1\times10^{14}$ genome copies per kg.

The vectors or recombinant viruses disclosed herein can be administered to a subject (e.g., a human) in need thereof, such as subject with a disease or condition amendable to treatment with a protein, peptide or polynucleotide encoded by a heterologous coding sequence described herein. Diseases or conditions that may be treated by administration of recombinant virus described herein include, but are not limited to, liver-associated diseases, including alpha 1-antitrypsin deficiency, type I tyrosinemia, Progressive Familial Intrahepatic Cholestasis type III, Wilsons' disease, Crigler-Najjar syndrome type I, ornithine transcarbamylase (OTC) deficiency, type IIa familial hypercholesterolemia, coagulation disorders (e.g. hemophilia A and B, afibrogenemiahe-mophilia, von Willebrand's disease), viral infections of the liver (e.g. hepatitis virus infections, including hepatitis C virus), and liver cancers.

The route of the administration is not particularly limited. For example, a therapeutically effective amount of the recombinant viruses can be administered to the subject by via, for example, intramuscular, intravaginal, intravenous, intraperitoneal, subcutaneous, epicutaneous, intradermal, rectal, intraocular, pulmonary, intracranial, intraosseous, oral, buccal, or nasal routes. The recombinant viruses can be administrated as a single dose or multiple doses, and at varying intervals.

In order that the invention may be readily understood and put into practical effect, particular preferred embodiments will now be described by way of the following non-limiting examples.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLES

Example 1

Experimental Procedures

AAV Vectors

AAV vectors were produced using standard molecular biological techniques. The AAV vector pAM-LSP1-eGFP encoding green fluorescent protein under the transcriptional control of the heterologous promoter containing one copy of the hAAT promoter and two copies of the ApoE enhancer element was previously reported by Cunningham et al. (Mol. Therapy (2008) 16:1081-1088). This construct was used to produce an AAV vector (pAM-2/1-46+65BS-GFP-3'UTR) which lacked the hAAT/ApoE heterologous promoter but which contained the 3' untranslated region (3'UTR) sequence from murine ornithine transcarbamylase (OTC). This vector was produced as follows.

The RNA isolated from mouse liver using Trizol (Invitrogen) was reverse transcribed using SuperScript™ III First-Strand Synthesis kit (Invitrogen) according to the manufacturer's instructions. PCR primers OTC005f 5'-GTATCGATGTGCTCCAGAAGCCAAAG-3'; SEQ ID NO:26) and OTC004r (5'-GATGAATAAAAAAAATAGA-TATCGATGGC-3'; SEQ ID NO:27) were designed against GenBank consensus sequence (NM_008769.3) for ornithine transcarbamylase (OTC) to PCR amplify the 3'UTR of OTC using Taq DNA polymerase. After gel purification, the PCR fragment was cloned into pGEM-T-Easy and the 3'UTR sequence was confirmed by Sanger sequencing. The 3'UTR was sub-cloned from pGEM-T-easy by ClaI restriction digest (Cla I restriction recognition sites were incorporated into OTC005f/OTC004r primer sequences). The 5' and 3' overhangs of the DNA fragment were removed and ligated between the stop codon of the eGFP transgene and the WPRE sequence in EcoRV-digested pAM-LSP1-eGFP. The hAAT/ApoE promoter sequence was removed by SacI/XbaI digestion, 5' and 3' overhangs of the DNA fragment were removed and the linearised plasmid was ligated.

In order to modify pAM-2/1-46+65BS-GFP-3'UTR to substitute alternative promoter regions in place of 2/1-46+65BS, a 5' AAV ITR sequence was synthesised (Genscript)

with NotI and XbaI recognition sites positioned downstream of the 5' ITR. The insert was sub-cloned into pAM2/1-46+ 65BS-GFP to replace the 5' ITR. Inserts of interest were synthesised (Genscript) with flanking NotI/XbaI sites for sub-cloning to the AAV construct.

Packaging of AAV Vectors

AAV vectors were packaged into AAV capsids by transfection using HEK-293 and a helper virus-free system as previously described (Xiao Samulksi (1998) Journal of Virology 72(3):2224-32). Briefly, HEK-293 were plated in Dulbecco's modified DMEM supplemented with 10% FBS (complete DMEM) at $4\times10^6$ cells per 100 mm diameter plate and incubated at 37° C. overnight in a humidified 5% $CO_2$ environment. The next day, the media in each dish was replaced with fresh media. A calcium phosphate transfection mix was prepared containing plasmids encoding adenovirus helper functions (pXX6, 6 μg), AAV capsid proteins, the AAV vector (1 μg), and pXX2 (serotype 2; courtesy of Jude Samulski, University of North Carolina), p5E18-VD2/8 (serotype 8; courtesy of James M. Wilson, University of Pennsylvania) and pAAV-DJ (DJ capsid; courtesy of Dr Leszek Lisowski, Salk Institute, San Diego). The transfection mix was dispensed to plates, which were then incubated overnight at 37° C. in a humidified 5% $CO_2$ environment. After a medium change with fresh complete DMEM at 18 hours post-transfection, cells were harvested 48 hours post-transfection and pelleted at 400×g for 10 minutes. Cells containing vectors packaged in AAV capsid serotype 8 or DJ capsid were resuspended at 1 mL per plate in buffer (100 mM NaCl, 2 mM $MgCl_2$, 10 mM Tris.HCl (pH8)) and stored at −80° C. before purification. Cells containing vectors packaged in AAV capsid serotype 2 were resuspended at 1 mL PBS buffer (without calcium and magnesium) per two plates and subjected to three rounds of freeze thaw cycles followed by centrifugation at 300×g for 10 minutes. Recombinant AAV-containing supernatants (crude lysates) were removed and stored at −80° C.

Purification of rAAV for In Vivo Delivery

HEK-293 cells containing rAAV were subjected to three freeze-thaw cycles. Cellular debris was pelleted by centrifugation at 3000×g for 10 minutes and supernatant was treated with Benzonase (Sigma) at 50 U/mL at 37° C. for 30 minutes to remove unencapsulated DNA. Centrifugation at 3000×g for 10 minutes was followed by two precipitation steps, the first using a one-third volume of ice-cold saturated $(NH_4)_2SO_4$ in PBS (pH 7.0) and incubation on ice for 10 minutes. After centrifugation at 3000×g for 15 minutes, the supernatant was retained and subjected to a second precipitation with two-third volume of ice-cold saturated $(NH_4)_2SO_4$ in PBS (pH 7.0) and incubation on ice for 10 minutes. The final precipitation step was followed by centrifugation at 12,000×g for 15 minutes. The rAAV-containing pellet was resuspended in 20 mL of CsCl solution in PBS (d=1.37, pH7.5) and divided into two 10 mL centrifuge tubes. Using a pasteur pipette, 1 mL of CsCl (d=1.5) was added beneath each suspension, which were then subjected to 150,000×g in a Beckman SW41 rotor at 16° C. for 36-48 hours.

The upper-most 2 mLs of each CsCL gradient were discarded and 1 mL fractions were collected from the bottom of each tube after piercing with a 19 gauge needle. Virus containing fractions were identified by PCR, pooled and dialysed against PBS (with calcium and magnesium) using a Slide-A-Lyzer Dialysis Cassette (10,000 MWCO, Pierce). A final dialysis was performed at 4° C. against 20 mM Tris (pH8.0)/1 mM $MgCl_2$/150 mM NaCl/5% glycerol for 4 hours to overnight.

The purified rAAV was subjected to a final concentration step using a Vivaspin-20 column (100,000 MWCO, Sartorius) which was centrifuged at 3000×g/4° C. until the volume was reduced to less than 1 mL. The titre of the virus stock was determined using quantitative PCR.

Titration of Packaged AAV Vectors by Quantitative PCR

Packaged AAV vector in rAAV in crude lysates or CsCl purified virus was quantitated by quantitative PCR (qPCR). A 25 μL reaction mix was prepared containing 1× Sybr Green PCR buffer (Takara), 0.5 μM of eGFP-specific forward primer (eGFPf-5'-TCAAGATCCGCCACAACATC-3'; SEQ ID NO:28) and 0.5 μM of eGFP-specific reverse primer (eGFPr-5'-TTCTCGTTGGGGTCTTTGCT-3'; SEQ ID NO:29) and 5 μL of vector diluted (1:2000-1:10,000) in 10% TE buffer. Known quantities of linearised plasmid DNA encoding eGFP were included in each run to generate a standard curve and permit quantitation of vector genomes. Tubes were cycled in a Rotorgene 2000 or Rotor GENE-Q thermal cycler (QIAGEN) at 95° C.-30 seconds followed by 40 cycles of 95° C.-5 sec, 58° C.-15 sec, 72° C.-20 sec, and 86° C.-15 sec. Melt curves (60-99° C.) were determined at completion of the reaction to ensure a single PCR product was specifically synthesised. All samples were analysed in duplicate. Averages were determined and the number of vector genomes per mL were calculated from the standard curve.

Transduction of Cells with rAAV and Analysis for GFP and Provirus

HEK-293, A549, MRC5, Caco-2, HeLa, SK-UT-1, K562, HUH7 and BWTG3 cells were cultured in complete medium (DMEM containing 10% fetal bovine serum (FBS)) and passaged using trypsin. Cells were plated to 12-well plates in complete DMEM at $2\times10^5$ cells per well and incubated overnight at 37° C. in a humidified-5% $CO_2$ incubator. The next morning, $2\times10^9$ vg of each rAAV stock was diluted in 0.5 mL of complete DMEM and added to the cells (MOI=10,000). After 48 hours incubation, cells were harvested using trypsin and analysed on a FACSCanto fluorescent activated cell sorter (BD) for GFP expression. Remaining cells were pelleted in eppendorf tubes at 400×g, snap frozen in liquid nitrogen and stored at −80° C.

DNA was extracted from frozen cells using a QIAamp DNA Blood mini kit (QIAGEN) and 50 ng DNA was analysed for vector provirus using qPCR (described above) to detect the GFP transgene and normalised against GAPDH copy number ascertained in a separate qPCR. This was performed using GAPDH specific PCR primers (GAPfl1 forward primer 5'-GCTCTCTGCTCCTCCTGTTCG-3' (SEQ ID NO:30); and GAPr12 reverse primer 5'-GCGAACACATCCGGCCTGC-3' (SEQ ID NO:31)). The reaction was cycled in a Rotorgene 2000 or Rotor GENE-Q thermal cycler (QIAGEN) at 95° C.-30 seconds followed by 40 cycles of 95° C.-5 sec, 60° C.-30 sec, 72° C.-30 sec, and 83° C.-15 sec. Melt curves (60-99° C.) were determined at completion of the reaction to ensure a single PCR product was specifically synthesised.

Animal Experimentation

All animal care and experimental procedures were evaluated and approved by the CMRI/CHW Animal Care and Ethics Committee. Male and female C57B1/6 mice between 8-10 weeks of age were purchased from Animal Resources Centre (ARC), Perth. OTC-deficient Spf$^{ash}$ mice (Doolittle et al. 1974) were bred in-house. Mice were housed in standard boxes and received normal food and water ad libitum for the duration of experiments. rAAV was diluted in PBS (without calcium and magnesium) and injected in a 50 μL volume into the intraperitoneal cavity.

Analysis of Livers from rAAV-Injected Mice for GFP Expression

Mice were killed by $CO_2$ inhalation or cervical dislocation and livers were excised for processing. Livers were cut into pieces approx. 1 mm×3 mm thick and fixed for 4-6 hours in a 4% paraformaldehyde solution prepared in PBS (without calcium and magnesium). Additional liver pieces were stored directly at −80° C. for molecular analysis. Paraformaldhyde-fixed liver was progressively incubated in 10% and 20% sucrose solutions (2 hours each incubation) followed by an overnight incubation in a 30% sucrose solution at 4° C. Fixed tissue was frozen in OCT and stored at −80° C. Liver was cut into 5 µM thick sections and mounted on slides for detection of GFP by microscopy.

Molecular biological analysis of livers obtained from mice injected with rAAV was also performed and samples were prepared to contain protein, DNA and RNA. For detection of GFP protein in liver lysates, liver tissue was homogenised in lysis buffer, mixed at 4° C. for one hour followed by centrifugation (800×g) at 4° C. for 20 minutes. Supernatants were assayed for protein concentration using a DC Protein Assay kit (Biorad) as per the manufacturers instructions. GFP concentration in lysates was determined by fluorometry for GFP concentration at excitation/emission wavelengths of 485/535 nm, respectively. GFP concentrations were calculated from a standard curve included in the assay. DNA extracted from liver tissue was assayed for vector provirus copy number using the eGFP qPCR assay described above and normalised against a β-actin-specific qPCR. Total RNA was also extracted from the tissue using an RNAeasy extraction kit (QIAGEN) and reverse transcribed into cDNA as described above. The cDNA was analysed by qPCR using GFP-specific primers and normalised using a β-actin-specific qPCR and vector copy number per cell estimated.

Example 2

Promoter Activity in "Promoter-Less" AAV Vector

A. GFP Expression

Three AAV vectors, pAM-LSP1-GFP, pAM-2/1-46+65BS-GFP-3'UTR, and pAM-CAG-GFP, containing various AAV constructs, (FIG. 1), were transduced into HEK-293 cells (human embryonic kidney cells) and HUH7 cells (a human hepatoma cell line) to determine the levels of GFP expression from the vectors. pAM-LSP1-GFP contains GFP under the transcriptional control of a heterologous promoter containing one copy of the liver-specific hAAT promoter and two copies of the ApoE enhancer element. pAM-2/1-46+65BS-GFP-3'UTR lacks the ApoE/hAAT promoter and instead contains just the 46 nucleotides corresponding to the reverse, complement sequence of nucleotides 4485-4530 of the AAV2 set forth in SEQ ID NO:1 (immediately adjacent the 3' ITR of AAV2, which is at nucleotides 4531-4675 of SEQ ID NO:1) and 65 nucleotides largely derived from the multiple cloning site of the plasmid pBlueScript immediately upstream of the GFP gene. pAM-CAG-GFP contains GFP under the control of the constitutive chicken β-actin promoter.

GFP-expression was detected in significant levels only in HEK-293 cells transduced with rAAV produced by packaging the pAM-CAG-eGFP vector (rAAV-CAG-eGFP; 10%-GFP positive cells). As expected, strong GFP expression was observed in HUH7 ells transduced with rAAV produced by packaging the pAM-LSP1-GFP vector (rAAV-LSP1-GFP; 66% GFP-positive cells). Unexpectedly, strong GFP expression was also observed in HUH7 cells transduced with rAAV produced by packaging the "promoter-less" pAM-2/1-46+65BS-GFP-3'UTR vector (rAAV-2/1-46+65BS-GFP; 60% GFP-positive cells), suggesting that a sequence in the region upstream of GFP containing the ITR set forth in SEQ ID NO:32, 46 (antisense) nucleotides derived from the region immediately adjacent the 3' ITR in AAV2 (set forth in SEQ ID NO:9) and 65 nucleotides from the plasmid pBlueScript had promoter activity.

Figure 2:
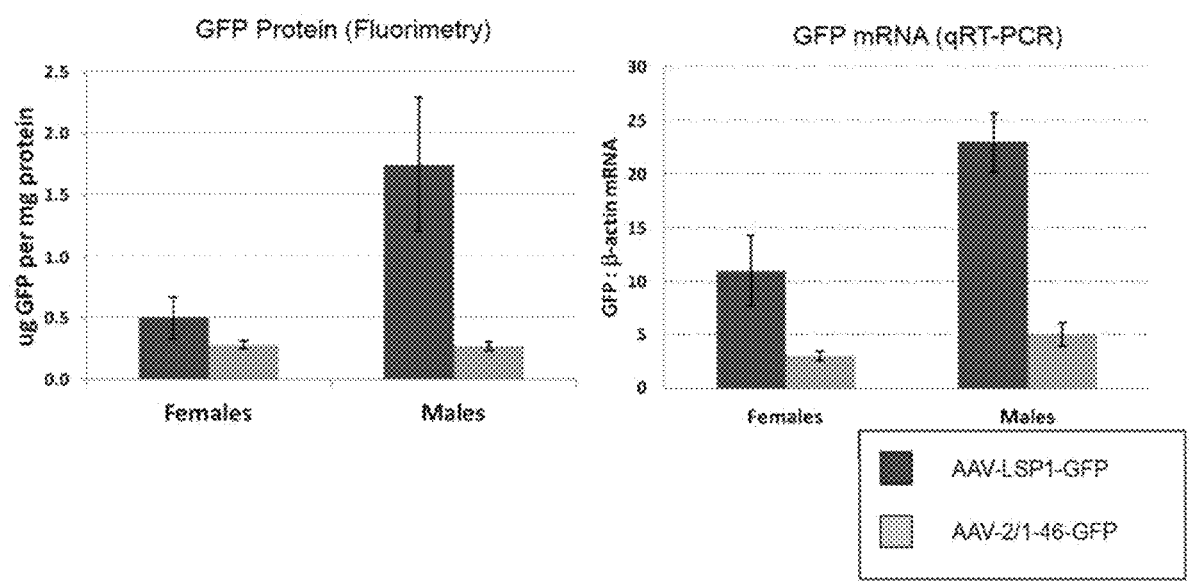
FIG. 2 shows the levels of GFP protein and mRNA in liver cells from C57BL6 mice transduced with rAAV-LSP1-GFP or rAAV-2/1-46+65BS-GFP. All data is expressed per vector genome normalised to GAPDH.
Figure 3:
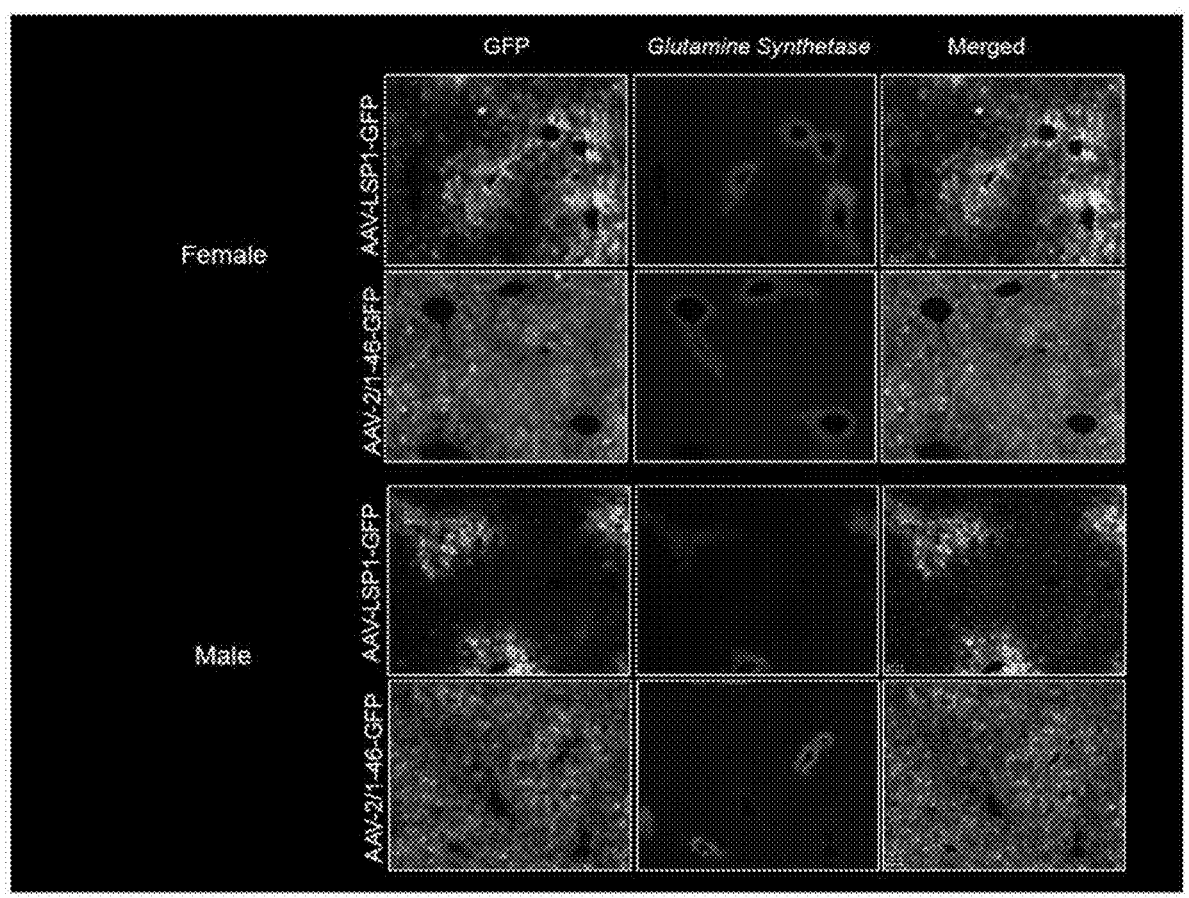
FIG. 3 shows GFP expression in liver lobules from mice transduced with rAAV-LSP1-GFP or rAAV-2/1-46+65BS-GFP. Fluorescence intensity of rAAV-LSP1-GFP sections were reduced to prevent over-exposure.

To confirm this observation, $5 \times 10^{10}$ vg rAAV-LSP1-GFP or rAAV-2/1-46+65BS-GFP, were injected into C57BL/6 mice and the livers of the mice were analysed for GFP expression 14 days later. As shown in FIGS. 2 and 3, GFP mRNA and protein was detected in the livers of mice injected with rAAV-2/1-46+65BS-GFP, although at lower levels than mice injected with rAAV-LSP1-GFP.

B. OTC Expression

To determine whether the new promoter was strong enough to drive expression of therapeutically effective amounts of a protein a new construct was produced using pAM-LSP1-mOTC, which is identical to pAM-LSP1-eGFP except that the former encodes murine OTC cDNA rather than eGFP. pAM-2/1-46+65BS-mOTC was produced by removing the LSP1 heterologous promoter from pAM-LSP1-mOTC via XbaI/SacI restriction digestion followed by DNA blunting and re-ligation. The DNA sequence between ITR and OTC cDNA was therefore identical to pAM-2/1-46+65BS-eGFP. rAAV8-2/1-46+65BS-mOTC was injected into OTC-deficient mice ($spf^{ash}$ mice). OTC activity in wild-type mice, $spf^{ash}$ mice and $spf^{ash}$ mice injected with rAAV8-2/1-46+65BS-mOTC was determined. The urinary orotic acid levels in the mice were also analysed before injection and 14 days after injection to determine whether the rAAV8-2/1-46+65BS-mOTC could drive expression of OTC at levels sufficient to correct the elevated urinary orotic acid levels seen in these mice.

Figure 4:
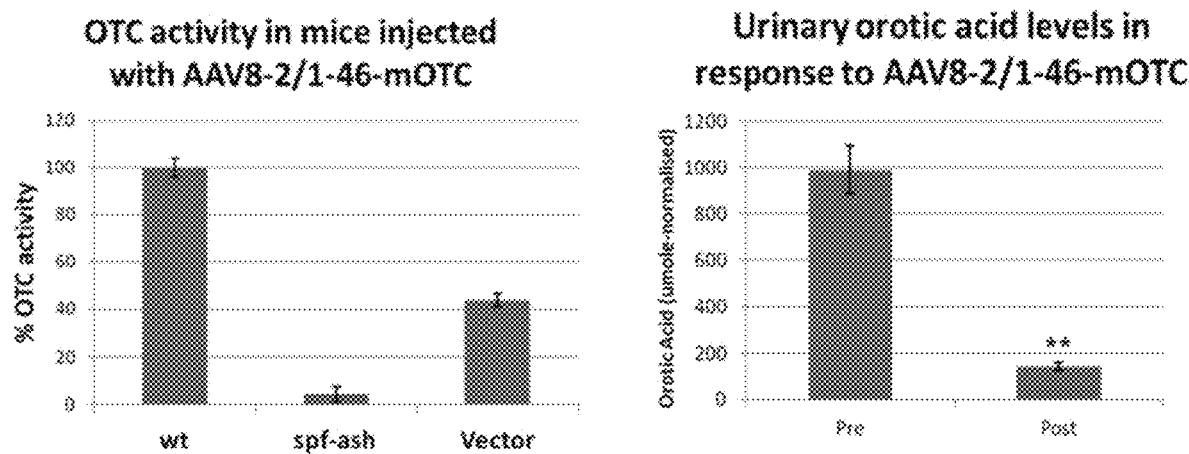
FIG. 4 shows ornithine transcarbamylase (OTC) activity and urinary orotic acid levels in spf$^{ash}$ mice (OTC-deficient) injected with rAAV8-2/1-46+65BS-mOTC. OTC activity in wild-type mice (wt), spf^ash mice (spf-ash) and spf^ash mice injected with rAAV8-2/1-46+65BS-mOTC (vector) was determined. Urinary orotic acid levels in spf^ash mice injected with rAAV8-2/1-46+65-BSmOTC before injection (pre) and after injection (post) were also determined. **Statistically significant by Mann-Whitney test p=0.008 (2-tailed).

As shown in FIG. 4, injection of rAAV8-2/1-46-mOTC into $spf^{ash}$ mice restored approximately 40% of the OTC activity compared to wild-type mice. This level of activity was sufficient to significantly reduce the urinary orotic acid levels in $spf^{ash}$ mice.

Example 3

Promoter Regions in Other AAV Serotypes

A sequence alignment of the reverse, complement sequence of the 3' region adjacent to the 3' ITR of wild type AAV virus from a range of serotypes (AAV1, AAV2, AAV3, AAV4, AAV6 and AAV7) shows sequence homology amongst the serotypes and the presence of several putative binding sites for a hepatocyte nuclear factor (HNF) transcription factor, including HNF1, HNF 1α-c and HNF4α (FIG. 5). The sequence homology and presence of putative HNF binding sites suggested that the promoter activity observed in vectors containing the 46 (antisense) nucleotides derived from the region immediately adjacent the 3' ITR in AAV2 may also be found in the corresponding regions of other AAV serotypes. The additional putative HNF binding sites beyond the 46 nucleotides suggested that a larger portion of this region may have promoter activity.

Figure 6:
FIG. 6 is a schematic showing the subcloning strategy to insert AAV sequences upstream of the GFP gene in the vector so as to measure promoter activity from those sequences.

To investigate this further, vectors containing varying lengths from this region from AAV2, AAV5 and AAV7 were produced and used for packaging into rAAV, as described above and as shown in FIGS. 6 and 7.

Recombinant AAV containing the reverse, complement sequence of the 105 and 133 nucleotides, respectively, immediately adjacent the 3' ITR of the AAV2 set forth in SEQ ID NO:1, were produced and referred to AAV2/1-105-GFP and AAV2/1-133-GFP, respectively. The 105 nucleotide region derived from the reverse, complement of nucleotides 4426-4530 of the AAV2 set forth in SEQ ID NO:1 has the sequence set forth in SEQ ID NO:11, and was inserted into the vector by virtue of the NotI and XbaI restriction enzyme sites at each end, resulting in an insert having the sequence shown in FIG. 7 and set forth in SEQ ID NO:13. The 133 nucleotide region derived from the reverse, complement of nucleotides 4398-4530 of the AAV2 set forth in SEQ ID NO:1 has the sequence set forth in SEQ ID NO:12, and was inserted into the vector by virtue of the NotI and XbaI restriction enzyme sites at each end, resulting in an insert having the sequence shown in FIG. 7 and set forth in SEQ ID NO:14.

Recombinant AAV containing the corresponding nucleotide regions from AAV7 were also produced. AAV7/1-121-GFP and AAV7/1-149-GFP contain the reverse, complement sequence of the 121 and 149 nucleotides, respectively, immediately adjacent the 3' ITR of the AAV7 set forth in SEQ ID NO:7. The 121 nucleotide region derived from the reverse, complement of nucleotides 4455-4576 of the AAV7 set forth in SEQ ID NO:7 has the sequence set forth in SEQ ID NO:15, and was inserted into the vector by virtue of the NotI and XbaI restriction enzyme sites at each end, resulting in an insert having the sequence shown in FIG. 7 and set forth in SEQ ID NO:17. The 149 nucleotide region derived from the reverse, complement of nucleotides 4428-4576 of the AAV7 set forth in SEQ ID NO:7 has the sequence set forth in SEQ ID NO:16, and was inserted into the vector by virtue of the NotI and XbaI restriction enzyme sites at each end, resulting in an insert having the sequence shown in FIG. 7 and set forth in SEQ ID NO:18.

Recombinant AAV containing the corresponding nucleotide regions from AAV5, which shares only limited homology with AAV2, were also produced. AAV5/1-121-GFP and AAV5/1-149-GFP contain the reverse, complement sequence of the 121 and 149 nucleotides, respectively, immediately adjacent the 3' ITR of the AAV5 set forth in SEQ ID NO:5. The 121 nucleotide region has the sequence set forth in SEQ ID NO:19, and was inserted into the vector by virtue of the NotI and XbaI restriction enzyme sites at each end, resulting in an insert having the sequence shown in FIG. 7 and set forth in SEQ ID NO:21. The 149 nucleotide region has the sequence set forth in SEQ ID NO:20, and was inserted into the vector by virtue of the NotI and XbaI restriction enzyme sites at each end, resulting in an insert having the sequence shown in FIG. 7B and set forth in SEQ ID NO:22. As shown in FIG. 7, the sequences derived from AAV5 lack the putative HNF binding sites.

Recombinant AAV containing a 105 nucleotide random sequence (R105; SEQ ID NO:23) in place of the AAV-derived regions was also generated as a control (referred to a rAAV-R105-GFP).

HUH7 and HEK-293 cells were transduced with the rAAV and GFP expression in cells and assessed by FACs analysis. It was observed that AAV2/1-105-GFP produced higher levels of expression (63.2% and 63% GFP-positive cells over two experiments) than the original construct that contains 46 nucleotides of AAV2 sequence and 65 nucleotides multiple cloning site (46% and 49% GFP-positive cells over two experiments). AAV2/1-133-GFP showed comparable ability to induce GFP expression (51.3% and 66% GFP-positive cells over two experiments). Transduction of HUH7 cells with AAV7/1-121-GFP, which also contains putative HNF transcription factor binding sites, also produced GFP expression although perhaps not to levels found with AAV2/1-105-GFP (49.9% and 76% GFP-positive cells over two experiments). Transduction of HUH7 cells with AAV7/1-149-GFP resulted lower GFP expression (13.4% and 76% GFP-positive cells over two experiments). The corresponding regions from AAV5 showed no or minimal promoter activity. Interestingly, the vector containing the random sequence R105 facilitated some GFP expression, suggesting that there may be some promoter activity within the ITR in the vector. No significant GFP expression was observed in the non-liver cell line HEK-293, supporting the notion that the promoter activity may be restricted to liver-derived cells.

The transduced cells were analysed by qPCR to determine the number of copies of vector, so as to eliminate the possibility that differences in GFP expression were due purely to differences in transduction efficiency. All samples showed similar vector copy numbers with no correlation between GFP activity and vector provirus. This indicates that the differences in GFP expression were due to differences in transcriptional activity resulting from different promoters than differences in transduction efficiency.

Example 4

Further Characterization of the Promoter

Additional AAV vectors containing the reverse, complement of just the 46 nucleotides immediately adjacent the 3' ITR of the AAV2 set forth in SEQ ID NO:1 (i.e. not containing the 65 nucleotides from pBluescript), or just the 75, 105 or 133 nucleotides immediately adjacent the 3' ITR of the AAV2 set forth in SEQ ID NO:1, were produced to further characterize the sequence required for promoter activity. These vectors were then used to produce rAAV: rAAV 2/1-46-GFP, rAAV 2/1-75-GFP, rAAV 2/1-105-GFP, rAAV 2/1-133-GFP containing the 46 nucleotides set forth in SEQ ID NO:9, the 75 nucleotides set forth in SEQ ID NO:10, the 105 nucleotides set forth in SEQ ID NO:11, and the 133 nucleotides set forth in SEQ ID NO:12. These rAAV were then transduced into HUH7 cells.

GFP expression from rAAV 2/1-75-GFP in HUH7 cells was slightly lower (31% GFP-positive cells) than that observed for the rAAV 2/1-105-GFP (53% GFP-positive cells) and rAAV 2/1-133-GFP (60% GFP-positive cells). Little GFP expression was observed in HUH7 cells transduced with rAAV 2/1-46-GFP. As assessed by qPCR, the number of copies of vector was similar for all groups (data not shown).

In vivo validation of the AAV-2/1-105-GFP vector pseudo-serotyped in capsid 8 (rAAV-2/1-105-GFP) was performed in male and female mice as described in Example 1. rAAV-2/1-105-GFP induced eGFP expression in the murine liver with no differences between male and female mice with respect to eGFP mRNA (FIG. 8A) and protein levels (FIG. 8B), which contrasted with the gender differences for rAAV-LSP1-GFP. However, unlike rAAV-LSP1-GFP, rAAV-2/1-105-GFP produced a more obvious pericentral GFP expression pattern in male but not female mice (data not shown) indicating that the 2/1-105 nucleotides impose regulatory effects on the expression cassette in a gender-specific manner.

Example 5

Transcriptional Start Site Mapping

Studies were performed to map the transcriptional start site of rAAV 2/1-46+65BS-GFP after liver transduction in 15 female mice and 19 male mice. Briefly, total RNA was extracted from liver samples of representative male and female mice transduced with AAV-2/1-46+65BS-GFP in the experiments described in Example 2A using an RNeasy Mini kit as per the manufacturer's instructions (QIAGEN). The transcriptional start site was mapped using the Exact-START Eukaryotic mRNA 5' and 3' Race Kit as per the manufacturer's instructions (Epicentre) using the kit's 5'forward primer and a GFP-specific reverse primer. The resulting cDNA were sub-cloned to the TA cloning vector pGEM-T-easy as per the manufacture's instructions (Promega Corporation) and the cDNA inserts (representing 5' mRNA of GFP-encoding transcripts) were subjected to Sanger sequencing at the Australian Genome Research Facility Ltd. Sequences were aligned to the AAV-2/1-46+65BS-GFP vector genome.

Table 2 summarizes the results of the studies, showing the number of base pairs upstream of the ATG start codon of the GFP gene that transcription was initiated in each mouse. It was observed that transcription typically started 21-57 base pairs upstream of the ATG start codon of the GFP gene (i.e. within the 65 nucleotides derived from pBlueScript), although in one male mouse, transcription started 96 base pairs upstream of the ATG start codon, which is within the promoter region (i.e. within the 46 nucleotides derived from AAV).

TABLE 2

Transcription start sites

| | Transcription initiation (base pairs upstream of ATG) | |
|---|---|---|
| Mouse number | Female | Male |
| 1 | 57 | 96 |
| 2 | 56 | 56 |
| 3 | 54 | 56 |
| 4 | 33 | 54 |
| 5 | 33 | 54 |
| 6 | 33 | 39 |
| 7 | 33 | 33 |
| 8 | 33 | 33 |
| 9 | 33 | 33 |
| 10 | 21 | 21 |
| 11 | 56 | 56 |
| 12 | 56 | 56 |
| 13 | 33 | 56 |
| 14 | 33 | 56 |
| 15 | 33 | 54 |
| 16 | NA | 48 |
| 17 | NA | 45 |
| 18 | NA | 34 |
| 19 | NA | 33 |

Example 6

Assessment of the Role of the ITR in Transcriptional Activity

To determine whether transcription from the 2/1-105 element occurs autonomously or in unison with the AAV ITR, transfection studies were undertaken to measure reporter expression from 2/1-105 either with or without the upstream A/D junction, which is a region of the ITR known to be important for transcriptional activity.

Briefly, primers were designed to PCR amplify DNA from AAV-2/1-105-GFP such that PCR products contained (i) the 2/1-105 element containing the A/D ITR junction shown to be important for ITR transcriptional activity, (ii) the 2/1-105 element without A/D junction, or (iii) the eGFP cassette without upstream sequence (FIG. 9A). All reactions used the same reverse primer homologous to the BGH poly-adenylation site. PCR amplified DNA was similarly generated from AAV-R105-GFP using the ITR specific primer or a primer designed to capture the 105 nucleotides of random sequence.

DNA fragments were then transfected into HUH7 cells in duplicate and analyzed 48 hours post-transfection for the proportion of eGFP positive HUH7 cells and MFI of positive cells. HUH7 cells transfected with 2/1-105-GFP exhibited a substantially higher proportion of eGFP$^+$ cells when compared with cultures transfected with R105-GFP indicating reporter expression from 2/1-105 independent of AAV ITR (FIG. 9B). A similar proportion of eGFP$^+$ HUH7 were observed post-transfection of 2/1-105 irrespective of whether the A/D junction was present or absent (FIG. 9B) although the MFI was slightly higher when the ITR sequence was included (FIG. 9C). Expression from a control co-transfected mCherry expression plasmid was similar across cultures, confirming comparable transfection efficiencies in the experiment (FIGS. 9D and E).

These results demonstrate that the 2/1-105 element can operate independently of the ITR although the presence of the A/D junction further enhances transcriptional activity.

Example 7

Cell-Specificity

The transcriptional activity of AAV2-2/1-105-GFP was assessed across a panel of mammalian cell lines to evaluate the cell specificity of the promoter. Vectors were packaged into capsid serotype DJ as described in Example 1. Capsid DJ was selected for its broad transduction of a range of cell types. AAVDJ-R105-GFP, AAVDJ-LSP1-GFP and AAVDJ-CAG-GFP were included as controls for basal activity, liver specificity and cellular permissiveness to AAV transduction, respectively. The vectors were transduced into HUH7, A549, BWTG3, MRC5, Caco-2, HeLa, K562 and SK-UT-1 and cells lines.

Figure 10:
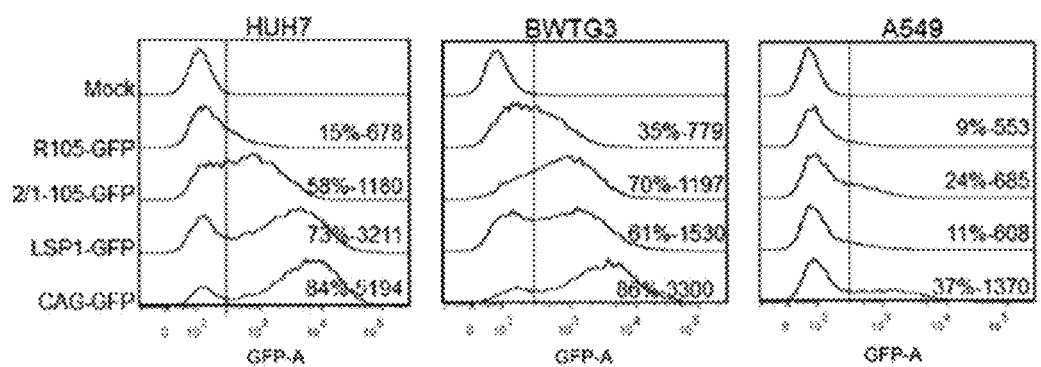
FIG. 10 shows the results of transduction of HUH7, BWTG3 and A549 cell lines with rAAV produced by packing the vectors into capsid serotype DJ. Cell lines were transduced with DJ-capsid packaged vector AAV-R105-GFP, AAV-2/1-105, AAV-LSP1-GFP or AAV-CAG-GFP. Percentage of eGFP and MFI above baseline are indicated for each condition. Data are representative of two independent experiments.

For MRC5, SK-UT-1 and HeLa cell lines, no eGFP expression was detected after transduction with any vector except AAVDJ-CAG-GFP (data not shown). The same was found for Caco-2 and K562 although AAVDJ-CAG-GFP transduced the lines relatively poorly, producing 12% and 4% eGFP$^+$ cells, respectively (data not shown). In contrast, the murine hepatocellular carcinoma cell line BWTG3 showed eGFP expression after AAVDJ-2/1-105-GFP transduction with a higher proportion of eGFP$^+$ cells than AAVDJ-LSP1-GFP, albeit at lower MFI, indicating an active AAV promoter element in cells of liver origin (FIG. 10). Interestingly, A549 (derived from a human lung carcinoma) transduction by AAVDJ-2/1-105-GFP showed both a higher proportion and MFI compared to AAVDJ-LSP1-GFP transduction. This contrasted with HUH7 cells, which were included in the experiment to validate vector performance, where AAVDJ-LSP1-GFP was superior to AAVDJ-2/1-105-GFP. Also of note was the high basal level of eGFP expression induced by AAVDJ-R105-GFP transduction in BWTG, A549 and HUH7, implying the ITR is transcriptionally active in these lines. Collectively, these data indicate that both the 2/1-105 promoter element as well as the AAV2 ITR are transcriptionally operational in a cell-restricted manner.

Example 8

Enhancer Activity

Figure 11:
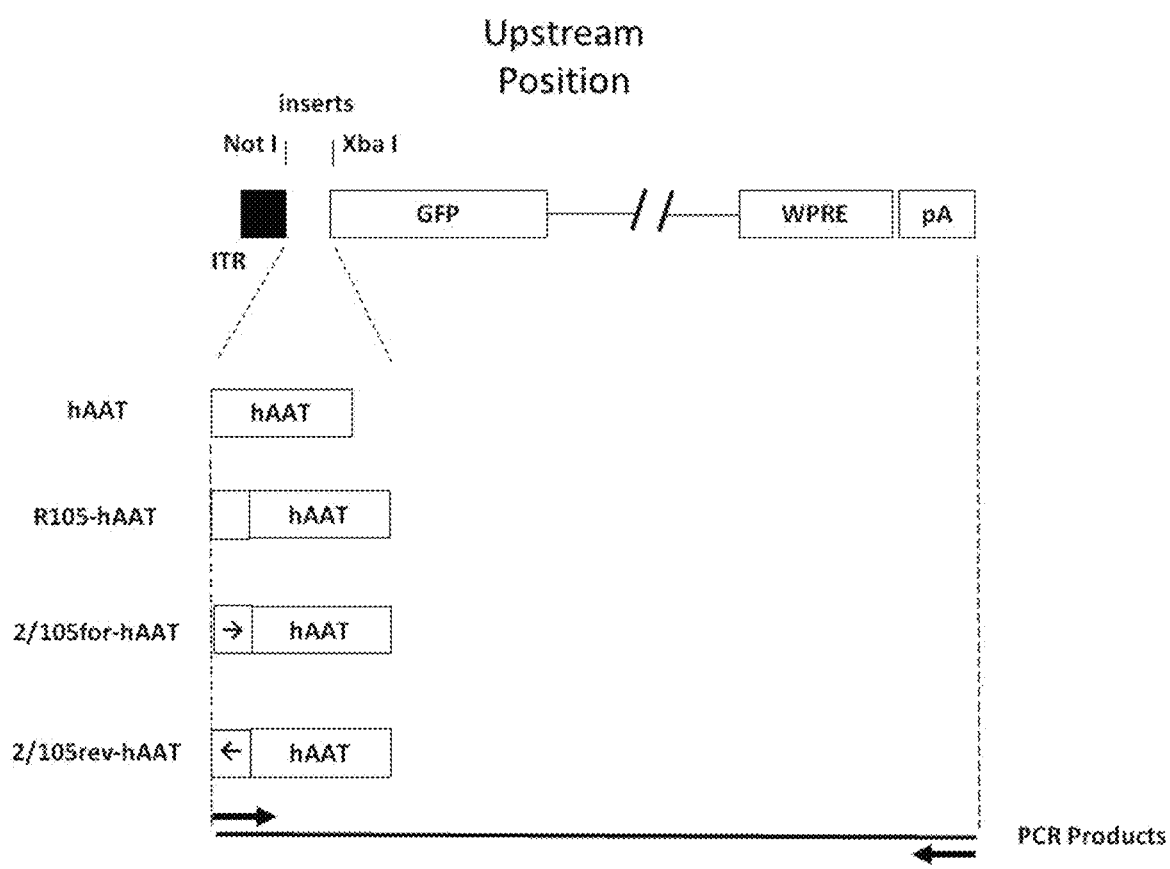
FIG. 11 shows the cloning strategy to produce the vectors to test for enhancer activity of the 2/1-105 element. (A) Cloning strategy to assess for enhancer activity of the 2/1-105 element upstream of the hAAT promoter. (B) Cloning strategy to assess for enhancer activity of the 2/1-105 element downstream of the hAAT promoter.
Figure 11:
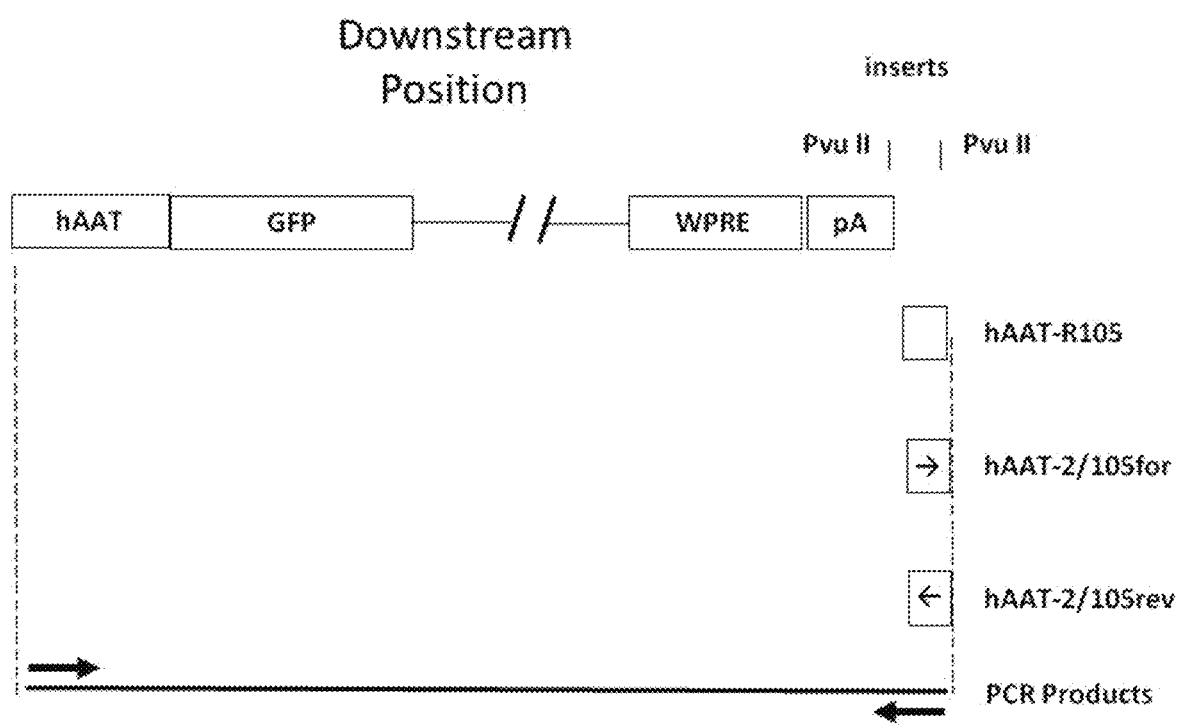

To test for enhancer activity of the newly-identified promoter region, the 2/1-105 element was inserted into a vector either upstream or downstream, and in either the forward or reverse orientation, of the hAAT promoter, which was operably linked to GFP. The level of GFP expression was then examined. The R105 element was also used as a control. Specifically, constructs with elements positioned upstream of the GFP expression cassette were prepared from pR105-GFP using the NEBuilder HiFI cloning system (New England Biolabs Inc.) as per the manufacturer's instructions. The hAAT promoter was PCR amplified from pAM-LSP1-eGFP and assembled into NotI/XbaI restricted pR105-GFP. For constructs containing elements upstream of the hAAT promoter, assembly reactions also included PCR-amplified products containing the R105 nucleotide sequence or the 2/1-105 element such that it would be assembled with the hAAT promoter in either orientation. Constructs with elements positioned downstream of the polyadenylation signal were similarly produced with NEBuilder assembly reactions containing Pvu II-restricted phAAT-GFP and PCR-amplified products either with the R105 nucleotide sequence or the 2/1-105 element such that it would be assembled in either orientation. FIG. 11 provides a schematic of the cloning strategy to produce the constructs.

Figure 12:
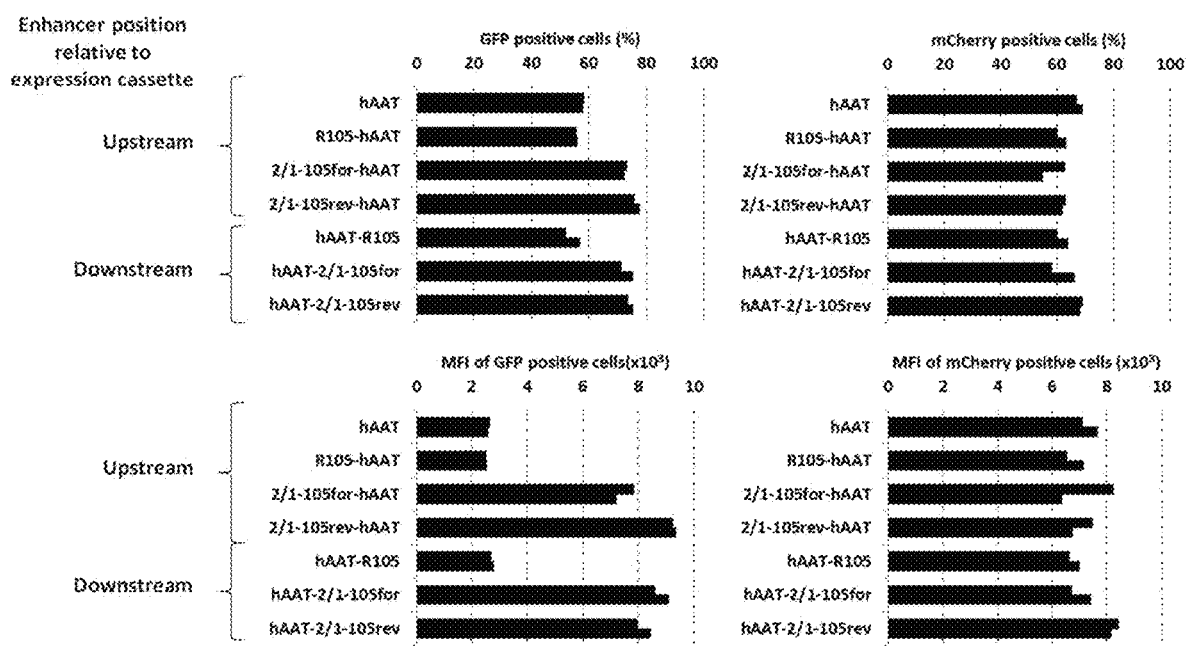
FIG. 12 shows the results of a transfection study to assess for enhancer activity the 2/1-105 element either upstream or downstream of the hAAT promoter, and in either the forward or reverse orientation. The number of GFP positive cells and the MFI of the GFP positive cells was assessed.

The constructs were then transfected into HUH7 cells and GFP expression analysed as described above. The results shown in FIG. 12 are representative of three independent experiments. As expected, the proportion of GFP-positive cells was similar for all constructs. However, there was an increase in mean fluorescent intensity of GFP positive cells when the 2/1-105 element was included in the construct. This was observed regardless of whether the 2/1-105 element was upstream or downstream of the hAAT promoter or whether it was in the forward or reverse orientation relative to the GFP cassette. This indicates that the 2/1-105 element possesses enhancer activity such that the activity of the hAAT promoter is enhanced by the presence of the element irrespective of position and orientation. The mCherry controls confirm equivalent transfection efficiencies across cultures.

The invention claimed is:

1. A vector, comprising, from 5' to 3', a 5' ITR, a promoter, and a 3' ITR, wherein:
the promoter is the only promoter between the 5' ITR and the 3' ITR; and
the promoter comprises a sequence of nucleotides that is the reverse, complement sequence of nucleotides selected from the group consisting of nucleotides 4398-4530 of the AAV2 genome of SEQ ID NO:1, nucleotides 4426-4580 of the AAV1 genome comprising the nucleotide sequence of SEQ ID NO:2, nucleotides 4412-4580 of the AAV3 genome comprising the nucleotide sequence of SEQ ID NO:3, nucleotides 4457-4623 of the AAV4 genome comprising the nucleotide sequence of SEQ ID NO:4, nucleotides 4411-4538 of the AAV6 genome comprising the nucleotide sequence of SEQ ID NO:6, nucleotides 4428-4576 of the AAV7 genome comprising the nucleotide sequence of SEQ ID NO:7, and nucleotides 4330-4393 of the AAV8 genome comprising the nucleotide sequence of SEQ ID NO:8.

2. The vector of claim 1, wherein the 5' ITR and the 3' ITR are from AAV viruses of the same or different serotypes.

3. The vector of claim 1, wherein the 5' ITR and the 3' ITR are from AAV1, AAV2, AAV3, AAV4, AAV5, AAV6, AAV7 or AAV8 serotypes.

4. The vector of claim 1, wherein the 5' ITR or the 3' ITR comprises a sequence having at least 90% sequence identity to the AAV2 ITR comprising the nucleotide sequence of SEQ ID NO:24, 25 or 32.

5. The vector of claim 1, further comprising a spacer sequence immediately downstream of the promoter, wherein the total length of the promoter and the spacer is at least 60, 70, 80, 90, 100, 110, 120, or 130 nucleotides.

6. The vector of claim 1, wherein the vector comprises one or more restriction enzyme sites positioned downstream of the promoter to facilitate insertion of a heterologous coding sequence that is operably linked to the promoter.

7. The vector of claim 1, wherein the vector comprises a heterologous coding sequence operably linked to the promoter.

8. The vector of claim 7, wherein the heterologous coding sequence encodes a peptide, a polypeptide, or a polynucleotide.

9. The vector of claim 8, wherein the polynucleotide is an antisense oligonucleotide.

10. A method for expressing the heterologous coding sequence of claim 7, comprising introducing directly into a host cell the vector of claim 7, wherein the host cell mediates the expression of the heterologous coding sequence of claim 7.

11. A vector, comprising, from 5' to 3', a 5' ITR, a promoter, and a 3' ITR, wherein:
the promoter is the only promoter between the 5' ITR and the 3' ITR, and
the promoter comprises the nucleotide sequence of any one of SEQ ID NOs:9-12, or a sequence having at least 90% sequence identity to the nucleotide sequence of any one of SEQ ID NOs:9-12.

12. The vector of claim 11, wherein the 5' ITR and the 3' ITR are from AAV viruses of the same or different serotypes.

13. The vector of claim 11, wherein the 5' ITR and the 3' ITR are from AAV1, AAV2, AAV3, AAV4, AAV5, AAV6, AAV7 or AAV8 serotypes.

14. The vector of claim 11, wherein the 5' ITR or the 3' ITR comprises a sequence having at least 90% sequence identity to the AAV2 ITR comprising the nucleotide sequence of SEQ ID NO:24, 25 or 32.

15. The vector of claim 11, further comprising a spacer sequence immediately downstream of the promoter, wherein the total length of the promoter and the spacer is at least 60, 70, 80, 90, 100, 110, 120, or 130 nucleotides.

16. The vector of claim 11, wherein the vector comprises one or more restriction enzyme sites positioned downstream of the promoter to facilitate insertion of a heterologous coding sequence that is operably linked to the promoter.

17. The vector of claim 11, wherein the vector comprises a heterologous coding sequence operably linked to the promoter.

18. The vector of claim 17, wherein the heterologous coding sequence encodes a peptide, a polypeptide, or a polynucleotide.

19. The vector of claim 18, wherein the polynucleotide is an antisense oligonucleotide.

20. A recombinant AAV having a genome that comprises, from 5' to 3', a 5' ITR, a promoter, and a 3' ITR, wherein:
the promoter is the only promoter between the 5' ITR and the 3' ITR; and
the promoter comprises:
(a) a sequence of nucleotides that is the reverse, complement sequence of nucleotides 4398-4530 of the AAV2 genome of SEQ ID NO:1, nucleotides 4426-4580 of the AAV1 genome comprising the nucleotide sequence of SEQ ID NO:2, nucleotides 4412-4580 of the AAV3 genome comprising the nucleotide sequence of SEQ ID NO:3, nucleotides 4457-4623 of the AAV4 genome comprising the nucleotide sequence of SEQ ID NO:4, nucleotides 4411-4538 of the AAV6 genome comprising the nucleotide sequence of SEQ ID NO:6, nucleotides 4428-4576 of the AAV7 genome comprising the nucleotide sequence of SEQ ID NO:7, and nucleotides 4330-4393 of the AAV8 genome comprising the nucleotide sequence of SEQ ID NO:8; or
(b) a sequence of any one of SEQ ID NOs:9-12, or a sequence having at least 90% sequence identity to the nucleotide sequence of any one of SEQ ID NOs:9-12.

21. The recombinant AAV of claim 20, wherein the promoter is operably linked to a heterologous coding sequence.

22. A method for expressing the heterologous coding sequence of claim 21, comprising introducing directly into a host cell the recombinant AAV of claim 21, wherein the host cell mediates the expression of the heterologous coding sequence of claim 21.

* * * * *